(12) United States Patent
Silbiger et al.

(10) Patent No.: US 6,562,596 B1
(45) Date of Patent: May 13, 2003

(54) TISSUE INHIBITOR OF METALLOPROTEINASE TYPE THREE (TIMP-3) COMPOSITION AND METHODS

(75) Inventors: Scott M. Silbiger, Woodland Hills, CA (US); Raymond A. Koski, Old Lyme Road, CT (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 08/134,231

(22) Filed: Oct. 6, 1993

(51) Int. Cl.$^7$ ................................................ C12P 21/02
(52) U.S. Cl. .................... 435/69.2; 435/325; 435/252.3; 435/69.1; 435/320.1; 536/23.5
(58) Field of Search .......................... 536/23.5, 24.31; 435/240.2, 252.3, 320.1, 69.2, 325, 69.1

(56) References Cited

U.S. PATENT DOCUMENTS

| | | | |
|---|---|---|---|
| 4,179,337 A | 12/1979 | Davis et al. ................ | 435/181 |
| 4,710,473 A | 12/1987 | Morris ..................... | 435/320.1 |

FOREIGN PATENT DOCUMENTS

| | | |
|---|---|---|
| EP | 0398 753 | 11/1990 |
| WO | 91/05795 | 5/1991 |

OTHER PUBLICATIONS

Pavloff et al., J. Biol. Chem. 267:17321–17326 (1992).*
Apodaca et al., Cancer Res. 50:2322–2329 (1990).*
Cocuzzi et al., FEBS Letters 307:375–378 (1992).*
Jones et al., FEBS Letters 352:171–174 (1994).*
Apte et al., Genomics 19:86–90 (1994).*
Uria et al., Cancer Res. 54:2091–2094 (1994).*
Vincenti et al., Arthritis and Rheumatism 37:1115–1126 (1994).*
Zucker et al., Int. J. Cancer 52:366–371 (1992).*
Banda et al., Biochem. J. 193: 589–605 (1981).
Baron et al., Cell 28: 395–404 (1982).
Bauer et al., J. Exp. Med. 148: 1378–1387 (1978).
Boone et al., PNAS–USA 87: 2800–2804 (1990).
Branstrom et al., Endocrinology 122: 1715–1721 (1988).
Brown et al., American J. of Ophthalmology 72: 1139–1142 (1971).
Carlos et al., Immunol. Rev. 114: 5–28 (1990).
Carmichael et al., PNAS–USA 83: 2407–2411 (1986).
Cawston et al., J. Biochem. 211: 313–318 (1983).
Chomczynski and Sacchi, Anal. Biochem. 162: 156–159 (1987).
Collier et al., Genomics 9: 429–434 (1991).
D'Armiento et al., Cell 71: 955–961 (1992).
Madshus et al. J. Biol. Chem. 266: 17446–17453 (1991).
DeClerck et al., Cancer Research 46: 3580–3586 (1986).
Docherty et al., Nature 318: 66–69 (1985).
Dressman et al., Nature 295: 158–160 (1982).
Edwards et al., Nucleic Acid. Res. 14: 8863–8878 (1986).
Evanson et al. J. Clin. Invest. 47: 2639–2651 (1968).
Freudenstein et al., Biochem. Biophys. Res. Comm. 171: 250–256 (1990).
Friedman et al., Nucl. Acids Res. 16: 8718 (1988).
Gewert et al., EMBO 6: 651–657 (1987).
Glorieux et al., Cancer 58: 2136–2139 (1986).
Goldberg, G.I., J. Biol. Chem. 261: 6600–6605 (1986).
Graeve et al., Cancer 62: 2125–2127 (1988).
Grivskov et al., Nucl. Acids Res. 14: 6745–6763 (1986).
Hewick et al., J. Biol. Chem., 256: 7990–7997 (1981).
Hibbs et al., J. Biol. Chem. 260: 2493–2500 (1985).
Hicks et al., Int. J. Cancer 33: 835–844 (1984).
Horowitz et al., J. Biol. Chem. 264: 7092–7095 (1989).
Huse et al., Science 246: 1275–1281 (1989).
Johnson et al., Mol. Cell. Biol. 7: 2821–2829 (1987).
Kaiser et al. Science 223: 249–255 (1984).
Khokho et al., Science 243: 947–950 (1989).
Kohler and Milstein Eur. J. Immunol. 6, 511–519 (1976).
Lerner et al., Cell 23: 309–310 (1981).
Lerner et al., PNAS–USA, 78: 3403–3407 (1981).
Lerner et al., Scientific Am., 248: 66–74 (1983).
Liotta et al., Biochem. Biophys. Res. Commun. 98: 184–198 (1981).
Liotta et al., Nature 284: 67–68 (1980).
Liotta et al., PNAS–USA 76: 2268–2272 (1979).
Matrisian, Trends In Genetics 6: 121–125 (1990).
McCartney et al., Eur. J. Biochem. 130: 79–83 (1983).
Murphy et al. Biochem. J. 203: 209–221 (1982).
Murphy et al., Biochem. J. 195: 167–170 (1981).
Murray et al., J. Biol. Chem. 261: 4154–4159 (1986).
Palmiter et al., Science 222: 809–814 (1983).
Pisko et al., J. Immunol. 136: 2141–2150 (1986).
Remington's Pharmaceutical Sciences, 18th Ed. (1990, Mack Publishing Co., Easton, PA 18042) pp. 697–773.
Ross et al., Nature 294: 654–656 (1981).
Salo et al., J. Biol. Chem. 258: 3058–3063 (1983).
Schultz et al., Cancer Research 48: 5539–5545 (1988).
Shimizu et al., Gene 114: 291–292 (1992).
Slansky et al., Annals of Ophthalmology 2: 488–491 (1970).
Staskus et al., J. Biol. Chem. 266: 449–454 (1991).
Stetler–Stevenson, et al. J. Biol. Chem., 264: 17374–17378 (1989).
Stricklin et al., J. Biol. Chem. 258: 12252–12258 (1983).
Tartof and Hobbs, Bethesda Res. Lab. Focus 9: 12 (1987).
Thorgeirsson et al., J. Natl. Canc. Inst. 69: 1049–1054 (1982).

(List continued on next page.)

Primary Examiner—James Martinell
(74) Attorney, Agent, or Firm—Finnegan, Henderson, Farabow, Garrett & Dunner, LLP

(57) ABSTRACT

The present invention relates in general to metalloproteinase inhibitors and to polynucleotides encoding such inhibitors. In particular, the invention relates to novel mammalian inhibitors of metalloproteinase, which are designated as type three or TIMP-3, to fragments, derivatives, and analogs thereof, and to polynucleotides encoding the same. Novel methods of producing such compositions and novel methods of using such compositions are also provided.

15 Claims, 42 Drawing Sheets

OTHER PUBLICATIONS

Tolley et al., J. Mol. Biol. 229: 1163–1164(1993).
Tramontano et al. Nucleic Acid Res. 12: 5049–5059 (1984).
V.–J. Uitto, pp. 211–223 in *Proteinases in Inflammation and Tumor Invasion,* H. Tschesche, ed., Walter de Gruyter & Co., Berlin, N.Y. (1988).
Van Ranst et al., Cytokine 3: 231–239 (1991).
Verma, Scientific American, Nov. 68–84 (1990).
Walter et al., PNAS–USA 77: 5197–5200 (1980).
Walter et al., PNAS–USA 78: 4882–4886 (1981).
Weiland et al., Blut 44: 173–175 (1982).
Werb et al. J. Exp. Med. 142: 346–360 (1975).
Willenbrock et al., Biochemistry 32: 4330–4337 (1993).
Nigg et al., PNAS–USA 79: 5322–5326 (1982).
Woolley et al., Arthritis and Rheumatism 20: 1231–1239 (1977).
Yang et al., PNAS–USA 89: 10676–10680 (1992).
Kishnani et al., FASEB J., 7, abstract 2148 (1993).
Herron et al., J. Biol. Chem., 261, 2814–2812 (1986).
Stetler–Stevenson et al., J. Biol. Chem. 265, 13933–13938 (1990).
Silbiger et al., Gene, 141, 293–297 (1994).
Leco et al., J. Biol. Chem., 269, 9352–9360 (1994).

* cited by examiner

```
GGCGGCGGGCGCTCAGACGGCTTCTCCTCCTCTTGCTCCTCCCAAGCTCCTT     60
CGCCGGGAGCCCGCCGAGTCCTGCGCCAGCAGCCGAGGAGGCCCTCGCTGCGCCCAT    120
CCCGTCCCGGCCACTCGGAGGGCCCGCCAAGGTTGCCCCGGCCACGGCC            180
CGCCGAGCGAGCAGCTCGGGCGGCGCCCCCGGGCCGCGCCGGCAACTTTGG          240
AGAGGCGAGCAGCCCCGGCCAGCAGCGGCGGGCAATGACCCCTTGGCTGGGC         300
                              MetThrProTrpLeuGlyLeu          -17
                              -23

TCATCGTGCTCCTGGGAGCCTGGAGCTGGGGGACTGGGGCGCCGAGCCGC           360
IleValLeuLeuGlySerTrpSerTrpGlyAspTrpGlyAlaGluProArg            4
                                         -1 +1

CGCCCAGCACCCCAGGAGGACGCCTTCTGCAACTCCGACATCGTGATCCGGGCCAAGGTGG 420
ProSerHisProGlnAspAlaPheCysAsnSerAspIleValIleArgAlaLysValVal  24

TGGGAAGAAGCTGGTAAAGGAGGGCCACGCTGGTCTACACCATCAAGCAGA           480
GlyLysLysLeuValLysGluGlyProPheGlyThrLeuValTyrThrIleLysGlnMet  44

TGAAGATGTACCGAGGCTTCACCAAGCTTCAGTACATCCATACGGAAGCTT           540
LysMetTyrArgGlyPheThrLysMetProHisValGlnTyrIleHisThrGluAlaSer  64

CCGAGAGTCTCTGTGCCTAAGCTGGAGTCAACAAGTACCTGCTGACAGGTC           600
GluSerLeuCysGlyLeuLysTyrGlnTyrLeuLeuThrGlyArg                 84
```

FIG. 1A

```
GCGTCTATGATGGCAAGATGTACACGGGGCTGTGCAACTTCGTGGAGAGGTGGACCAGC         660
 ValTyrAspGlyLysMetTyrThrGlyLeuCysAsnPheValGluArgTrpAspGlnLeu        104

TCACCCTCTCCAGCGCGCAAGGGGCTGAACTATCGGTATCACCTGGGTTGTAACTGCAAGA       720
 ThrLeuSerGlnArgLysGlyLeuAsnTyrArgTyrHisLeuGlyCysAsnCysLysIle        124

TCAAGTCCTGCTACTACCTGCCCTTTGTGACTTCCAAGAACGAGTGTCTCTGGACCG           780
 LysSerCysTyrTyrLeuProCysPheValThrSerLysAsnGluCysLeuTrpThrAsp        144

ACATGCTCTCCAATTTCGGTTACCCTGGCTACCAGTCCAAACACTACGCCTGCATCCGGC        840
 MetLeuSerAsnPheGlyTyrProGlyTyrGlnSerLysHisTyrAlaCysIleArgGln        164

AGAAGGGCGGCTACTGCAGCTGGTACCGAGGATGGGCCCCCGGATAAAAGCATCA             900
 LysGlyGlyTyrCysSerTrpTyrArgGlyTrpAlaProProAspLysSerIleIleAsn        184

ATGCCACAGACCCCTGAGCGCCAGACCCTGCCCCACTTCCCTCCCCTTCCCGCTGA            960
 AlaThrAspProEnd     SEQ ID NO: 13                                   188

GCTTCCCTTGGACACTAACTCTTCCCAGATGATGACAATGAAATTAGTGCCTGTTTCTT        1020
GCAAATTTAGCACTTGGAAATTTAAAGAAAGGTCTATGCTGTCTATATGGGGTTATTGG        1080
GAACTATCCTCCTGGCCCCACCCCTGCCCTTTGTTTTTGACATCATTCATTTCCA            1140
CCTGGCAATTCTGGTGCCAGCCATGCCAATCTCATTCCTCTTCTTCGTG                  1200
ATAATATAATCTCTATTTTTTTAGGAAAAAAAAAAAAA  SEQ ID NO: 12               1240
******
```

FIG. 1B

AMINO ACID SEQUENCES OF TIMP FAMILY MEMBERS

```
         -23                                                         1                                    24
Bovine TIMP-1  ...MAPFAPM ASGILLLLWL TAPSRA Y........QR  [CTCV PPHPQTAFCN SDVVIRAKFV
Human TIMP-1   ...MAPFEPL ASGILLLLWL IAPSRA Y........QR  [CTCV PPHPQTAFCN SDLVIRAKFV
Rabbit TIMP-1  ...MAPLAAL ASSMLLLWL  VAPSRA Y........QR  [CTCV PPHPQTAFCN SDLVIRAKFV
Mouse TIMP-1   ..MMAPFASL ASGILLLLSL IASSKA Y........QR  [CSCA PPHPQTAFCN SDLVIRAKFM
Bovine TIMP-2  MGAAARSLPL AFCLLLLGTL LPRADA                [CSCS PVHPQQAFCN ADIVIRAKAV
Human TIMP-2   MGAAARTLRL ALGLLLLATL LRPADA                [CSCS PVHPQQAFCN ADVIRAKAV
Mouse TIMP-2   MGAAARSLRL ALGLLLASL  VRPADA                [CSCS PVHPQQAFCN ADVIRAKAV
Chick TIMP-3   MTAWLGFLAV FLCSWSLRDL ..VAEA                [CTCV PIGPQDAFCN SDIVIRAKVV
Human TIMP-3   MTPWLGLI.V LLGSWSLGDW ..GAEA                [CTCS PSHPQDAFCN SDIVIRAKVV
                                            * * *
               25                                                                            65
Bovine TIMP-1  GTAEVNETAL Y........QR YEIKMTKMFK  GFSALRDAPD IRFIYTPAME
Human TIMP-1   GTPEVNQTTL Y........QR YEIKMTKMYK  GFQALGDAAD IRFVYTPAME
Rabbit TIMP-1  GAPEVNHTTL Y........QR YEIKTTKMFK  GFDALGHATD IRFVYTPAME
Mouse TIMP-1   GSPEINETTL Y........QR YKIKMTKMLK  GFKAVGNAAD IRYAYTPVME
Bovine TIMP-2  NKKEVDSGND IYGNPIKRIQ YEIKQIKMFK  GPDQ......D IEFIYTAPAA
Human TIMP-2   SEKEVDSGND IYGNPIKRIQ YEIKQIKMFK  GPEK......  IEFIYTAPSS
Mouse TIMP-2   SEKEVDSGND IYGNPIKRIQ YEIKQIKMFK  GPDK      D IEFIYTAPSS
Chick TIMP-3   GKKLMKDG.. .....PFGTMR YTVKQMKMYR  GFQIM...PH VQYIYTEASE
Human TIMP-3   GKKLVKEG.. .....PFGTLV YTIKQMKMYR  GFTKM...PH VQIHTEASE
```

FIG. 4A

```
                66                              ***                                      113
Bovine TIMP-1   SVCGYFHRSQ  NRSEEFLIAG  QLSNGHLHIT  TCSFVAPWNS  MSSAQRRGFT
Human  TIMP-1   SVCGYFHRSH  NRSEEFLIAG  KLQDGLLHIT  TCSFVAPWNS  LSLAQRRGFT
Rabbit TIMP-1   SVCGYSHKSQ  NRSEEFLIAG  QLRNGLLHIT  TCSFVVPWNS  LSFSQRSGFT
Mouse  TIMP-1   SLCGYAHKSQ  NRSEEFLITG  RLRNGNLHIS  ACSFLVPWRT  LSPAQQRAFS
Bovine TIMP-2   AVCGVSLDIG  GKKEYLIAGK  AEGNGNMHIT  LCDFIVPWDT  LSATQKKSLN
Human  TIMP-2   AVCGVSLDVG  GKKEYLIAGK  AEGDGKMHIT  LCDFIVPWDT  LSTTQKKSLN
Mouse  TIMP-2   AVCGVSLDVG  GKKEYLIAGK  AEGDGKMHIT  LCDFIVPWDT  LSITQKKSLN
Chick  TIMP-3   SLCGVKLEV.  NKYQYLITGR  VY.EGKVYTG  LCNWYEKWDR  LTLSQRKGLN
Human  TIMP-3   SLCGLKLEV.  NKYQYLLTGR  VY.DGKMYTG  LCNFVERWDQ  LTLSQRKGLN 114                                                                      162
Bovine TIMP-1   KTYAAGCEEC  TVFPCSSIPC  KLQSDTHCLW  TDQLLTGSDK  GFQSRHLACL
Human  TIMP -1  KTYTVGCEEC  TVFPCLSIPC  KLQSGTHCLW  TDQLLQGSEK  GFQSRHLACL
Rabbit TIMP-1   KTYAAGCDMC  TVFACASIPC  HLESDTHCLW  TDSSL.GSDK  GFQSRHLACL
Mouse  TIMP-1   KTYSAGCGVC  TVFPCLSIPC  KLESDTHCLW  TDQVLVGSE.  DYQSRHFACL
Bovine TIMP-2   HRYQMGCE.C  KITRCPMIPC  YISSPDECLW  MDWVTEKNIN  GHQAKFFACI
Human  TIMP-2   HRYQMGCE.C  KITRCPMIPC  YISSPDECLW  MDWVTEKNIN  GHQAKFFACI
Mouse  TIMP-2   HRYQMGCE C  KITRCPMIPC  YISSPDECLW  MDWVTEKSIN  GHQAKFFACI
Chick  TIMP-3   HRYHLGCG.C  KIRPCYYLPC  FATSKNECIW  TDMLSNFGHS  GHQAKHYACI
Human  TIMP-3   YRYHLGCN.C  KIKSCYYLPC  FVTSKNECLW  TDMLSNFGYP  GYQSKHYACI
```

FIG. 4B

|                | 163        |            | 188    |                    |
|----------------|------------|------------|--------|--------------------|
| Bovine TIMP-1  | PREPGLCTWQ | SLRAQMA... | ...... | (SEQ ID NO:22)     |
| Human TIMP-1   | PREPGLCTWQ | SLRSQIA... | ...... | (SEQ ID NO:23)     |
| Rabbit TIMP-1  | PQEPGLCAWE | SLRPRKD... | ...... | (SEQ ID NO:24)     |
| Mouse TIMP-1   | PRNPGLCTWR | SLGAR..... | ...... | (SEQ ID NO:25)     |
| Bovine TIMP-2  | KRSDGSCAWY | RGAAPPKQEF | LDIEDP | (SEQ ID NO:26)     |
| Human TIMP-2   | KRSDGSCAWY | RGAAPPKQEF | LDIEDP | (SEQ ID NO:27)     |
| Mouse TIMP-2   | KRSDGSCAWY | RGAAPPKQEF | LDIEDP | (SEQ ID NO:28)     |
| Chick TIMP-2   | QRVEGYCSWY | RGWAPPDKTI | INATDP | (SEQ ID NO:29)     |
| Human TIMP-3   | RQKGGYCSWY | RGWAPPDKSI | INATDP | (SEQ ID NO:13)     |

*FIG. 4C*

Amino acid alignment of Timp3 and ChIMP-3

```
TIMP-3    1   MTPWLGLI.VLLGSWSLGDWGAEACTCSPSHPQDAFCNSDIVIRAKVVGK   49
              ||:|||| :|:||:|||:|| |:|||| |.:|||||||||||||||||
ChIMP-3   1   MTAWLGFLAVFLCSWSLRDLVAEACTCVPIGPQDAFCNSDIVIRAKVVGK   50

TIMP-3   50   KLVKEGPFGTLVYTIKQMKMYRGFTKMPHVQYIHTEASESLCGLKLEVNK   99
              ||:|:||||| :|:|||||||| .:|||||||:|||||||||| ||||||
ChIMP-3   51  KLMKDGPFGTMRYTVKQMKMYRGFQIMPHVQYIYTEASESLCGVKLEVNK  100

TIMP-3  100   YQYLLTGRVYDGKMYTGLCNFVERWDQLTLSQRKGLNYRYHLGCNCKIKS  149
              |||||||||| ||||||||:|| |: ||||||||||| |||||||| || 
ChIMP-3  101  YQYLITGRVYEGKVYTGLCNWYEKWDRLTLSQRKGLNHRYHLGCGCKIRP  150

TIMP-3  151   CYYLPCFVTSKNECLWTDMLSNFGYPGYQSKHYACIRQKGGYCSWYRGWA  200
              ||||||| ||||||:|||||||| |..|.:|||||||||| ||||||||
ChIMP-3  150   CYYLPCFATSKNECIWTDMLSNFGHSGHQAKHYACIQRVEGYCSWYRGWA  199

TIMP-3  200   PPDKSIINATDP  211  SEQ ID NO:13
              ||||:|||||||
ChIMP-3  201  PPDKTIINATDP  212  SEQ ID NO:29
```

FIG. 5

Nucleic acid alignment of TIMP-3 and ChIMP-3
Overall homology

```
TIMP-3   151 CGCCGGGAGGCCAAGGTTGCCCCGCACGGCCCCGGCGGGGGCCGAGCTCGG 200
             |||  |  |||  | |    ||   || |||||| |||  |||||||||
ChIMP-3    1 .........CGCGAGAGAGAGGCGGTGTGAGGAGGGAGCGAGCAGCG     42

TIMP-3   201 GCTGCAGCAGCCCCGCCGGCGCGCACGGCAACTTTGGAGAGGCGAGC    250
             ||||||||||| ||||  ||||||| ||  |||  |||| ||| |||
ChIMP-3   43 AACAGGCGAGGCTCGAGTTAGGCGAACAGAACAGCGGCTGCAGCTCGAAG 92

TIMP-3   251 AGCAGCCCCGGCAGCGGCCAGCAGCGGCAATGACCCCTTGGCTCGG..    298
                   ||||||                        |||||||||||
ChIMP-3  393 CGCACCCCGGG.........GCAGGCAGCATGACCGGCGTGGCTCGGCT 131

TIMP-3   299 .GCTCATCGTGCTCCTGGGCAGCTGGAGCCTGGGGGACTGGGCGCCGAG  347
              |||||||||| |||||||   |||||||||||| |||||||||||||
ChIMP-3  132 TCCTCGCCGTGTTCCTGTGCAGCTGGAGCCTGGGAGCCTGGTGGCGGAG 181

TIMP-3   348 GCGTGCACATGCTCGCCCAGCCACCCCCAGGACGCCTTCTGCAACTCCGA 397
             |||||| ||| ||||||    |||| |||||||||| |||||||||||
ChIMP-3  182 GCGTGCACTTGCTCCCCCATCCACCCGAGGACGCGTTGTGCAACTCCGA 231

TIMP-3   398 CATCGTGATCCGGGCCAAGGTGGTGGGGAAGAAGCTGGTAAAGGAGGGGC 447
             |||||||||||| ||||||||||||| ||||||||||||||| || |||
ChIMP-3  232 CATCGTGATCCGTGCTAAAGTTGTGGGGAAGAAGCTCATGAAAGATGGAC 281
```

FIG. 6A

```
TIMP-3   448 CCTTCGGCACGCTGGTCTACACCATCAAGCAGATGAAGATGTACCGAGGC  497
             |||  |  |   ||  ||  |||||||||||||||||||||||| ||||
ChIMP-3  282 CATTTGGAACAATGCGATACACAGTCAAGCAGATGAAGATGTACAGGGGC  331

TIMP-3   498 TTCACCAAGATGCCCCATGTGCAGTACATCCATACGGAAGCTTCCGAGAG  547
             |||  |  |||  |  |||   | |||||| ||||| |||| ||||||
ChIMP-3  332 TTCCAGATAAATGCCACACGTTCAGTACATCTACACAGAAGCCTCAGAGAG  381

TIMP-3   548 TCTCTGTGGCCTTAAGCTGGAGGTCAACAAGTACCAGTACCTGCTGACAG  597
             || |||||| ||| | |||||||||||||| ||||||||| ||||| |
ChIMP-3  382 TCTTTGTGGTGTGAAACTGGAGGTCAACAAATACCAGTATCTGATTACAG  481

TIMP-3   598 GTCGCGTCTATGATGGCAAGATGTACACGGGGCTGTGCAACTTCGTGGAG  647
               ||| || ||||  |||| ||| || |   |||||||| ||||| |||
ChIMP-3  432 GCCGCGTGTACGAAGGGAAGGTTTATACTGGCCTGTGCAATTGGTATGAG  481

TIMP-3   648 AGGTGGGACCAGCTCACCCTCTCCCAGCGCAAGGGGCTGAACTATCGGTA  697
             | || |||||| ||||| ||||||||| |  ||| |||||||| |  ||
ChIMP-3  482 AAATGGGACCGACTGACTCTGTCCCAGCGTAAAGGACTGAATCATCGTTA  531

TIMP-3   698 TCACCTGGGTTGTAACTGCAAGATCAAGTCCTGCTACTACCTGCCTTGCT  747
             ||| |||||  ||| |||||||| |||| | |||||||| ||| |||||
ChIMP-3  532 TCATCTGGGCTGTGTGATGCAAGATTCGGCGCCCTGCTACTATTTGCCCTGCT  581
```

FIG. 6B

```
TIMP-3    748 TTGTGACTTCCAAGAACGAGTGTCTCTGGACCGACATGCTCTCCAATTTC  797
              |||  |||||||||||| |||||  |||||||||||||||||||| |||
ChIMP-3   582 TTGCCACCTCCAAGAATGAGTGCATTTGGACAGACATGCTCTCCAACTTC  631

TIMP-3    798 GGTTACCCTGGCTACCAGTCCAAAACACTACGCCCTGCATCCGGCAGAAGGG  847
              ||  ||| |||| ||||| ||||| ||| |||| |||||||| ||| ||||
ChIMP-3   632 GGCCACTCAGGAGGACACCAAGCGAAGCACTATGCCTGCATCCAGAGGGTGGA  681

TIMP-3    848 CGGCTACTGCAGCTGGTACCGAGGATGGGCCCCCCGGATAAAGCATCA  897
              ||| |||||||||||||| |||||||||||   |||||||||| ||||
ChIMP-3   682 AGGTTACTGCAGCTGGTATAGAGGATGGGCGCCTCCAGATAAAACGATCA  731

TIMP-3    898 TCAATGCCACAGACCCCTGAGCGC..CAGACCCCTGCCCCACCT..CACTTC  944
              ||||||||||||||| |||||| |  |||| |||||| || ||   |||||
ChIMP-3   732 TCAATGCCACAGATCCCTGAGCACGCTGTACCTTCCTTATCTTCCCTCTC  781

TIMP-3    945 CCTCCCCTTCCCGCTGAGCTTCCCTTGGACACTAACTCTTCCC......AG  988
              || | ||| |   ||||| |||| |||||||||||||||| ||      |
ChIMP-3   782 CCTTACTTGTGGCTGATGTTCCTTGGACACTAACTCTTACCCGATCATG  831

TIMP-3    989 ATGATGACAATGAAATTAGTGCCTGTTTTCTTGCAAATT.TAGCACTTGG 1037
              ||||||||||||||||||||||||||||||||||||||| |||||||| |
ChIMP-3   832 ATGATGACAATGAAATTAGTGCCTGTTTTCTTGCAAATTCTAGCACTTCG  881
```

FIG. 6C

TIMP-3  1038  AACATTTAAAGAAAAGGTCTATGCTGTCATATGGGGTTTATTGGGAACTAT  1087  SEQ ID NO:30
                     | | |
ChIMP-3  882  AACCG..............................................  886   SEQ ID NO:31

*FIG. 6D*

Nucleic acid alignment of TIMP-3 and ChIMP-3
Region of maximal homlogy

```
TIMP-3   282 ATGACCCCCTTGGCTCGGGCTCAT...CGTGCTCCTGGGCAGCTGGAGCCT 328
             ||| ||| || ||||| ||||||      |||||||||||||||||||||||
ChIMP-3  113 ATGACGGGCGTGGCTCGGGCTTCCTGGCCGTGTTCCTGTGCAGCTGGAGCCT 162

TIMP-3   329 GGGGGACTGGGGCGCCGAGGCCGTGCACATGCTCGCCCAGCCACCCCCAGG 378
             ||||||||||||| |||||||||||||||||||| ||||||| ||  ||||
ChIMP-3  163 GCGGGACCTGGTGGGGGAGGCCGTGCACTTGCGTCCCCCATCCACCCGCAGG 212

TIMP-3   379 ACGCCTTCTGCAACTCCGACATCGTGATCCGGGCCAAGGTGGTGGGGAAG 428
             ||||| || |||||||||||||||||||||| | ||||||||| |||||||
ChIMP-3  213 ACGCGTTGTGTGCAACTCCGACATCGTGATCCGTGCTAAAGTTGTGGGGAAG 262

TIMP-3   429 AAGCTGGTAAAGGAGGGGCCCTTCGGCACGCTGGTCTACACCATCAAGCA 478
             ||||||| || |||||| |||||||||||| ||| ||||||| |||||||
ChIMP-3  263 AAGCTCATGAAAGATGGACCATTTGGAACAATGCGATACACAGTCAAGCA 312

TIMP-3   479 GATGAAGATGTACCGAGGCTTCACCAAGATGCCCCATGTGCAGTACATCC 528
             |||||||||||| ||||||||||||| ||||| || ||||||||||| ||
ChIMP-3  313 GATGAAGATGTACAGGGGCTTCCAGATAATGCCACACGTTCAGTACATCT 362

TIMP-3   529 ATACGGAAGCTTCCGAGAGTCTCTGTGGCCTTAAGCTGGAGGTCAACAAG 578
             | ||| ||||| || ||||| ||||||| |   |||||||||||||||||
ChIMP-3  363 ACACAGAAGCCTCAGAGAGTCTTTGTGGTGTGAAACTGGAGGTCAACAAA 412
```

*FIG. 7A*

```
TIMP-3   579 TACCAGTACCTGCTGCTGACAGGTCGCGTCTATGATGGCAAGATGTACACGGG 628
             ||||||||||||||| ||  ||||  || |||||||| ||||||| |||||
ChIMP-3  413 TACCAGTATCTGATTACAGGCCGCGTGTACGAAGGGAAGGTTTATACTGG   462

TIMP-3   629 GCTGTGCAACTTCGTGGAGAGGTGGGACCAGCTCACCCTCTCCCAGCGCA   678
             |||||||||| | ||||| |||||||  |||| | |||  |||||| ||
ChIMP-3  463 CCTGTGCAATTGGTATGAGAAAATGGGACCGACTCTGTCCCAGCGTA     512

TIMP-3   679 AGGGGCTGAACTATCACCTGGGTTGTAACTGCAAGATCAAGTCC        728
             || |||||||||| ||  |||| ||||||||||||| ||| ||
ChIMP-3  513 AAGGACTGAATCATCGTTATCATCTGGGCTGTGGATGCAAGATTCGGCCC  562

TIMP-3   729 TGCTACTACCTGCCTTGCTTTGTGACTTCCAAGAACGAGTGTCTCTGGAC  778
              ||||||| ||||| ||||  |||   || | ||| ||||  |||||||
ChIMP-3  563 TGCTACTATTTGCCCCTGCTTTGCCACCTCCAAGAATGAGTGCATTTGGAC 612

TIMP-3   779 CGACATGCTCTCCAATTTCGGTTACCCTGGCTACCCAGTCCAAACACTACG 828
             | |||| || |||||| |||| || ||||||||| ||||||| || ||||
ChIMP-3  613 AGACATGCTCTCCAACTTCGGCCACTCAGGACACCAAGGAAGCACTATG   662

TIMP-3   829 CCTGCATCCGGCAGAAGGGCGGCTACTGCAGCTGGTACCGAGGATGGGCC  878
             |||||||||||||  |||| ||||||||||||| |||  |||||||||
ChIMP-3  663 CCTGCATCCAGAGGGTGGAAGTTACTGCAGCTGGTATAGAGGATGGGCG   712
```

*FIG. 7B*

```
TIMP-3    879 CCCCCGGATAAAAGCATCATCAATGCCACAGACCCCTGAGCGC.CAGACC  927
              ||  ||||||||||  ||| |||||||||||||||||||||||| ||| ||
ChIMP-3   713 CCTCCAGATAAAAGGATCATCAATGCCACAGATCCCTGAGCACGCTGTAC  762

TIMP-3    928 CTGCCCCACCT..CACTTCCCCTTCCCGCTGAGCTTCCCTGGACAC      975
              ||  ||| |||  ||||||  ||  |||   |||||| |||||||
ChIMP-3   763 CTTCCCTTATCTTCCCCTCCCCTTACTTGTGGCTGATGTTCCTTTGGACAC  812

TIMP-3    976 TAACTCTTCCC......AGATGATGACAATGAAATTAGTGCCTGTTTTCT 1019
              |||||||| |||     |||||||||||||||||||||||||||||||||
ChIMP-3   813 TAACTCTTACCCGATCATGATGATGACAATGAAATTAGTGCCTGTTTTCT  862

TIMP-3   1020 TGCAAAATT.TAGCACTTGGAAC 1040 SEQ ID NO: 30
              ||||||||| |||||||| ||||
ChIMP-3   863 TGCAAATTCTAGCACTTCGAAC   884 SEQ ID NO: 31
```

*FIG. 7C*

Amino acid alignment of human TIMP-3 and human TIMP-2

```
TIMP-3    1                   MTPWLGLIVLLGSWSLGDWGAEACTCSPSHPQDAFCNSDIVIRAK  45
                              .|:|::||  .| :|:||  |||.|||::|||::|:|||
TIMP-2    1   MGAAARTLRLALGLLLLATLL..RPADACSCSPVHPQQAFCNADVVIRAK  48

TIMP-3   46   VVGKKLVKEG......PFGTLVYTIKQMKMYRGFTKMPHVQYIHTEASES  89
              .|::|.|.|       :|  |: |.|:|||:::::|:|  :||::::
TIMP-2   49   AVSEKEVDSGNDIYGNPIKRIQYEIKQIKMFKGPEK..DIEFIYTAPSSA  96

TIMP-3   90   LCGLKLEV.NKYQYLLTGRVY.DGKMYTGLCNFVERWDQLTLSQRKGLNY 137
              :||:||:|. |: : |:|:.  ||||  |||| ::||||:|: ||.||.
TIMP-2   97   VCGVSLDVGGKKEYLIAGKAEGDGKMHITLCDFIVPWDTLSTTQKKSLNH 146

TIMP-3  138   RYHLGCNCKIKSCYYLPCFVTSKNECLWTDMLSNFGYPGYQSKHYACIRQ 187
              ||:||| ||| ||:||||:|:.|:|||  |: :|:||||| |||.|||:
TIMP-2  147   RYQMGCECKITRCPMIPCYISSPDECLWMDWVTEKNINGHQAKFFACIKR 196

TIMP-3  188   KGGYCSWYRGWAPPDKSIINATDP 211 SEQ ID NO: 13
              .| |||||||.|||.:. .:: .||
TIMP-2  197   SDGSCAWYRGAAPPKQEFLDIEDP 220 SEQ ID NO: 27
```

FIG. 8

NUCLEIC ACID ALIGNMENT OF TIMP-3 AND TIMP-2
OVERALL HOMOLOGY

```
TIMP-3    1  GGGGGGGGGGCGCTCAGAGGGCTTCCTCCTCCTCTTGCTCCTCCAAGCT  50
TIMP-2    1  ......GGGGGCCGCCGAGAGCCGCAGCGCCGCTCGCCCCGCGCCCCACC  45
TIMP-3   51  CCTGCTCCTTCGCCCGGGAGCCCGGAGTCCTGCGCCAGCGCCGAG      100
TIMP-2   46  CCGCCGCCCCGCCCCGGCGAATTGCGCCCCCGCCCCCCCTCGCGCCCCC   95
TIMP-3  101  GCAGCCTCGCTGCGCCCCATCCCGTCCCGCGGGCACTCGGAGGGCAGCG  150
TIMP-2   96  GAGACAAAGAGGAGAGAAAGTTTGCGCCCCGAGCGGGGCAGGTGAGGAGG 145
TIMP-3  151  CGCCGGAGGCCAAGGTTGCCCCGCACGCCCGGCGGGCGAGCGAGCTCGG  200
TIMP-2  146  GTGAGCCGGCGGCGGGAGGGCCCGCTCGGCCCCGCTCAGCCCCGCCCGC  195
TIMP-3  201  GCTGCAGCAGCCCCGCCG.GCGGGCGCGCACGGCAACTTTGGAGAGG....  245
TIMP-2  196  GCCCCCAGCCCGCCGCGAGCAGCCCGGACCCCCAGCGGGGCCC         245
```

*FIG. 9A*

| | | | | |
|---|---|---|---|---|
| TIMP-3 | 246 | .....CGAGCAGCAGCCCCGGCAGCGGGCAGCGGGCAATGACCCCTT | 291 |
| TIMP-2 | 246 | CGCCCGCCCCAGCCCCCGGCCCCGCCATGGGCGCCCGGCCCGCACCCTGC | 295 |
| TIMP-3 | 292 | GGCTCGGGCTCATCGTGCTCCTGGGCAGCTGGAGCCTGGGGACTGGGGC | 341 |
| TIMP-2 | 296 | GGCTGGGCGCTCGGCCTCCTGCTG......CTGGGCGACGCTGCTTCGCCCG | 339 |
| TIMP-3 | 342 | GCCGAGGGCGTGCACATGCTCGCCCCAGCCACCCCCAGAGACGCCTTCTGCAA | 391 |
| TIMP-2 | 340 | GCCGACGCCTGCAGCTGCTCCCCGGTGCACCCGCAACAGGGGTTTTGCAA | 389 |
| TIMP-3 | 392 | CTCCGACATCGTGATCCGGGCCAAGTGTGGGGAAGAAGCTGGTAAAGG | 441 |
| TIMP-2 | 390 | TGCAGATGTAGTGATCAGGGCCAAAGCGGTCAGTGAGAAGGAAGTGGACT | 439 |
| TIMP-3 | 442 | AGGG..........GCCCCTTCGGCACGCTGGTCTACACCATC | 473 |
| TIMP-2 | 440 | CTGGAAACGACATTTATGGCAACCCTATCAAGAGGATCCAGTATGAGATC | 489 |

FIG. 9B

| | | | |
|---|---|---|---|
| TIMP-3 | 474 | AAGCAGATGAAGATGTACCGAGGCTTCACCAAGATGCCCATGTGCAGTA | 523 |
| TIMP-2 | 490 | AAGCAGATAAAGATGTTCAAAGGGCCTGAGAAG......GATATAGAGTT | 533 |
| TIMP-3 | 524 | CATCCATACGGAAGCTTCCGAGAGTCTCTGTGGCCTTAAGCTGGAGGT.. | 571 |
| TIMP-2 | 534 | TATCTACACGGCCCCCTCCTCGGCAGTGTGTGGGGTCTCGCTGGACGTTG | 583 |

*FIG. 9C*

| | | | |
|---|---|---|---|
| TIMP-3 | 572 | .CAACAAGTACCAGTAGTACCTGCTGACAGGTCGCGTCTATG...ATGGCAAG | 617 |
| TIMP-2 | 584 | GAGGAAAGAAGGAATATCTCATTGCAGGAAAGGCCGAGGGGACGGCAAG | 633 |
| TIMP-3 | 618 | ATGTACACGGGGCTGTGCAACTTCGTGTGGAGAGGTGGGACCAGCTCACCCT | 667 |
| TIMP-2 | 634 | ATGCACATCACCCTCTGTGACTTCATCGTGTGCCCTGGACACCCCTGAGCAC | 683 |
| TIMP-3 | 668 | CTCCCCAGCGCAAGGGGCTGAACTATCGGTATCACCTGGGTTGTAACTGCA | 717 |
| TIMP-2 | 684 | CACCCAGAAGAGAGCCTGAACCACAGTACCAGATGGGCTGCGAGTGCA | 733 |
| TIMP-3 | 718 | AGATCAAGTCCTGCTACTACCTGCCTTGCTTTGTGACTTCCAAGAACGAG | 767 |
| TIMP-2 | 734 | AGATCACGCGCTGCCCCATGATCCCGTGCTACATCTCCTCCCCGGACGAG | 783 |
| TIMP-3 | 768 | TGTCTCTGGACCGACATGCTCTCCAATTTCGGTTACCCTGGCTACCAGTC | 817 |
| TIMP-2 | 784 | TGCCTCTGGACTGACTGGGTCACAGAGAAGAACATCAACGGGCACCAGGC | 833 |

FIG. 9D

| | | | |
|---|---|---|---|
| TIMP-3 | 818 | CAAACACTACGCCTGCATCCGGCAGAAGGGCGGCTACTGCAGCTGGTACC | 867 |
| TIMP-2 | 834 | CAAGTTCTTCGCCTGCATCAAGAGAAGTGACGGCTCCTGTGCGTGGTACC | 883 |
| TIMP-3 | 868 | GAGGATGGGCCCCCCGGATAAAAGCATCATCAATGCCACAGACCCCTGA | 917 |
| TIMP-2 | 884 | GCGGGCGGGGCCCCCAAGCAGGAGTTTCTCGACATCGAGGACCCATAA | 933 |
| TIMP-3 | 918 | GCGCCAGACCCTGCCCCACCTCACTTCCCCTCCCCTTCCCGCTGAGCTTCCC | 967 |
| TIMP-2 | 934 | GCAGGCCTCCAACGCCCCTGTGGCCAACTGCAAAAAAAGCCTCCAAGGT | 983 |
| TIMP-3 | 968 | TTGGACACTAACTCTTCCCAGATGATGACAATGAAATTAGTGCCTGTTTT | 1017 |
| TIMP-2 | 984 | TTCGACTGGTCCAGCTCTGACATCCCCTTCCTGGAAA......CAGCATGA | 1027 |
| TIMP-3 | 1018 | CTTGCAAATTAGCACTTGGAACATTTAAAGAAAGGTCTATGCTGTCATA | 1067 SEQ ID NO: 32 |
| TIMP-2 | 1028 | ATAAAACACTCATCCCATGGTCCAAATTAATATG............ | 1062 SEQ ID NO: 33 |

*FIG. 9E*

NUCLEIC ACID ALIGNMENT OF TIMP-3 AND TIMP-2
REGION OF MAXIMAL HOMOLOGY

```
TIMP-3  208  CAGCCCCGCCGGGGCGCACGGCAACTTTGGAGAGGCGAGCAGCAGCC              257
TIMP-2  225  CGGACCCCCCAGCGGGCCCCGCC..........CGCCCAGCCCCC                261
TIMP-3  258  CCGGCAGGGCGGCAGCAGCGGCAATGACCCCTTGGCTCGGGCTCATCGT            307
TIMP-2  262  CGGCCCGCCATGGGCGCCCGGCCACCCTGCGGCTGGCGCTGGCCT                311
TIMP-3  308  GCTCCTGGGCAGCTGGAGCCTGCTTCGCCCG.GCCGACGCCCTGCAGCT            357
TIMP-2  312  CCT......GCTGCTGGCGACGCTGCTTCGCCCG.GCCGACGCCCTGCAGCT         355
TIMP-3  358  GCTGCGCCAGCCACCCCCAGGACGCCTTCTGCAACTCCGACATCGTGATC           407
TIMP-2  356  GCTCCCCGGTGCACCCGCAACAGGCGTTTGCAATGCAGATGTAGTGATC            405
TIMP-3  408  CGGGCCAAGGTGGTGGGGAAGAAG...........CTGGTAA........A         439
TIMP-2  406  AGGGCCAAAGCGGTCAGTGAGAAGGAAGTGGACTCTGGAAACGACATTTA           455
```

FIG. 10A

| | | |
|---|---|---|
| TIMP-3 | 440 | GGAGGGGCCCTTCGGCACGCTGGTCTACACCATCAAGCAGATGAAGATGT 489 |
| TIMP-2 | 456 | TGGCAACCCTATCAAGAGGATCCAGTATGAGATCAAGCAGATAAAGATGT 505 |
| TIMP-3 | 490 | ACCGAGGCTTCACCAAGATGCCCCATGTGCAGTACATCCATACGGAAGCT 539 |
| TIMP-2 | 506 | TCAAAGGGCCTGAGAAG......GATATAGAGTTTATCTACACGGCCCC 549 |
| TIMP-3 | 540 | TCCGAGAGTCTCTGTGGCCTTAAGCTGGAGGT...CAACAAGTACCAGTA 586 |
| TIMP-2 | 550 | TCCTCGGCAGTGTGTGGGGTCTCGCTGGACGTTGGAGGAAAGAAGGAATA 599 |
| TIMP-3 | 587 | CCTGCTGACAGGTCGCGTCTA...TGATGGCAAGATGTACACGGGGCTGT 633 |
| TIMP-2 | 600 | TCTCATTGCAGGAAAGGCCGAGGGGGACGGCAAGATGCACATCACCCTCT 649 |
| TIMP-3 | 634 | GCAACTTCGTGGAGAGGTGGGACCAGCTCACCCTCTCCCAGCGCAAGGGG 683 |
| TIMP-2 | 650 | GTGACTTCATCGTGCCCTGGGACACCCTGAGCACCCAGAAGAAGAGC 699 |
| TIMP-3 | 684 | CTGAACTATCGGTATCACCTGGGTTGTAACTGCAAGATCAAGTCCTGCTA 733 |
| TIMP-2 | 700 | CTGAACCACAGGTACCAGATGGGCTGCGAGTGCAAGATCACGCGCTGCCC 749 |

FIG. 10B

| | | | |
|---|---|---|---|
| TIMP-3 | 734 | CTACCTGCCTTGCTTTGTGACTTCCAAGAACGAGTGTCTCTGGACCGACA | 783 |
| TIMP-2 | 750 | CATGATCCCGTGCTACATCTCCTCCCCGGACGAGTGCCTCTGGATGGACT | 799 |
| TIMP-3 | 784 | TGCTCTCCAATTTCGGTTACCCTGGCTACCAGTCCAAACACTACGCCTGC | 833 |
| TIMP-2 | 800 | GGGTCACAGAGAAGAACATCAACGGGCACCAGGCCAAGTTCTTCGCCTGC | 849 |
| TIMP-3 | 834 | ATCCGGCAGAAGGGGGCTACTGCAGCTGGTACCGAGGATGGGCCCCCC | 883 SEQ ID NO: 32 |
| TIMP-2 | 850 | ATCAAGAGAAGTGACGGCTCCTGTGCCTGGTACCGCGGCGGCGCCCCC | 899 SEQ ID NO: 33 |

*FIG. 10C*

AMINO ACID ALIGNMENT OF HUMAN TIMP-3
AND HUMAN TIMP-1

```
TIMP-1    1  MAPFEPLASGILLLLWLIAPSR...ACTCVPPHPQTAFCNSDLVIRAKFV            47
TIMP-3    1  MTPWLGL...IVLLGWSLGDWGAEACTCSPSHPQDAFCNSDIVIRAKVV            47

TIMP-1   48  GTPEVNQTTL.YQRYEIKMTKMYKGFQALGDAADIRFVYTPAMESVCGYF           96
TIMP-3   48  GKKLVKEGPFGTLVYTIKQMKMYRGFTKM...PHVQYIHTEASESLCGL.           93

TIMP-1   97  HRSHNRSEEFLIAGKLQDGLLHITTCSFVAPWNSLSLAQRRGFTKTYTVG          146
TIMP-3   94  .KLEVNKYQYLLTGRVYDGKMYTGLCNFVERWDQLTLSQRKGLNYRYHLG          142

TIMP-1  147  CEECTVFPCLSIPCKLQSGTHCLWTDQLLQGSEKGFQSRHLACLPREPGL          196
TIMP-3  143  C.NCKIKSCYLPCFVTSKNECLWTDMLSNFGYPGYQSKHYACIRQKGGY          191

TIMP-1  197  CTWQSLRSQIA........  207 SEQ ID NO: 23
TIMP-3  192  CSWYRGWAPPDKSIINATDP  211 SEQ ID NO: 13
```

FIG. 11

NUCLEIC ACID ALIGNMENT OF TIMP-3 AND TIMP-1
OVERALL HOMOLOGY

```
TIMP-3  201  GCTGCAGCAGCCCCGCCGGGGCGGCGCAGGCAACTTTGGAGAGGCGAGC  250
TIMP-1    1  ................................AGGGGCCTTAGCGTGCCGCATCGCCGAGATC   31
TIMP-3  251  AGCAGCCCCGGCAGCGGGGCGCAGCAGCGGCAATGACCCCTTGGCTCGGGC  300
TIMP-1   32  CAGGCGCCCAGAGAGACACCAGAGAACCCACCATGGCCCCCTTTGAGCCCC   81
TIMP-3  301  TCATCGTGCTCCTGGGCAGCTGGAGCCTGGGGCGCCGAGGCG  350
TIMP-1   82  TGGCTTCTGGCATCCTGTTGTTGCTGTGGCTGATAGCCCCCAGCAGGCC  131
TIMP-3  351  TGCACATGCTCGCCCAGCCACCCCCAGGACGCCTTCTGCAACTCCGACAT  400
TIMP-1  132  TGCACCTGTGTCCCACCCCACCCCACAGACGGCCTTCTGCAATTCCGACCT  181
```

*FIG. 12A*

```
TIMP-3  401  CGTGATCCGGGCCAAGGTGGTGGGGAAGAAGCTGGTAAAGGAGGGCCCT  450
TIMP-1  182  CGTCATCAGGGCCAAGTTCGTGGGACACCAGAAGTCAACCAGACCACCT  231
TIMP-3  451  TCGGCACGC......TGGTCTACACCATCAAGCAGATGAAGATGTACCGA  494
TIMP-1  232  TATACCAGCGTTATGAGATCAAGATGACCAAGATGTATAAAGGGTTCCAA  281
TIMP-3  495  GGCTTCACCAAGATGCCCCATGTGCAGTACATCCATACGGAAGCTTCCGA  544
TIMP-1  282  GCCTTAGGGGATGCCGCTGACATCCGGTTCGTCTACACCCCGCCATGGA   331
TIMP-3  545  GAGTCTCTGTGG......CCTTAAGCTGGAGGTCAACAAGTACCAGTACC  588
TIMP-1  332  GAGTGTCTGCGGATACTTCCACAGTCCCACAACCGCAGCGAGGAGTTTC   381
TIMP-3  589  TGCTGACAGGTCGCGTCTATGATGGCAAGATGTACACGGGGCTGTGCAAC  638
TIMP-1  382  TCATTGCTGGAAAACTGCAGGATGGACTCTTGCACATCACTACCTGCAGT  431
```

*FIG. 12B*

| | | | |
|---|---|---|---|
| TIMP-3 | 639 | TTCGTGGAGAGGTGGGACCAGCTCACCCTCTCCCAGCGCAAGGGGCTGAA | 688 |
| TIMP-1 | 432 | TTCGTGGCTCCCTGGAACAGCCTGAGCTTAGCTCAGCGCCGGGGCTTCAC | 481 |
| TIMP-3 | 689 | CTATCGGTATCACCTGGGTTGT...AACTGCAAGATCAAGTCCTGCTACT | 735 |
| TIMP-1 | 482 | CAAGACCTACACTGTTGGCTGTGAGGAATGCACACTGTGTTTCCCTGTTTAT | 531 |
| TIMP-3 | 736 | ACCTGCCTTGCTTTGTGACTTCCAAGAACGAGTGTCTGGACCGACATG | 785 |
| TIMP-1 | 532 | CCATCCCCCTGCAAACTGCAGAGTGGCACTCATTGCTTGTGGACGGACCAG | 581 |

*FIG. 12C*

```
TIMP-3   786  CTCTCCAATTTCGGTTACCCTGGCTACCAGTCCAAACACTACGCCTGCAT  835
TIMP-1   582  CTCCTCCAAGGCTCTGAAAAGGGCTTCCAGTCCCGTCACCTTGCCTGCCT  631
TIMP-3   836  CCGGCAGAAGGGCGGCTACTGCAGCTGGTACCGAGGATGGGCCCCCCCGG  885
TIMP-1   632  GCCTCGGGAGCCAGGGCTGTGCACCTGGCAGTCCCTGCGGTCCCAGATAG  681
TIMP-3   886  ATAAAAGCATCATCAATGCCACAGACCCCCTGAGCGCCAGACCCTGCCCA  935
TIMP-1   682  CCTGAATCCTGCCCGGAGTGGAA......CTGAAGCCTGCACAGTGTCCAC  726
TIMP-3   936  CCTCACTTCCCCTCCCCGCTGAGCTTCCCTTGGACACTAACTCTTCC     985
TIMP-1   727  CCTGTTCCCACTCCCATCTTTCTTCCGGACAATGAAATAAGAGTTACCA   776
TIMP-3   986  CAGATGATGACAATGAAATTAGTGCCTGTTTTCTTGCAAATTTAGCACTT  1035 SEQ ID NO: 34
TIMP-1   777  CCCAGC......                                        782  SEQ ID NO: 35
```

*FIG. 12D*

Nucleic acid alignment of TIMP-3 and TIMP-1
Region of maximal homlogy

```
TIMP-3  347 GGCGTGCACATGCTCGCCCAGCCACCCCCAGGACGCCTTCTGCAACTCCG 396
            ||| ||||| || || |||||| ||||||||||| ||||||||| ||||
TIMP-1  128 GGCCTGCACCTGTCCCACCCCACAGACGGCCTTCTGCAATTCCG 177

TIMP-3  397 ACATCGTGATCCGGGCCAAGGTGGTGGGGAAGAAGCTGGTAAAGGAGGGG 446
             ||||||| || ||| ||||| |||| |||| ||| ||||| || ||
TIMP-1  178 ACCTCGTCATCAGGGCCAAGTTCGTGGGGACACCAGAAGTCAACCAGACC 227

TIMP-3  447 CCCTTCGGCACGCTGGTCTACACCATCAAGCAGATGAAGATGTACCGAGG 496
            ||||||||| ||  |           || ||| ||||||||| |   ||
TIMP-1  228 ACCTTATAC.....CAGCGTTATGAGATCAAGATGACCAAGATGTATAAAGG 274

TIMP-3  497 CTTC 500  SEQ ID NO: 34
            |||
TIMP-1  275 GTTC 278  SEQ ID NO: 35
```

FIG. 13

Nucleotide Sequences Of TIMP-3 Clones and Predicted Amino Acid Sequence(s)

```
TIMP3Clone7    GGCGGGGGGCGCTCAGACGGCTTCTCCTCCTTGCTCCTCCAAGCTCCTGCTCCTT    60
TIMP3Clone2    ......................................................
TIMP3HCM-3     ......................................................
TIMP3PCR29     ......................................................

TIMP3Clone7    CGCCGGGAGCCCGCCCGGCCCCGAGTCCTGCGCCAGCCTCGCTGCCCCAT         120
TIMP3Clone2    ..........................................................
TIMP3HCM-3     ..........................................................
TIMP3PCR29     ..........................................................

TIMP3Clone7    CCCGTCCCCGCGGGCACTCGGAGGCGCAGGGCAGGCCAAGTTGCCCCGCACGGCC    180
TIMP3Clone2    ......................................................
TIMP3HCM-3     ......................................................
TIMP3PCR29     ......................................................

TIMP3Clone7    CGGCGGGCGGAGCGAGCTCGGCTGCAGCAGCCCGCGGGCGCACGGCAACTTTGG    240
TIMP3Clone2    ......................................................
TIMP3HCM-3     ......................................................
TIMP3PCR29     ......................................................
```

FIG. 16A

```
                                                        MetThrProTrpLeuGlyL         -16
TIMP3Clone7     AGAGGCGAGCAGCAGCCCCGGGCAGCAGGGGCGGCAATGACCCCTTGGCTCGGGC  300
TIMP3Clone2     .......................................................
TIMP3HCM-3      .......................................................
TIMP3PCR29      .......................................................

euIleValLeuLeuGlySerLeuGlyAspTrpGlyAlaGluAlaCysThrCysS    5
TIMP3Clone7     TCATCGTGCTCCTGGGCAGCCTGGGGGACTGGGGGGCCGAGGCGTGCACATGCT  360
TIMP3Clone2                                        ||||||||||||||||||||
                                                   CAGGAGCCTGGGGGACTGGGGGGCCGAGGCGTGCACATGCT
                                                   Arg SEQ ID NO: 15
TIMP3HCM-3      .......................................................
TIMP3PCR29      .......................................................

erProSerHisProGlnAspAlaPheCysAsnSerAspIleValIleArgAlaAlaLysValV  25
TIMP3Clone7     CGCCCAGCCACCCCCAGGACGCCTTCTGCAACTCCGACATCGTGATCCGGGCCAAGGTGG  420
TIMP3Clone2     ||||||||||||||||||||||||||||||||||||||||||||||||||||||||||||
                CGCCCAGCCACCCCCAGGACGCCTTCTGCAACTCCGACATCGTGATCCGGGCCAAGGTGG  100
TIMP3HCM-3      ............................................................
TIMP3PCR29      ............................................................
```

*FIG. 16B*

```
                        alGlyLysLysLeuValLysGluGlyProPheGlyThrLeuValTyrThrIleLysGlnM   45
TIMP3Clone7   TGGGGAAGAAGCTGGTAAAGGAGGGGCCCTTCGGCACGCTGGTCTACACCATCAAGCAGA  480
              ||||||||||||||||||||||||||||||||||||||||||||||||||||||||||||
TIMP3Clone2   TGGGGAAGAAGCTGGTAAAGGAGGGGCCCTTCGGCACGCTGGTCTACACCATCAAGCAGA  160
              ||||||||||||||||||||||||||||||||||||||||||||||||||||||||||||
TIMP3HCM-3    ..GGGAAGAAGCTGGTAAAGGAGGGGCCCTTCGGCACGCTGGTCTACACCATCAAGCAGA   58
TIMP3PCR29    ............................................................
```

```
                 lnLysGlyGlyTyrCysSerTrpTyrArgGlyTrpAlaProProAspLysSerIleIleA
TIMP3clone7      AGAAGGGCGGCTACTGCAGCTGGTACCGAGGATGGGCCCCCCGGATAAAAGCATCATCA    185
                 ||||||||||||||||||||||||||||||||||||||||||||||||||||||||||    900
TIMP3clone2      AGAAGGGCGGCTACTGCAGCTGGTACCGAGGATGGGCCCCCCGGATAAAAGCATCATCA    580
                 ||||||||||||||||||||||||||||||||||||||||||||||||||||||||||    478
TIMP3HCM-3       AGAAGGGCGGCTACTGCAGCTGGTACCGAGGATGGGCCCCCCGGATAAAAGCATCATCA
                 |     |   |                                                    130
TIMP3PCR29       GCCACCCCCGCACGCGCTCCCG......                SEQ ID NO:19 erHisProArgThrArg       SEQ ID NO:13
                 snAlaThrAspProEnd
TIMP3clone7      ATGCCACAGACCCCCTGAGCGCCAGAGCCCTGCCCCACCCTCACTTCCCCTCCCGCTGA    960
                 ||||||||||||||||||||||||||||||||||||||||||||||||||||||||||    640
TIMP3clone2      ATGCCACAGACCCCCTGAGCGCCAGAGCCCTGCCCCACCCTCACTTCCCCTCCCGCTGA    538
                 ||||||||||||||||||||||||||||||||||||||||||||||||||||||||||    190
TIMP3HCM-3       ATGCCACAGACCCCCTGAGCGCCAGAGCCCTGCCCCACCCTCACTTCCCCTCCCGCTGA
TIMP3PCR29       ......
TIMP3clone7      GCTTCCCCTTGGACACTAACTCTTCCCAGATGATGACAATGAAATTAGTGCCTGTTTCTT   1020
                 ||||||||||||||||||||||||||||||||||||||||||||||||||||||||||    700
TIMP3clone2      GCTTCCCCTTGGACACTAACTCTTCCCAGATGATGACAATGAAATTAGTGCCTGTTTCTT    598
                 ||||||||||||||||||||||||||||||||||||||||||||||||||||||||||    250
TIMP3HCM-3       GCTTCCCCTTGGACACTAACTCTTCCCAGATGATGACAATGAAATTAGTGCCTGTTTCTT
TIMP3PCR29       ......
```

*FIG. 16F*

```
TIMP3clone7    GCAAATTTAGCACTTGGAACATTTAAAGAAAAGGTCTCTATGCTGTCATATGGGGTTTATTGG   1080
               ||||||||||||||||||||||||||||||||||||||||||||||||||||||||||||||||
TIMP3clone2    GCAAATTTAGCAGTTGGAACATTTAAAGAAAAGGTCTCTATGCTGTCATATGGGGTTTATTGG   760
               ||||||||||||||||||||||||||||||||||||||||||||||||||||||||||||||||
TIMP3HCM-3     GCAAATTTAGCACTTGGAACATTTAAAGAAAAGGTCTCTATGCTGTCATATGGGGTTTATTGG   658
TIMP3PCR29     ..............................................................   310

TIMP3clone7    GAACTATCCTCCTGGCCCCCACCCCTGCCCCCTTCTCTTTTTGGTTTTTGACATTCATTTCCA   1140
               ||||||||||||||||||||||||||||||||||||||||||||||||||||||||||||||||
TIMP3clone2    GAACTATCCTCCTGGCCCCCACCCCTGCCCCCTTCTCTTTTTGGTTTTTGACATTCATTTCCA   820
               ||||||||||||||||||||||||||||||||||||||||||||||||||||||||||||||||
TIMP3HCM-3     GAACTATCCTCCTGGCCCCCACCCCTGCCCCCTTCTCTTTTTGGTTTTTGACATTCATTTCCA   718
TIMP3PCR29     ..............................................................   370

TIMP3clone7    CCTGGGAATTTCTGGTGCCATGCCAGAAGAATGAGGAACCTGTATTCCTCTTCTTCGTG   1200
               |||||||||||||||||||||||||||||||||||||||||||||||||||||||||||
TIMP3clone2    CCTGGGAATTTCTGGTGCCATGCCAGAAGAATGAGGAACCTGTATTCCTCTTCTTCGTG   880
               |||||||||||||||||||||||||||||||||||||||||||||||||||||||||||
TIMP3HCM-3     CCTGGGAATTTCTGGTGCCATGCCAGAAGAATGAGGAACCTGTATTCCTCTTCTTCGTG   778
TIMP3PCR29     ...........................................................   430
```

*FIG. 16G*

```
TIMP3clone7   ATAATATATAATCTCTATTTTTTTAGGAAAAAAAAAAAAA..............   1260
              ||||||||||||||||||||||||||||||||   |||  |||
TIMP3clone2   ATAATATATAATCTCTATTTTTTTAGGAAAACAAAAATGAAAAACTACTCCATTTGAGGATT   940
              ||||||||||||||||||||||||||||||   |||  |||||
TIMP3HCM-3    ATAATATATAATCTCTATTTTTTTAGAAAAAAAAAAAAAA..............   838
                                                                              490

TIMP3clone7   ..............................................   1282    SEQ ID NO: 12
TIMP3clone2   GTAATTCCCAACACCACCCTGCT.......................    962    SEQ ID NO: 14
TIMP3HCM-3    ..............................................    860    SEQ ID NO: 16
TIMP3PCR29    ..............................................    512    SEQ ID NO: 18
```

*FIG. 16H*

```
                              SEQUENCE LISTING (1) GENERAL INFORMATION:

(iii) NUMBER OF SEQUENCES: 42

(2) INFORMATION FOR SEQ ID NO: 1:

(i) SEQUENCE CHARACTERISTICS:
             (A) LENGTH: 19 base pairs
             (B) TYPE: nucleic acid
             (C) STRANDEDNESS: single
             (D) TOPOLOGY: linear (ii) MOLECULE TYPE: cDNA (xi) SEQUENCE DESCRIPTION: SEQ ID NO: 1:

CGGAATTCGT NATHMGNGC                                                    19

(2) INFORMATION FOR SEQ ID NO: 2:

(i) SEQUENCE CHARACTERISTICS:
             (A) LENGTH: 26 base pairs
             (B) TYPE: nucleic acid
             (C) STRANDEDNESS: single
             (D) TOPOLOGY: linear (ii) MOLECULE TYPE: DNA (genomic)

(xi) SEQUENCE DESCRIPTION: SEQ ID NO: 2:

CGGGATCCCA TRTCNGTCCA DATRCA                                            26

(2) INFORMATION FOR SEQ ID NO: 3:

(i) SEQUENCE CHARACTERISTICS:
             (A) LENGTH: 23 base pairs
             (B) TYPE: nucleic acid
             (C) STRANDEDNESS: single
             (D) TOPOLOGY: linear (ii) MOLECULE TYPE: DNA (genomic)

(xi) SEQUENCE DESCRIPTION: SEQ ID NO: 3:

CGGGATCCRT CNGTCCADAT RCA                                               23

(2) INFORMATION FOR SEQ ID NO: 4:

(i) SEQUENCE CHARACTERISTICS:
             (A) LENGTH: 18 base pairs
             (B) TYPE: nucleic acid
             (C) STRANDEDNESS: single
             (D) TOPOLOGY: linear (ii) MOLECULE TYPE: DNA (genomic)

(xi) SEQUENCE DESCRIPTION: SEQ ID NO: 4:

GTTTTCCCAG TCACGACG                                                     18

(2) INFORMATION FOR SEQ ID NO: 5:

(i) SEQUENCE CHARACTERISTICS:
             (A) LENGTH: 18 base pairs
```

(B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 5:

GAATTGTGAG CGGATAAC                                                    18

(2) INFORMATION FOR SEQ ID NO: 6:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 6:

CGGAATTCTG GTCTACACCA TCAAGC                                           26

(2) INFORMATION FOR SEQ ID NO: 7:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 7:

CATGTCGGTC CAGAGACACT CG                                               22

(2) INFORMATION FOR SEQ ID NO: 8:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 8:

AACAAACATA TGTGCACATG CTCGCCCAGC C                                     31

(2) INFORMATION FOR SEQ ID NO: 9:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 9:

CGGGATCCTA TTAGGGGTCT GTGGCATTGA TG                                    32

(2) INFORMATION FOR SEQ ID NO: 10:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 10:

```
ACCACTGGCG GTGATACTGA G                                              21
```

(2) INFORMATION FOR SEQ ID NO: 11:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 11

```
GGTCATTACT GGACCGGATC                                                20
```

(2) INFORMATION FOR SEQ ID NO: 12:

(i) SEQUENCE CHARACTERISTICS:
            (A) LENGTH: 1240 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 12:

```
GGCGGCGGGC GCTCAGACGG CTTCTCCTCC TCCTCTTGCT CCTCCAAGCT CCTGCTCCTT      60
CGCCGGGAGC CCGCCCGCCG AGTCCTGCGC CAGCGCCGAG GCAGCCTCGC TGCGCCCCAT     120
CCCGTCCCGC CGGGCACTCG GAGGGCAGCG CGCCGGAGGC CAAGGTTGCC CCGCACGGCC     180
CGGCGGGCGA GCGAGCTCGG GCTGCAGCAG CCCCGCCGGC GGCGCGCACG GCAACTTTGG     240
AGAGGCGAGC AGCAGCCCCG GCAGCGGCGG CAGCAGCGGC AATGACCCCT TGGCTCGGGC     300
TCATCGTGCT CCTGGGCAGC TGGAGCCTGG GGACTGGGG CGCCGAGGCG TGCACATGCT      360
CGCCCAGCCA CCCCCAGGAC GCCTTCTGCA ACTCCGACAT CGTGATCCGG GCCAAGGTGG     420
TGGGGAAGAA GCTGGTAAAG GAGGGGCCCT TCGGCACGCT GGTCTACACC ATCAAGCAGA     480
TGAAGATGTA CCGAGGCTTC ACCAAGATGC CCCATGTGCA GTACATCCAT ACGGAAGCTT     540
CCGAGAGTCT CTGTGGCCTT AAGCTGGAGG TCAACAAGTA CCAGTACCTG CTGACAGGTC     600
GCGTCTATGA TGGCAAGATG TACACGGGGC TGTGCAACTT CGTGGAGAGG TGGGACCAGC     660
TCACCCTCTC CCAGCGCAAG GGGCTGAACT ATCGGTATCA CCTGGGTTGT AACTGCAAGA     720
TCAAGTCCTG CTACTACCTG CCTTGCTTTG TGACTTCCAA GAACGAGTGT CTCTGGACCG     780
ACATGCTCTC CAATTTCGGT TACCCTGGCT ACCAGTCCAA ACACTACGCC TGCATCCGGC     840
AGAAGGGCGG CTACTGCAGC TGGTACCGAG GATGGGCCCC CCCGGATAAA AGCATCATCA     900
ATGCCACAGA CCCCTGAGCG CCAGACCCTG CCCCACCTCA CTTCCCTCCC TTCCCGCTGA     960
GCTTCCCTTG GACACTAACT CTTCCCAGAT GATGACAATG AAATTAGTGC CTGTTTTCTT    1020
GCAAATTTAG CACTTGGAAC ATTTAAAGAA AGGTCTATGC TGTCATATGG GGTTTATTGG    1080
GAACTATCCT CCTGGCCCCA CCCTGCCCCT TCTTTTTGGT TTTGACATCA TTCATTTCCA    1140
CCTGGGAATT TCTGGTGCCA TGCCAGAAAG AATGAGGAAC CTGTATTCCT CTTCTTCGTG    1200
ATAATATAAT CTCTATTTTT TTAGGAAAAA AAAAAAAAA                           1240
```

(2) INFORMATION FOR SEQ ID NO: 13:

(i) SEQUENCE CHARACTERISTICS:
    (A) LENGTH: 211 amino acids
    (B) TYPE: amino acid
    (C) STRANDEDNESS: single
    (D) TOPOLOGY: linear (ii) MOLECULE TYPE: protein (xi) SEQUENCE DESCRIPTION: SEQ ID NO: 13:

```
Met Thr Pro Trp Leu Gly Leu Ile Val Leu Leu Gly Ser Trp Ser Leu
 1               5                  10                  15

Gly Asp Trp Gly Ala Glu Ala Cys Thr Cys Ser Pro Ser His Pro Gln
            20                  25                  30

Asp Ala Phe Cys Asn Ser Asp Ile Val Ile Arg Ala Lys Val Val Gly
        35                  40                  45

Lys Lys Leu Val Lys Glu Gly Pro Phe Gly Thr Leu Val Tyr Thr Ile
50                  55                  60

Lys Gln Met Lys Met Tyr Arg Gly Phe Thr Lys Met Pro His Val Gln
65                  70                  75                  80

Tyr Ile His Thr Glu Ala Ser Glu Ser Leu Cys Gly Leu Lys Leu Glu
                85                  90                  95

Val Asn Lys Tyr Gln Tyr Leu Leu Thr Gly Arg Val Tyr Asp Gly Lys
            100                 105                 110

Met Tyr Thr Gly Leu Cys Asn Phe Val Glu Arg Trp Asp Gln Leu Thr
        115                 120                 125

Leu Ser Gln Arg Lys Gly Leu Asn Tyr Arg Tyr His Leu Gly Cys Asn
    130                 135                 140

Cys Lys Ile Lys Ser Cys Tyr Tyr Leu Pro Cys Phe Val Thr Ser Lys
145                 150                 155                 160

Asn Glu Cys Leu Trp Thr Asp Met Leu Ser Asn Phe Gly Tyr Pro Gly
                165                 170                 175

Tyr Gln Ser Lys His Tyr Ala Cys Ile Arg Gln Lys Gly Gly Tyr Cys
            180                 185                 190

Ser Trp Tyr Arg Gly Trp Ala Pro Pro Asp Lys Ser Ile Ile Asn Ala
        195                 200                 205

Thr Asp Pro
    210
```

(2) INFORMATION FOR SEQ ID NO: 14:

(i) SEQUENCE CHARACTERISTICS:
    (A) LENGTH: 963 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO: 14:

```
CAGGAGCCTG GGGGACTGGG CGCCGAGGC GTGCACATGC TCGCCCAGCC ACCCCCAGGA    60

CGCCTTCTGC AACTCCGACA TCGTGATCCG GGCCAAGGTG GTGGGGAAGA AGCTGGTAAA   120

GGAGGGGCCC TTCGGCACGC TGGTCTACAC CATCAAGCAG ATGAAGATGT ACCGAGGCTT   180

CACCAAGATG CCCCATGTGC AGTACATCCA CACGGAAGCT TCCGAGAGTC TCTGTGGCCT   240

TAAGCTGGAG GTCAACAAGT ACCAGTACCT GCTGACAGGT CGCGTCTATG ATGGCAAGAT   300

GTACACGGGG CTGTGCAACT TCGTGGAGAG GTGGGACCAG CTCACCCTCT CCCAGCGCAA   360

GGGGCTGAAC TATCGGTATC ACCTGGGTTG TAACTGCAAG ATCAAGTCCT GCTACTACCT   420
```

```
GCCTTGCTTT GTGACTTCCA AGAACGAGTG TCTCTGGACC GACATGCTCT CCAATTTCGG    480

TTACCCTGGC TACCAGTCCA AACACTACGC CTGCATCCGG CAGAAGGGCG GCTACTGCAG    540

CTGGTACCGA GGATGGGCCC CCCCGGATAA AAGCATCATC AATGCCACAG ACCCCTGAGC    600

GCCAGACCCT GCCCCACCTC ACTTCCCTCC CTTCCCGCTG AGCTTCCCTT GGACACTAAC    660

TCTTCCCAGA TGATGACAAT GAAATTAGTG CCTGTTTTCT TGCAAATTTA GCACTTGGAA    720

CATTTAAAGA AAGGTCTATG CTGTCATATG GGGTTTATTG GGAACTATCC TCCTGGCCCC    780

ACCCTGCCCC TTCTTTTTGG TTTTGACATC ATTCATTTCC ACCTGGGAAT TTCTGGTGCC    840

ATGCCAGAAA GAATGAGGAA CCTGTATTCC TCTTCTTCGT GATAATATAA TCTCTATTTT    900

TTTAGGAAAA CAAAAATGAA AAACTACTCC ATTTGAGGAT TGTAATTCCC AACACCACCT    960

GCT                                                                 963
```

(2) INFORMATION FOR SEQ ID NO: 15:

(i) SEQUENCE CHARACTERISTICS:
        (A) LENGTH: 198 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 15:

```
Arg Ser Leu Gly Asp Trp Gly Ala Glu Ala Cys Thr Cys Ser Pro Ser
1               5                   10                  15

His Pro Gln Asp Ala Phe Cys Asn Ser Asp Ile Val Ile Arg Ala Lys
            20                  25                  30

Val Val Gly Lys Lys Leu Val Lys Glu Gly Pro Phe Gly Thr Leu Val
        35                  40                  45

Tyr Thr Ile Lys Gln Met Lys Met Tyr Arg Gly Phe Thr Lys Met Pro
    50                  55                  60

His Val Gln Tyr Ile His Thr Glu Ala Ser Glu Ser Leu Cys Gly Leu
65                  70                  75                  80

Lys Leu Glu Val Asn Lys Tyr Gln Tyr Leu Leu Thr Gly Arg Val Tyr
                85                  90                  95

Asp Gly Lys Met Tyr Thr Gly Leu Cys Asn Phe Val Glu Arg Trp Asp
            100                 105                 110

Gln Leu Thr Leu Ser Gln Arg Lys Gly Leu Asn Tyr Arg Tyr His Leu
        115                 120                 125

Gly Cys Asn Cys Lys Ile Lys Ser Cys Tyr Tyr Leu Pro Cys Phe Val
    130                 135                 140

Thr Ser Lys Asn Glu Cys Leu Trp Thr Asp Met Leu Ser Asn Phe Gly
145                 150                 155                 160

Tyr Pro Gly Tyr Gln Ser Lys His Tyr Ala Cys Ile Arg Gln Lys Gly
                165                 170                 175

Gly Tyr Cys Ser Trp Tyr Arg Gly Trp Ala Pro Pro Asp Lys Ser Ile
            180                 185                 190

Ile Asn Ala Thr Asp Pro
            195
```

(2) INFORMATION FOR SEQ ID NO: 16:

(i) SEQUENCE CHARACTERISTICS:
        (A) LENGTH: 820 base pairs
        (B) TYPE: nucleic acid
        (C) STRANDEDNESS: single (D) TOPOLOGY: linear (ii) MOLECULE TYPE: DNA (genomic)

(xi) SEQUENCE DESCRIPTION: SEQ ID NO: 16:

| | | | | |
|---|---|---|---|---|
| GGGAAGAAGC | TGGTAAAGGA | GGGGCCCTTC | GGCACGCTGG | TCTACACCAT CAAGCAGATG | 60 |
| AAGATGTACC | GAGGCTTCAC | CAAGATGCCC | CATGTGCAGT | ACATCCATAC GGAAGCTTCC | 120 |
| GAGAGTCTCT | GTGGCCTTAA | GCTGGAGGTC | AACAAGTACC | AGTACCTGCT GACAGGTCGC | 180 |
| GTCTATGATG | GCAAGATGTA | CACGGGGCTG | TGCAACTTCG | TGGAGAGGTG GGACCAGCTC | 240 |
| ACCCTCTCCC | AGCGCAAGGG | GCTGAACTAT | CGGTATCACC | TGGGTTGTAA CTGCAAGATC | 300 |
| AAGTCCTGCT | ACTACCTGCC | TTGCTTTGTG | ACTTCCAAGA | ACGAGTGTCT CTGGACCGAC | 360 |
| ATGCTCTCCA | ATTTCGGTTA | CCCTGGCTAC | CAGTCCAAAC | ACTACGCCTG CATCCGGCAG | 420 |
| AAGGGCGGCT | ACTGCAGCTG | GTACCGAGGA | TGGGCCCCCC | CGGATAAAAG CATCATCAAT | 480 |
| GCCACAGACC | CCTGAGCGCC | AGACCCTGCC | CCACCTCACT | TCCCTCCCTT CCCGCTGAGC | 540 |
| TTCCCTTGGA | CACTAACTCT | TCCCAGATGA | TGACAATGAA | ATTAGTGCCT GTTTTCTTGC | 600 |
| AAATTTAGCA | CTTGGAACAT | TTAAAGAAAG | GTCTATGCTG | TCATATGGGG TTTATTGGGA | 660 |
| ACTATCCTCC | TGGCCCCACC | CTGCCCCTTC | TTTTTGGTTT | TGACATCATT CATTTCCACC | 720 |
| TGGGAATTTC | TGGTGCCATG | CCAGAAAGAA | TGAGGAACCT | GTATTCCTCT TCTTCGTGAT | 780 |
| AATATAATCT | CTATTTTTTT | AGAAAAAAAA | AAAAAAAAA  |                      | 820 |

(2) INFORMATION FOR SEQ ID NO: 17:

(i) SEQUENCE CHARACTERISTICS:
        (A) LENGTH: 164 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 17:

Gly Lys Lys Leu Val Lys Glu Gly Pro Phe Gly Thr Leu Val Tyr Thr
1               5                   10                  15

Ile Lys Gln Met Lys Met Tyr Arg Gly Phe Thr Lys Met Pro His Val
            20                  25                  30

Gln Tyr Ile His Thr Glu Ala Ser Glu Ser Leu Cys Gly Leu Lys Leu
        35                  40                  45

Glu Val Asn Lys Tyr Gln Tyr Leu Leu Thr Gly Arg Val Tyr Asp Gly
    50                  55                  60

Lys Met Tyr Thr Gly Leu Cys Asn Phe Val Glu Arg Trp Asp Gln Leu
65                  70                  75                  80

Thr Leu Ser Gln Arg Lys Gly Leu Asn Tyr Arg Tyr His Leu Gly Cys
                85                  90                  95

Asn Cys Lys Ile Lys Ser Cys Tyr Tyr Leu Pro Cys Phe Val Thr Ser
            100                 105                 110

Lys Asn Glu Cys Leu Trp Thr Asp Met Leu Ser Asn Phe Gly Tyr Pro
        115                 120                 125

Gly Tyr Gln Ser Lys His Tyr Ala Cys Ile Arg Gln Lys Gly Gly Tyr
    130                 135                 140

Cys Ser Trp Tyr Arg Gly Trp Ala Pro Pro Asp Lys Ser Ile Ile Asn
145                 150                 155                 160

Ala Thr Asp Pro (2) INFORMATION FOR SEQ ID NO: 18:

(i) SEQUENCE CHARACTERISTICS:
        (A) LENGTH: 92 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 18:

```
CTCTGGACCG ACATGCTCTC CAATTTCGGT TACCCTGGCT ACCAGTCCAA ACACTACACA      60

TGCTCGCCCA GCCACCCCCG CACGCGCTCC CG                                    92
```

(2) INFORMATION FOR SEQ ID NO: 19:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: DNA (genomic)

(xi) SEQUENCE DESCRIPTION: SEQ ID NO: 19:

```
Leu Trp Thr Asp Met Leu Ser Asn Phe Gly Tyr Pro Gly Tyr Gln Ser
1               5                   10                  15

Lys His Tyr Thr Cys Ser Pro Ser His Pro Arg Thr Arg Ser Thr
            20                  25                  30
```

(2) INFORMATION FOR SEQ ID NO: 20:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 20:

```
GACACCAGAC CAACTGGTAA TG                                               22
```

(2) INFORMATION FOR SEQ ID NO: 21:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 21:

```
CGGAATTCTG TCTCTGGACC GACATGCTCT CC                                    32
```

(2) INFORMATION FOR SEQ ID NO: 22:

(i) SEQUENCE CHARACTERISTICS:
        (A) LENGTH: 207 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 22:

```
Met Ala Pro Phe Ala Pro Met Ala Ser Gly Ile Leu Leu Leu Trp
1               5                   10                  15

Leu Thr Ala Pro Ser Arg Ala Cys Thr Cys Val Pro Pro His Pro Gln
            20                  25              30

Thr Ala Phe Cys Asn Ser Asp Val Val Ile Arg Ala Lys Phe Val Gly
            35                  40              45

Thr Ala Glu Val Asn Glu Thr Ala Leu Tyr Gln Arg Tyr Glu Ile Lys
    50                  55                  60

Met Thr Lys Met Phe Lys Gly Phe Ser Ala Leu Arg Asp Ala Pro Asp
65                  70                  75                  80

Ile Arg Phe Ile Tyr Thr Pro Ala Met Glu Ser Val Cys Gly Tyr Phe
                85                  90                  95

His Arg Ser Gln Asn Arg Ser Glu Glu Phe Leu Ile Ala Gly Gln Leu
            100                 105                 110

Ser Asn Gly His Leu His Ile Thr Thr Cys Ser Phe Val Ala Pro Trp
            115                 120                 125

Asn Ser Met Ser Ser Ala Gln Arg Arg Gly Phe Thr Lys Thr Tyr Ala
130                 135                 140

Ala Gly Cys Glu Glu Cys Thr Val Phe Pro Cys Ser Ser Ile Pro Cys
145                 150                 155                 160

Lys Leu Gln Ser Asp Thr His Cys Leu Trp Thr Asp Gln Leu Leu Thr
                165                 170                 175

Gly Ser Asp Lys Gly Phe Gln Ser Arg His Leu Ala Cys Leu Pro Arg
            180                 185                 190

Glu Pro Gly Leu Cys Thr Trp Gln Ser Leu Arg Ala Gln Met Ala
            195                 200                 205

(2) INFORMATION FOR SEQ ID NO: 23:

(i) SEQUENCE CHARACTERISTICS:
        (A) LENGTH: 207 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 23:

Met Ala Pro Phe Glu Pro Leu Ala Ser Gly Ile Leu Leu Leu Trp
1               5                   10                  15

Leu Ile Ala Pro Ser Arg Ala Cys Thr Cys Val Pro Pro His Pro Gln
            20                  25              30

Thr Ala Phe Cys Asn Ser Asp Leu Val Ile Arg Ala Lys Phe Val Gly
            35                  40              45

Thr Pro Glu Val Asn Gln Thr Thr Leu Tyr Gln Arg Tyr Glu Ile Lys
    50                  55                  60

Met Thr Lys Met Tyr Lys Gly Phe Gln Ala Leu Gly Asp Ala Ala Asp
65                  70                  75                  80

Ile Arg Phe Val Tyr Thr Pro Ala Met Glu Ser Val Cys Gly Tyr Phe
                85                  90                  95

His Arg Ser His Asn Arg Ser Glu Glu Phe Leu Ile Ala Gly Lys Leu
            100                 105                 110

Gln Asp Gly Leu Leu His Ile Thr Thr Cys Ser Phe Val Ala Pro Trp
            115                 120                 125

Asn Ser Leu Ser Leu Ala Gln Arg Arg Gly Phe Thr Lys Thr Tyr Thr
130                 135                 140
```

```
Val Gly Cys Glu Glu Cys Thr Val Phe Pro Cys Leu Ser Ile Pro Cys
145                 150                 155                 160

Lys Leu Gln Ser Gly Thr His Cys Leu Trp Thr Asp Gln Leu Leu Gln
                165                 170                 175

Gly Ser Glu Lys Gly Phe Gln Ser Arg His Leu Ala Cys Leu Pro Arg
                180                 185                 190

Glu Pro Gly Leu Cys Thr Trp Gln Ser Leu Arg Ser Gln Ile Ala
            195                 200                 205
```

(2) INFORMATION FOR SEQ ID NO: 24:

(i) SEQUENCE CHARACTERISTICS:
        (A) LENGTH: 206 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 24:

```
Met Ala Pro Leu Ala Ala Leu Ala Ser Ser Met Leu Leu Leu Leu Trp
1               5                   10                  15

Leu Val Ala Pro Ser Arg Ala Cys Thr Cys Val Pro Pro His Pro Gln
                20                  25                  30

Thr Ala Phe Cys Asn Ser Asp Leu Val Ile Arg Ala Lys Phe Val Gly
            35                  40                  45

Ala Pro Glu Val Asn His Thr Thr Leu Tyr Gln Arg Tyr Glu Ile Lys
        50                  55                  60

Thr Thr Lys Met Phe Lys Gly Phe Asp Ala Leu Gly His Ala Thr Asp
65                  70                  75                  80

Ile Arg Phe Val Tyr Thr Pro Ala Met Glu Ser Val Cys Gly Tyr Ser
                85                  90                  95

His Lys Ser Gln Asn Arg Ser Glu Glu Phe Leu Ile Ala Gly Gln Leu
                100                 105                 110

Arg Asn Gly Leu Leu His Ile Thr Thr Cys Ser Phe Val Val Pro Trp
            115                 120                 125

Asn Ser Leu Ser Phe Ser Gln Arg Ser Gly Phe Thr Lys Thr Tyr Ala
130                 135                 140

Ala Gly Cys Asp Met Cys Thr Val Phe Ala Cys Ala Ser Ile Pro Cys
145                 150                 155                 160

His Leu Glu Ser Asp Thr His Cys Leu Trp Thr Asp Ser Ser Leu Gly
                165                 170                 175

Ser Asp Lys Gly Phe Gln Ser Arg His Leu Ala Cys Leu Pro Gln Glu
                180                 185                 190

Pro Gly Leu Cys Ala Trp Glu Ser Leu Arg Pro Arg Lys Asp
        195                 200                 205
```

(2) INFORMATION FOR SEQ ID NO: 25:

(i) SEQUENCE CHARACTERISTICS:
        (A) LENGTH: 205 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 25:

```
Met Met Ala Pro Phe Ala Ser Leu Ala Ser Gly Ile Leu Leu Leu Leu
1               5                   10                  15
```

-continued

```
Ser Leu Ile Ala Ser Ser Lys Ala Cys Ser Cys Ala Pro Pro His Pro
            20                  25                  30
Gln Thr Ala Phe Cys Asn Ser Asp Leu Val Ile Arg Ala Lys Phe Met
        35                  40                  45
Gly Ser Pro Glu Ile Asn Glu Thr Thr Leu Tyr Gln Arg Tyr Lys Ile
    50                  55                  60
Lys Met Thr Lys Met Leu Lys Gly Phe Lys Ala Val Gly Asn Ala Ala
65                  70                  75                  80
Asp Ile Arg Tyr Ala Tyr Thr Pro Val Met Glu Ser Leu Cys Gly Tyr
                85                  90                  95
Ala His Lys Ser Gln Asn Arg Ser Glu Glu Phe Leu Ile Thr Gly Arg
            100                 105                 110
Leu Arg Asn Gly Asn Leu His Ile Ser Ala Cys Ser Phe Leu Val Pro
        115                 120                 125
Trp Arg Thr Leu Ser Pro Ala Gln Gln Arg Ala Phe Ser Lys Thr Tyr
    130                 135                 140
Ser Ala Gly Cys Gly Val Cys Thr Val Phe Pro Cys Leu Ser Ile Pro
145                 150                 155                 160
Cys Lys Leu Glu Ser Asp Thr His Cys Leu Trp Thr Asp Gln Val Leu
                165                 170                 175
Val Gly Ser Glu Asp Tyr Gln Ser Arg His Phe Ala Cys Leu Pro Arg
            180                 185                 190
Asn Pro Gly Leu Cys Thr Trp Arg Ser Leu Gly Ala Arg
        195                 200                 205

(2) INFORMATION FOR SEQ ID NO: 26:

(i) SEQUENCE CHARACTERISTICS:
        (A) LENGTH: 220 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 26:

Met Gly Ala Ala Arg Ser Leu Pro Leu Ala Phe Cys Leu Leu Leu
1               5                   10                  15
Leu Gly Thr Leu Leu Pro Arg Ala Asp Ala Cys Ser Cys Ser Pro Val
            20                  25                  30
His Pro Gln Gln Ala Phe Cys Asn Ala Asp Ile Val Ile Arg Ala Lys
        35                  40                  45
Ala Val Asn Lys Lys Glu Val Asp Ser Gly Asn Asp Ile Tyr Gly Asn
    50                  55                  60
Pro Ile Lys Arg Ile Gln Tyr Glu Ile Lys Gln Ile Lys Met Phe Lys
65                  70                  75                  80
Gly Pro Asp Gln Asp Ile Glu Phe Ile Tyr Thr Ala Pro Ala Ala
                85                  90                  95
Val Cys Gly Val Ser Leu Asp Ile Gly Gly Lys Lys Glu Tyr Leu Ile
            100                 105                 110
Ala Gly Lys Ala Glu Gly Asn Gly Asn Met His Ile Thr Leu Cys Asp
        115                 120                 125
Phe Ile Val Pro Trp Asp Thr Leu Ser Ala Thr Gln Lys Lys Ser Leu
    130                 135                 140
Asn His Arg Tyr Gln Met Gly Cys Glu Cys Lys Ile Thr Arg Cys Pro
145                 150                 155                 160
```

```
Met Ile Pro Cys Tyr Ile Ser Ser Pro Asp Glu Cys Leu Trp Met Asp
                165                 170                 175

Trp Val Thr Glu Lys Asn Ile Asn Gly His Gln Ala Lys Phe Phe Ala
            180                 185                 190

Cys Ile Lys Arg Ser Asp Gly Ser Cys Ala Trp Tyr Arg Gly Ala Ala
            195                 200                 205

Pro Pro Lys Gln Glu Phe Leu Asp Ile Glu Asp Pro
            210                 215                 220
```

(2) INFORMATION FOR SEQ ID NO: 27:

(i) SEQUENCE CHARACTERISTICS:
        (A) LENGTH: 220 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 27:

```
Met Gly Ala Ala Ala Arg Thr Leu Arg Leu Ala Leu Gly Leu Leu Leu
1               5                   10                  15

Leu Ala Thr Leu Leu Arg Pro Ala Asp Ala Cys Ser Cys Ser Pro Val
            20                  25                  30

His Pro Gln Gln Ala Phe Cys Asn Ala Asp Val Val Ile Arg Ala Lys
            35                  40                  45

Ala Val Ser Glu Lys Glu Val Asp Ser Gly Asn Asp Ile Tyr Gly Asn
        50                  55                  60

Pro Ile Lys Arg Ile Gln Tyr Glu Ile Lys Gln Ile Lys Met Phe Lys
65                  70                  75                  80

Gly Pro Glu Lys Asp Ile Glu Phe Ile Tyr Thr Ala Pro Ser Ser Ala
            85                  90                  95

Val Cys Gly Val Ser Leu Asp Val Gly Gly Lys Lys Glu Tyr Leu Ile
            100                 105                 110

Ala Gly Lys Ala Glu Gly Asp Gly Lys Met His Ile Thr Leu Cys Asp
            115                 120                 125

Phe Ile Val Pro Trp Asp Thr Leu Ser Thr Thr Gln Lys Lys Ser Leu
130                 135                 140

Asn His Arg Tyr Gln Met Gly Cys Glu Cys Lys Ile Thr Arg Cys Pro
145                 150                 155                 160

Met Ile Pro Cys Tyr Ile Ser Ser Pro Asp Glu Cys Leu Trp Met Asp
                165                 170                 175

Trp Val Thr Glu Lys Asn Ile Asn Gly His Gln Ala Lys Phe Phe Ala
            180                 185                 190

Cys Ile Lys Arg Ser Asp Gly Ser Cys Ala Trp Tyr Arg Gly Ala Ala
            195                 200                 205

Pro Pro Lys Gln Glu Phe Leu Asp Ile Glu Asp Pro
            210                 215                 220
```

(2) INFORMATION FOR SEQ ID NO: 28:

(i) SEQUENCE CHARACTERISTICS:
        (A) LENGTH: 171 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 28:

```
Met Gly Ala Ala Ala Arg Ser Leu Arg Leu Ala Leu Gly Leu Leu Leu
 1               5                  10                  15

Leu Ala Ser Leu Val Arg Pro Ala Asp Ala Cys Ser Cys Ser Pro Val
            20                  25                  30

His Pro Gln Gln Ala Phe Cys Asn Ala Asp Val Val Ile Arg Ala Lys
        35                  40                  45

Ala Val Ser Glu Lys Glu Val Asp Ser Gly Asn Asp Ile Tyr Gly Asn
 50                  55                  60

Pro Ile Lys Arg Ile Gln Tyr Glu Ile Lys Gln Ile Lys Met Phe Lys
 65                  70                  75                  80

Gly Pro Asp Lys Asp Ile Glu Phe Ile Tyr Thr Ala Pro Ser Ser Ala
                 85                  90                  95

Val Cys Gly Val Ser Leu Asp Val Gly Gly Lys Lys Glu Tyr Leu Ile
             100                 105                 110

Ala Gly Lys Ala Glu Gly Asp Gly Lys Met His Ile Thr Leu Cys Asp
             115                 120                 125

Phe Ile Val Pro Trp Asp Thr Leu Ser Ile Thr Gln Lys Lys Ser Leu
 130                 135                 140

Asn Lys Arg Ser Asp Gly Ser Cys Ala Trp Tyr Arg Gly Ala Ala Pro
 145                 150                 155                 160

Pro Lys Gln Glu Phe Leu Asp Ile Glu Asp Pro
                 165                 170
```

(2) INFORMATION FOR SEQ ID NO: 29:

(i) SEQUENCE CHARACTERISTICS:
      (A) LENGTH: 212 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO: 29:

```
Met Thr Ala Trp Leu Gly Phe Leu Ala Val Phe Leu Cys Ser Trp Ser
 1               5                  10                  15

Leu Arg Asp Leu Val Ala Glu Ala Cys Thr Cys Val Pro Ile His Pro
            20                  25                  30

Gln Asp Ala Phe Cys Asn Ser Asp Ile Val Ile Arg Ala Lys Val Val
        35                  40                  45

Gly Lys Lys Leu Met Lys Asp Gly Pro Phe Gly Thr Met Arg Tyr Thr
 50                  55                  60

Val Lys Gln Met Lys Met Tyr Arg Gly Phe Gln Ile Met Pro His Val
 65                  70                  75                  80

Gln Tyr Ile Tyr Thr Glu Ala Ser Glu Ser Leu Cys Gly Val Lys Leu
                 85                  90                  95

Glu Val Asn Lys Tyr Gln Tyr Leu Ile Thr Gly Arg Val Tyr Glu Gly
             100                 105                 110

Lys Val Tyr Thr Gly Leu Cys Asn Trp Tyr Glu Lys Trp Asp Arg Leu
             115                 120                 125

Thr Leu Ser Gln Arg Lys Gly Leu Asn His Arg Tyr His Leu Gly Cys
 130                 135                 140

Gly Cys Lys Ile Arg Pro Cys Tyr Tyr Leu Pro Cys Phe Ala Thr Ser
 145                 150                 155                 160

Lys Asn Glu Cys Ile Trp Thr Asp Met Leu Ser Asn Phe Gly His Ser
```

```
                    165                 170                 175
Gly His Gln Ala Lys His Tyr Ala Cys Ile Gln Arg Val Glu Gly Tyr
                180                 185                 190

Cys Ser Trp Tyr Arg Gly Trp Ala Pro Pro Asp Lys Thr Ile Ile Asn
        195                 200                 205

Ala Thr Asp Pro
    210

(2) INFORMATION FOR SEQ ID NO: 30:

(i) SEQUENCE CHARACTERISTICS:
        (A) LENGTH: 937 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 30:
```

| | | | | | |
|---|---|---|---|---|---|
| CGCCGGAGGC | CAAGGTTGCC | CCGCACGGCC | CGGCGGGCGA | GCGAGCTCGG | GCTGCAGCAG | 60
| CCCCGCCGGC | GGCGCGCACG | GCAACTTTGG | AGAGGCGAGC | AGCAGCCCCG | GCAGCGGCGG | 120
| CAGCAGCGGC | AATGACCCCT | TGGCTCGGGC | TCATCGTGCT | CCTGGGCAGC | TGGAGCCTGG | 180
| GGGACTGGGG | CGCCGAGGCG | TGCACATGCT | CGCCCAGCCA | CCCCCAGGAC | GCCTTCTGCA | 240
| ACTCCGACAT | CGTGATCCGG | GCCAAGGTGG | TGGGGAAGAA | GCTGGTAAAG | GAGGGGCCCT | 300
| TCGGCACGCT | GGTCTACACC | ATCAAGCAGA | TGAAGATGTA | CCGAGGCTTC | ACCAAGATGC | 360
| CCCATGTGCA | GTACATCCAT | ACGGAAGCTT | CCGAGAGTCT | CTGTGGCCTT | AAGCTGGAGG | 420
| TCAACAAGTA | CCAGTACCTG | CTGACAGGTC | GCGTCTATGA | TGGCAAGATG | TACACGGGGC | 480
| TGTGCAACTT | CGTGGAGAGG | TGGGACCAGC | TCACCCTCTC | CCAGCGCAAG | GGGCTGAACT | 540
| ATCGGTATCA | CCTGGGTTGT | AACTGCAAGA | TCAAGTCCTG | CTACTACCTG | CCTTGCTTTG | 600
| TGACTTCCAA | GAACGAGTGT | CTCTGGACCG | ACATGCTCTC | CAATTTCGGT | TACCCTGGCT | 660
| ACCAGTCCAA | CACTACGCC | TGCATCCGGC | AGAAGGGCGG | CTACTGCAGC | TGGTACCGAG | 720
| GATGGGCCCC | CCCGGATAAA | AGCATCATCA | ATGCCACAGA | CCCCTGAGCG | CCAGACCCTG | 780
| CCCCACCTCA | CTTCCCTCCC | TTCCCGCTGA | GCTTCCCTTG | GACACTAACT | CTTCCCAGAT | 840
| GATGACAATG | AAATTAGTGC | CTGTTTTCTT | GCAAATTTAG | CACTTGGAAC | ATTTAAAGAA | 900
| AGGTCTATGC | TGTCATATGG | GGTTTATTGG | GAACTAT | | | 937

```
(2) INFORMATION FOR SEQ ID NO: 31:

(i) SEQUENCE CHARACTERISTICS:
        (A) LENGTH: 886 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 31:
```

| | | | | | |
|---|---|---|---|---|---|
| CGCGAGAGAG | AGGCGGTGTG | AGGAGGGAGC | GAGCGAGCAG | CGAACAGGCG | AGGCTCGAGT | 60
| TAGGCGAACA | GAACAGCGGC | TGCAGCTCGA | AGCGCACCCC | GGGGCAGGCA | GCATGACGGC | 120
| GTGGCTCGGC | TTCCTCGCCG | TGTTCCTGTG | CAGCTGGAGC | CTGCGGGACC | TGGTGGCGGA | 180
| GGCGTGCACT | TGCGTCCCCA | TCCACCCGCA | GGACGCGTTC | TGCAACTCCG | ACATCGTGAT | 240
| CCGTGCTAAA | GTTGTGGGGA | AGAAGCTCAT | GAAAGATGGA | CCATTTGGAA | CAATGCGATA | 300

```
CACAGTCAAG CAGATGAAGA TGTACAGGGG CTTCCAGATA ATGCCACACG TTCAGTACAT      360

CTACACAGAA GCCTCAGAGA GTCTTTGTGG TGTGAAACTG GAGGTCAACA AATACCAGTA      420

TCTGATTACA GGCCGCGTGT ACGAAGGGAA GGTTTACACT GGCCTGTGCA ATTGGTATGA      480

GAAATGGGAC CGACTGACTC TGTCCCAGCG TAAAGGACTG AATCATCGTT ATCATCTGGG      540

CTGTGGATGC AAGATTCGGC CCTGCTACTA TTTGCCCTGC TTTGCCACCT CCAAGAATGA      600

GTGCATTTGG ACAGACATGC TCTCCAACTT CGGCCACTCA GGACACCAAG CGAAGCACTA      660

TGCCTGCATC CAGAGGGTGG AAGGTTACTG CAGCTGGTAT AGAGGATGGG CGCCTCCAGA      720

TAAAACGATC ATCAATGCCA CAGATCCCTG AGCACGCTGT ACCTTCCTTA TCTTCCCTCT      780

CCCTTACTTG TGGCTGATCT TCCTTTGGAC ACTAACTCTT ACCCGATCAT GATGATGACA      840

ATGAAATTAG TGCCTGTTTT CTTGCAAATT CTAGCACTTC GAACCG                    886

(2) INFORMATION FOR SEQ ID NO: 32:

(i) SEQUENCE CHARACTERISTICS:
        (A) LENGTH: 1067 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 32:

GGCGGCGGGC GCTCAGACGG CTTCTCCTCC TCCTCTTGCT CCTCCAAGCT CCTGCTCCTT       60

CGCCGGGAGC CCGCCCGCCG AGTCCTGCGC CAGCGCCGAG GCAGCCTCGC TGCGCCCCAT      120

CCCGTCCCGC CGGGCACTCG GAGGGCAGCG CGCCGGAGGC CAAGGTTGCC CCGCACGGCC      180

CGGCGGGCGA GCGAGCTCGG GCTGCAGCAG CCCCGCCGGC GGCGCGCACG GCAACTTTGG      240

AGAGGCGAGC AGCAGCCCCG GCAGCGGCGG CAGCAGCGGC AATGACCCCT GGCTCGGGC      300

TCATCGTGCT CCTGGGCAGC TGGAGCCTGG GGGACTGGGG CGCCGAGGCG TGCACATGCT      360

CGCCCAGCCA CCCCCAGGAC GCCTTCTGCA ACTCCGACAT CGTGATCCGG GCCAAGGTGG      420

TGGGAAGAA GCTGGTAAAG GAGGGGCCCT TCGGCACGCT GGTCTACACC ATCAAGCAGA      480

TGAAGATGTA CCGAGGCTTC ACCAAGATGC CCCATGTGCA GTACATCCAT ACGGAAGCTT      540

CCGAGAGTCT CTGTGGCCTT AAGCTGGAGG TCAACAAGTA CCAGTACCTG CTGACAGGTC      600

GCGTCTATGA TGGCAAGATG TACACGGGGC TGTGCAACTT CGTGGAGAGG TGGGACCAGC      660

TCACCCTCTC CCAGCGCAAG GGGCTGAACT ATCGGTATCA CCTGGGTTGT AACTGCAAGA      720

TCAAGTCCTG CTACTACCTG CCTTGCTTTG TGACTTCCAA GAACGAGTGT CTCTGGACCG      780

ACATGCTCTC CAATTTCGGT TACCCTGGCT ACCAGTCCAA ACACTACGCC TGCATCCGGC      840

AGAAGGGCGG CTACTGCAGC TGGTACCGAG GATGGGCCCC CCCGGATAAA AGCATCATCA      900

ATGCCACAGA CCCCTGAGCG CCAGACCCTG CCCCACCTCA CTTCCCTCCC TTCCCGCTGA      960

GCTTCCCTTG GACACTAACT CTTCCCAGAT GATGACAATG AAATTAGTGC CTGTTTTCTT     1020

GCAAATTTAG CACTTGGAAC ATTTAAAGAA AGGTCTATGC TGTCATA                   1067

(2) INFORMATION FOR SEQ ID NO: 33:

(i) SEQUENCE CHARACTERISTICS:
        (A) LENGTH: 1062 base pairs
        (B) TYPE: nucleic acid
        (C) STRANDEDNESS: single
        (D) TOPOLOGY: linear (ii) MOLECULE TYPE: DNA (genomic)
```

(xi) SEQUENCE DESCRIPTION: SEQ ID NO: 33:

```
GGGGCCGCCG AGAGCCGCAG CGCCGCTCGC CCGCCGCCCC CCACCCCGCC GCCCCGCCCG      60
GCGAATTGCG CCCCGCGCCC TCCCCTCGCG CCCCCGAGAC AAAGAGGAGA GAAAGTTTGC     120
GCGGCCGAGC GGGCAGGTGA GGAGGGTGAG CCGCGCGGAG GGGCCCGCCT CGGCCCCGGC     180
TCAGCCCCCG CCCGCGCCCC CAGCCCGCCG CCGCGAGCAG CGCCCGGACC CCCCAGCGGC     240
GGCCCCGCCC GCCCAGCCCC CCGGCCCGCC ATGGGCGCCG CGGCCCGCAC CCTGCGGCTG     300
GCGCTCGGCC TCCTGCTGCT GGCGACGCTG CTTCGCCCGG CCGACGCCTG CAGCTGCTCC     360
CCGGTGCACC CGCAACAGGC GTTTTGCAAT GCAGATGTAG TGATCAGGGC CAAAGCGGTC     420
AGTGAGAAGG AAGTGGACTC TGGAAACGAC ATTTATGGCA ACCCTATCAA GAGGATCCAG     480
TATGAGATCA AGCAGATAAA GATGTTCAAA GGGCCTGAGA AGGATATAGA GTTTATCTAC     540
ACGGCCCCCT CCTCGGCAGT GTGTGGGGTC TCGCTGGACG TTGGAGGAAA GAAGGAATAT     600
CTCATTGCAG GAAAGGCCGA GGGGGACGGC AAGATGCACA TCACCCTCTG TGACTTCATC     660
GTGCCCTGGG ACACCCTGAG CACCACCCAG AAGAAGAGCC TGAACCACAG GTACCAGATG     720
GGCTGCGAGT GCAAGATCAC GCGCTGCCCC ATGATCCCGT GCTACATCTC CTCCCCGGAC     780
GAGTGCCTCT GGATGGACTG GGTCACAGAG AAGAACATCA ACGGGCACCA GGCCAAGTTC     840
TTCGCCTGCA TCAAGAGAAG TGACGGCTCC TGTGCGTGGT ACCGCGGCGC GGCGCCCCCC     900
AAGCAGGAGT TTCTCGACAT CGAGGACCCA TAAGCAGGCC TCCAACGCCC CTGTGGCCAA     960
CTGCAAAAAA AGCCTCCAAG GGTTTCGACT GGTCCAGCTC TGACATCCCT TCCTGGAAAC    1020
AGCATGAATA AAACACTCAT CCCATGGGTC CAAATTAATA TG                       1062
```

(2) INFORMATION FOR SEQ ID NO: 34:

(i) SEQUENCE CHARACTERISTICS:
       (A) LENGTH: 835 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO: 34:

```
GCTGCAGCAG CCCCGCCGGC GGCGCGCACG GCAACTTTGG AGAGGCGAGC AGCAGCCCCG      60
GCAGCGGCGG CAGCAGCGGC AATGACCCCT TGGCTCGGGC TCATCGTGCT CCTGGGCAGC     120
TGGAGCCTGG GGGACTGGGG CGCCGAGGCG TGCACATGCT CGCCCAGCCA CCCCCAGGAC     180
GCCTTCTGCA ACTCCGACAT CGTGATCCGG GCCAAGGTGG TGGGGAAGAA GCTGGTAAAG     240
GAGGGGCCCT TCGGCACGCT GGTCTACACC ATCAAGCAGA TGAAGATGTA CCGAGGCTTC     300
ACCAAGATGC CCCATGTGCA GTACATCCAT ACGGAAGCTT CCGAGAGTCT CTGTGGCCTT     360
AAGCTGGAGG TCAACAAGTA CCAGTACCTG CTGACAGGTC GCGTCTATGA TGGCAAGATG     420
TACACGGGGC TGTGCAACTT CGTGGAGAGG TGGGACCAGC TCACCCTCTC CCAGCGCAAG     480
GGGCTGAACT ATCGGTATCA CCTGGGTTGT AACTGCAAGA TCAAGTCCTG CTACTACCTG     540
CCTTGCTTTG TGACTTCCAA GAACGAGTGT CTCTGGACCG ACATGCTCTC CAATTTCGGT     600
TACCCTGGCT ACCAGTCCAA ACACTACGCC TGCATCCGGC AGAAGGGCGG CTACTGCAGC     660
TGGTACCGAG GATGGGCCCC CCCGGATAAA AGCATCATCA ATGCCACAGA CCCCTGAGCG     720
CCAGACCCTG CCCCACCTCA CTTCCCTCCC TTCCCGCTGA GCTTCCCTTG GACACTAACT     780
CTTCCCAGAT GATGACAATG AAATTAGTGC CTGTTTTCTT GCAAATTTAG CACTT          835
```

(2) INFORMATION FOR SEQ ID NO: 35:

(i) SEQUENCE CHARACTERISTICS:
        (A) LENGTH: 782 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 35:

```
AGGGGCCTTA GCGTGCCGCA TCGCCGAGAT CCAGCGCCCA GAGAGACACC AGAGAACCCA      60

CCATGGCCCC CTTTGAGCCC CTGGCTTCTG GCATCCTGTT GTTGCTGTGG CTGATAGCCC     120

CCAGCAGGGC CTGCACCTGT GTCCCACCCC ACCCACAGAC GGCCTTCTGC AATTCCGACC     180

TCGTCATCAG GGCCAAGTTC GTGGGGACAC CAGAAGTCAA CCAGACCACC TTATACCAGC     240

GTTATGAGAT CAAGATGACC AAGATGTATA AAGGGTTCCA AGCCTTAGGG GATGCCGCTG     300

ACATCCGGTT CGTCTACACC CCCGCCATGG AGAGTGTCTG CGGATACTTC CACAGGTCCC     360

ACAACCGCAG CGAGGAGTTT CTCATTGCTG GAAAACTGCA GGATGGACTC TTGCACATCA     420

CTACCTGCAG TTTCGTGGCT CCCTGGAACA GCCTGAGCTT AGCTCAGCGC CGGGGCTTCA     480

CCAAGACCTA CACTGTTGGC TGTGAGGAAT GCACAGTGTT TCCCTGTTTA TCCATCCCCT     540

GCAAACTGCA GAGTGGCACT CATTGCTTGT GGACGGACCA GCTCCTCCAA GGCTCTGAAA     600

AGGGCTTCCA GTCCCGTCAC CTTGCCTGCC TGCCTCGGGA GCCAGGGCTG TGCACCTGGC     660

AGTCCCTGCG GTCCCAGATA GCCTGAATCC TGCCCGGAGT GGAACTGAAG CCTGCACAGT     720

GTCCACCCTG TTCCCACTCC CATCTTTCTT CCGGACAATG AAATAAAGAG TTACCACCCA     780

GC                                                                   782
```

(2) INFORMATION FOR SEQ ID NO: 36:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 36:

Tyr Thr Ile Lys
1

(2) INFORMATION FOR SEQ ID NO: 37:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 37:

His Glu Phe Gly His
1          5

(2) INFORMATION FOR SEQ ID NO: 38:

(i) SEQUENCE CHARACTERISTICS:
        (A) LENGTH: 5 amino acids (B) TYPE: amino acid
            (C) STRANDEDNESS: single
            (D) TOPOLOGY: linear (ii) MOLECULE TYPE: protein (xi) SEQUENCE DESCRIPTION: SEQ ID NO: 38:

His Glu Leu Gly His
1               5

(2) INFORMATION FOR SEQ ID NO: 39:

(i) SEQUENCE CHARACTERISTICS:
            (A) LENGTH: 4 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO: 39:

Val Ile Arg Ala
1           4

(2) INFORMATION FOR SEQ ID NO: 40:

(i) SEQUENCE CHARACTERISTICS:
            (A) LENGTH: 6 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO: 40:

Cys Ile Trp Thr Asp Met
1               5

(2) INFORMATION FOR SEQ ID NO: 41:

(i) SEQUENCE CHARACTERISTICS:
            (A) LENGTH: 12 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO: 41:

Xaa Thr Xaa Ser Pro Ser His Pro Gln Asp Ala Phe
1               5                   10

(2) INFORMATION FOR SEQ ID NO: 42:

(i) SEQUENCE CHARACTERISTICS:
            (A) LENGTH: 5 amino acids
            (B) TYPE: amino acid
            (C) STRANDEDNESS: single
            (D) TOPOLOGY: linear
            (E) Xaa is either Phe or Leu (ii) MOLECULE TYPE: protein (xi) SEQUENCE DESCRIPTION: SEQ ID NO: 42:

His Glu Xaa Gly His
1               5

TISSUE INHIBITOR OF METALLOPROTEINASE TYPE THREE (TIMP-3) COMPOSITION AND METHODS

FIELD OF THE INVENTION

The present invention relates in general to metalloproteinase inhibitors and to polynucleotides encoding such factors. In particular, the invention relates to novel mammalian tissue inhibitors of metalloproteinase (herein designated as type three, or "TIMP-3"), to fragments, derivatives, and analogs thereof and to polynucleotides encoding the same. In another aspect, the present invention relates to novel methods of producing such compositions, and methods of using such compositions.

BACKGROUND OF THE INVENTION

Connective tissues are maintained in dynamic equilibrium by the opposing effects of extracellular matrix synthesis and degradation. The extracellular connective tissue matrix consists predominantly of collagens, with proteoglycans, fibronectin, laminin and other minor components making up the remainder.

Degradation of the matrix is brought about by the release of neutral metalloproteinases from resident connective tissue cells and invading inflammatory cells that are capable of degrading at physiological pH most of the matrix macromolecules. See Table 1, below. The proteinases include the mammalian tissue collagenases, gelatinases, and proteoglycanases; leukocyte collagenase and gelatinase (Murphy et al. Biochem. J. 283: 289–221 (1982); Hibbs et al., J. Biol. Chem. 260: 2493–2500 (1985)); macrophage collagenase and elastase (Werb et al. J. Exp. Med. 142: 346–360 (1975); Banda et al., Biochem. J. 193: 589–605 (1981)); and tumour collagenases (Liotta et al., PNAS-USA 76: 2268–2272 (1979); Liotta et al., Biochem. Biophys. Res. Commun. 98: 124–198 (1981); and Salo et al., J. Biol. Chem. 258: 3058–3063 (1983)). For a general review of collagenases and their role in normal and pathological connective tissue turnover see *Collagenase in Normal and Pathological Connective Tissues*, David E. Woolley and John M. Evanson, eds., John Wiley & Sons Ltd. (1988).

There are over five different collagen types (I, II, III, IV, V, etc.) which are differentially distributed among tissues. There is considerable homology and structural similarity among the various collagen types. Particular collagenases show some specificity for particular collagen types. See Table 1, below; Matrisian, Trends In Genetics 6: 121–125 (1990). With regard to inhibition of collagenases and other matrix-degrading metalloproteinases, it is possible that, depending on the actual enzymes, substrates, and inhibitory mechanisms, an inhibitor could act on just one, on several, or on all collagenases and metalloproteinases.

TABLE 1

MATRIX-degrading metalloproteinases

| Name(s) | Size (kDa) | Degrades | Ref. |
|---|---|---|---|
| (1) Interstitial collagenase (Type I collagenase) (MMP-1) | 52 deduced 52, 57 secreted | I, II, III collagen | Scholtz et al., Cancer Res. 48:5539–5545 (1988) |
| PMN Collagenase (MMP-8) | 75 secreted | I, II, III collagen | Macartney et al., Evr. J. Biochem. 130: 71–78 (1983). |
| (2) 72 kDA Type IV collagenase (72 kDa gelatinase) (MMP-2) | 72 secreted | IV, V, VII collagen, fibronectin, gelatins | Collier et al., J. Biol. Chem. 263:6579–6587 (1988) |
| 92 kDa Type IV collagenase (92 kDa gelatinase) (MMP-9) | 78 deduced 92 secreted | IV, V collagen, gelatins | Withelm et al., J. Biol. Chem. 263: 17213–17221 (1989) |
| (3) Stromelysin (transin) (proteoglycanase) (procollagen-activiating factor) (MMP 3) | 53 deduced 57, 60 secreted | Proteoglycans, laminin, fibronectin, III, IV, V collagen, gelatins | Chin et al., J. Biol. Chem. 260: 12367–12376 (1985) |
| Stromelysin-2 (transin-2) (MMP-10) | 53 deduced | III, IV, V collagen, fibronectin, gelatins | Nicholson et al., Biochemistry 28: 5195–5203 (1989) |
| PUMP-1 (MMP-7) (Small metalloproteinase of uterus) | 28 deduced 28 secreted | Gelatins, fibronectin | Quantin et al., Biochemistry 28: 5327–5333 (1989) |

The matrix metalloproteinases are divided into three major subclasses, indicated with arabic numerals, on the basis of their substrate specificities.
The enzymes in each class are bold, and alternative names are shown in parentheses. MMP, matrix metalloproteinase; PMN, polymorphonuclear leukocyte.

The underlying basis of degradative diseases of connective tissue points to the matrix-specific metalloproteinases as having a fundamental role in the etiology of these diseases. Such diseases include dystrophic epidermolysis bullosa; rheumatoid arthritis; corneal, epidermal or gastric ulceration; peridontal disease; emphysema; bone disease; and tumor metastasis or invasion.

Most studies on connective tissue degradation and diseases involving such degradation have limited the measurement of metalloproteinases to collagenase (the most widely studied of this group of metalloproteinases). It is understood however, that the simultaneous effects of collagenase and the other matrix-degrading metalloproteinases will exacerbate the degradation of the connective tissue over that achieved by collagenase alone.

Specific natural inhibitors of collagenase were discovered in crude medium from cultured connective tissues. A metalloproteinase inhibitor known as TIMP (tissue inhibitor of metalloproteinases) has been studied with regard to physicochemical properties and the biochemistry of its interaction with collagenase, Murphy et al., J. Biochem. 195: 167–170 (1981); Cawston et al., J. Biochem. 211: 313–318 (1983); Stricklin et al., J. Biol. Chem. 258: 12252–12258 (1983), and DNA encoding it has been isolated, Docherty et al., Nature 318: 65–69 (1985); Carmichael et al., PNAS-USA 83: 2407–2411 (1986). In an in vitro cell culture model of tumor cell migration through a natural basement membrane, TIMP was able to arrest migration of a collagenase-secreting tumor cell line, Thorgeirsson et al., J. Natl. Canc. Inst. 69: 1049–1054 (1982). In vivo mouse lung colonization by murine B16-FlO melanoma cells was inhibited by injections of TIMP, Schultz et al., Cancer Research 48: 5539–5545 (1988). European Patent Publication No. EP O 189 784 also relates to TIMP.

McCartney et al., Eur. J. Biochem. 130: 79–83 (1983) reported the purification of a metalloproteinase inhibitor from human leukocytes.

DeClerck et al., Cancer Research 46: 3580–3586 (1986) described the presence of two inhibitors of collagenase in conditioned medium from bovine aortic endothelial cells.

Murray et al., J. Biol. Chem. 261: 4154–4159 (1986) reported the purification and partial amino acid sequence of a bovine cartilage-derived collagenase inhibitor.

Langley, et al., EP O 398 753 ("Metalloproteinase Inhibitor," published November 22, 1990) discloses a novel metalloproteinase inhibitor and analogs, polynucleotides encoding the same, methods of production, pharmaceutical compositions, and methods of treatment. The polypeptide of FIG. 2 therein has been referred to as TIMP-2, designating a molecule distinct from TIMP-1, supra. EP O 398 753 describes both bovine and human recombinant TIMP-2.

Staskus et al., J. Biol. Chem. 266: 449–454 (1991) reports a 21 kDa avian metalloproteinase inhibitor obtained from chicken fibroblasts. The authors note the biochemical similarities with other members of the TIMP and TIMP-2 group of proteins and state that the avian material may be a TIMP variant or may represent a third protein within the metalloproteinase inhibitor family. (This material is referred to herein as "ChIMP-3")

Pavloff et al., J. Biol. Chem. 267: 17321–17326 (1992) discloses the cDNA and primary structure of a metalloproteinase inhibitor from chicken embryo fibroblasts.

Yang et al., PNAS-USA 89: 10676–10680 (1992) reports on the role of a 21 kDa protein chicken TIMP-3.

The present work relates to a third type of metalloproteinase inhibitor polypeptides. In one aspect, the present invention involves the cloning of recombinant human TIMP-3 nucleic acid and expression thereof.

SUMMARY OF THE INVENTION

According to the present invention, a class of novel tissue inhibitors of metalloproteinase are provided. For convenience, the present polypeptides are referred to as "TIMP-3," as these polypeptides represent a new class of members of the tissue inhibitors of metalloproteinases. Also provided are DNA sequences coding for all or part of the present TIMP-3's, vectors containing such DNA sequences, and host cells transformed or transfected with such vectors. Also comprehended by the invention are methods of producing recombinant TIMP-3's, and methods of treating disorders. Additionally, pharmaceutical compositions including TIMP-3's and antibodies selectively binding TIMP-3's are provided.

BRIEF DESCRIPTION OF THE DRAWINGS

FIGS. 1A–B show the cDNA sequences and amino acid sequence of a recombinant human tissue inhibitor of metalloproteinase type 3 ("TIMP-3"). The entire 1240 base pair sequence encoding a full-length polypeptide of 211 amino acids is presented. A hydrophobic leader sequence is found at position −23 to −1. The initial cysteine of the mature protein is numbered +1. The amino acids corresponding to the degenerate oligonucleotides which identified the original PCR products are underlined, except that the oligo corresponding to YTIK was used analytically to confirm the identity of the PCR products prior to sequencing. A potential glycosylation site is italicized. A variant polyadenylation signal sequence is marked with asterisks. (The abbreviations are used herein for amino acids, either single letter or triple letter abbreviations, and nucleic acids are those conventionally used, as in Stryer, Biochemistry, 3d ed. 1988, W. H. Freeman, New York, inside back cover.)

FIGS. 4A–C show a comparison [table] of the human TIMP-3 amino acid sequence of FIG. 1 with other TIMP family members. The numbering begins with the first cysteine of the mature protein. As can be seen, the alignment contains gaps for some TIMP family members. The numbering used here is consistent for the numbering used for the recombinant human TIMP-3 of FIGS. 1A–B. Boldface letters indicate conserved amino acids; asterisks represent potential glycosylation sites of TIMP-1;

underlined letters indicate potential glycosylation sites of TIMP-3; the left brackets indicate the beginning of the mature proteins. A bullet (·) indicates those amino acids which are unique to recombinant human TIMP-3. The amino acid sequences were found in the literature as follows: Bovine TIMP-1, Freudenstein et al., Biochem. Biophys. Res. Comm. 171: 250–256 (1990); Human TIMP-1, Docherty et al., Nature 318: 65–69 (1985); Rabbit TIMP-1, Horowitz et al., J. Biol. Chem. 264: 7092–7095 (1989); Mouse TIMP-1, Edwards et al., Nucleic Acid. Res. 14: 8863–8878 (1986); Johnson et al., Mol. Cell. Biol. 7: 2821–2829 (1978); Gewert et al., EMBO 6: 651-651–657 (1987); Bovine TIMP-2, Boone et al., PNAS-USA 87: 2800–2804 (1990); Human TIMP-2, Boone et al, PNAS-USA 87: 2800–2804 (1990); Mouse TIMP-2, Shimizu et al., Gene 114: 291–292 (1992); Chicken TIMP-3, Pavloff et al., J. Biol. Chem. 267: 17321–17326 (1992). Unless otherwise indicated, these sequences referred to from time to time herein were found in these references.

FIG. 5 is a comparison table of the amino acid sequence for the chicken metalloproteinase inhibitor of Staskus et al., J. Biol. Chem. 266: 449–454 (1991) and the recombinant human TIMP-3 of FIG. 1. A solid line between amino acids indicates identity, double dots indicates similarity. A single dot indicates a lesser degree of similarity, and no dot indicates total difference, as described by Grivskov et al., Nucl. Aud. Res. 14: 6745–6763 (1986).

FIGS. 6A–D show the overall homology between the nucleic acid sequence encoding TIMP-3 shown in FIGS. 1A–B and that encoding ChIMP-3.

FIGS. 7A–C show the maximal homology between the nucleic acid sequence encoding TIMP-3 shown in FIGS. 1A–B and that encoding ChIMP-3.

FIG. 8 shows the amino acid sequence alignment of human recombinant TIMP-3 of FIG. 1 and human TIMP-2.

FIGS. 9A–E show the overall homology of the nucleic acid sequence of human recombinant TIMP-3 shown in FIGS. 1A–B and that encoding human TIMP-2.

FIGS. 10A–C show the maximal homology regions of the nucleic acid sequence encoding human recombinant TIMP-3 shown in FIGS. 1A–B and that encoding human TIMP-2.

FIG. 11 shows the amino acid sequence alignment of human recombinant TIMP-3 of FIG. 1 and human TIMP-1.

FIGS. 12A–D show the overall homology of the nucleic acid sequence encoding human recombinant TIMP-3 shown in FIGS. 1A–B and that encoding human TIMP-1.

FIG. 13 shows the maximal homology regions of the FIG. 1 nucleic acid sequence encoding human recombinant TIMP-3 and that encoding human TIMP-1.

Figure 14A:
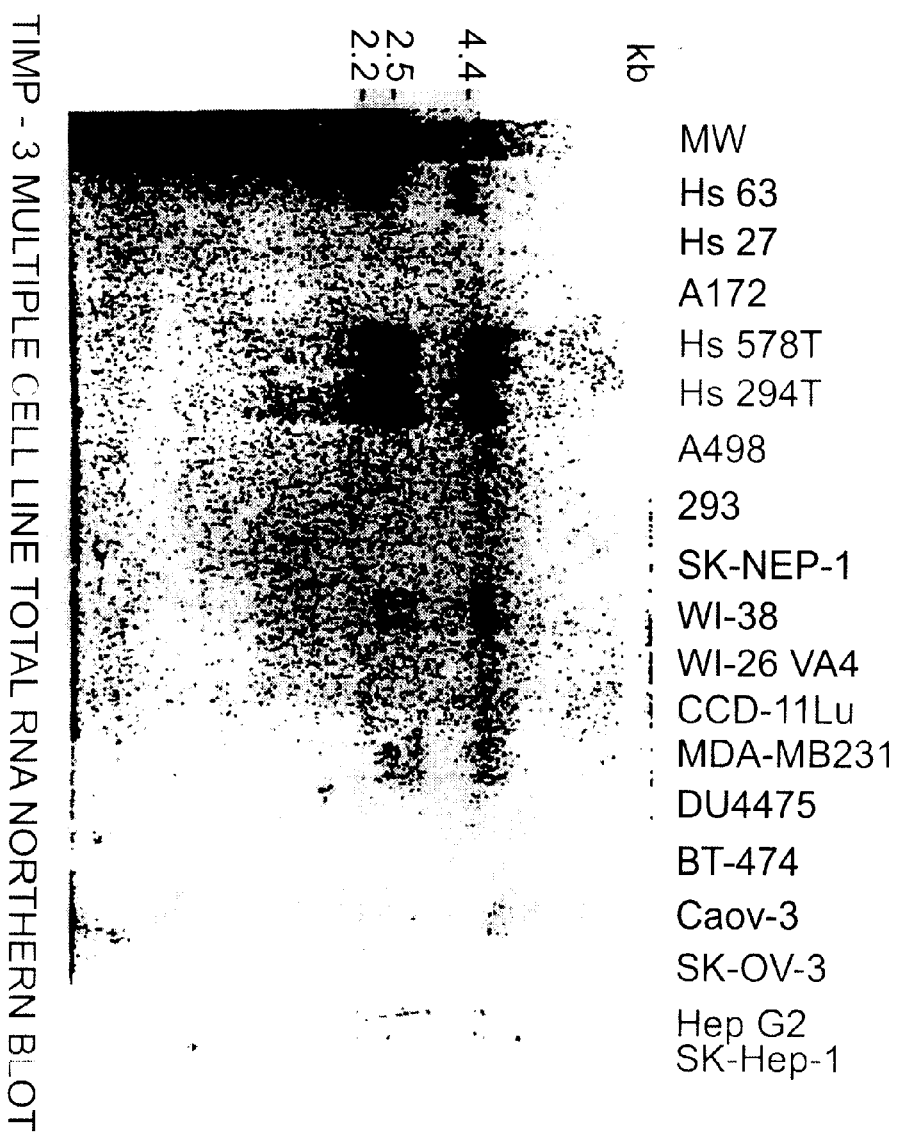
Figure 14B:
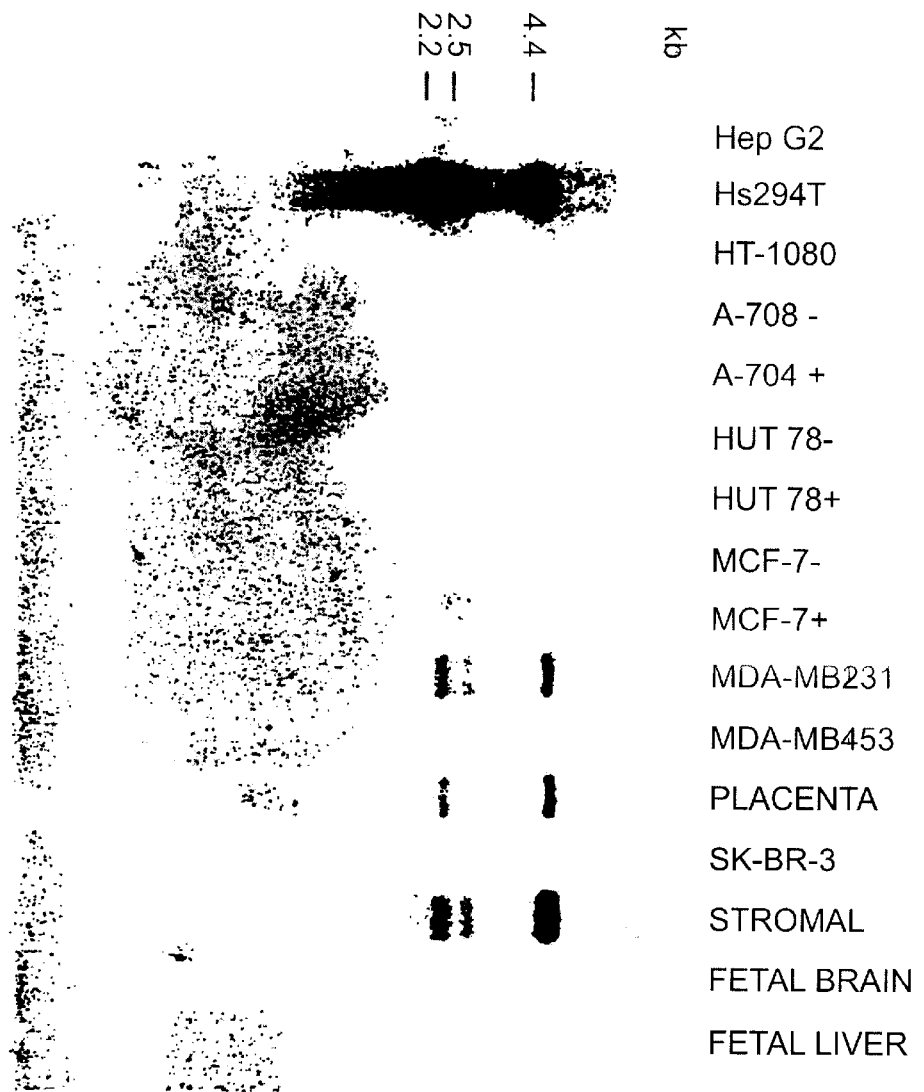

FIGS. 14A and B shows Northern blot analyses performed on RNAs from a variety of cells, using a TIMP-3 DNA fragment as a probe.

Figure 15:
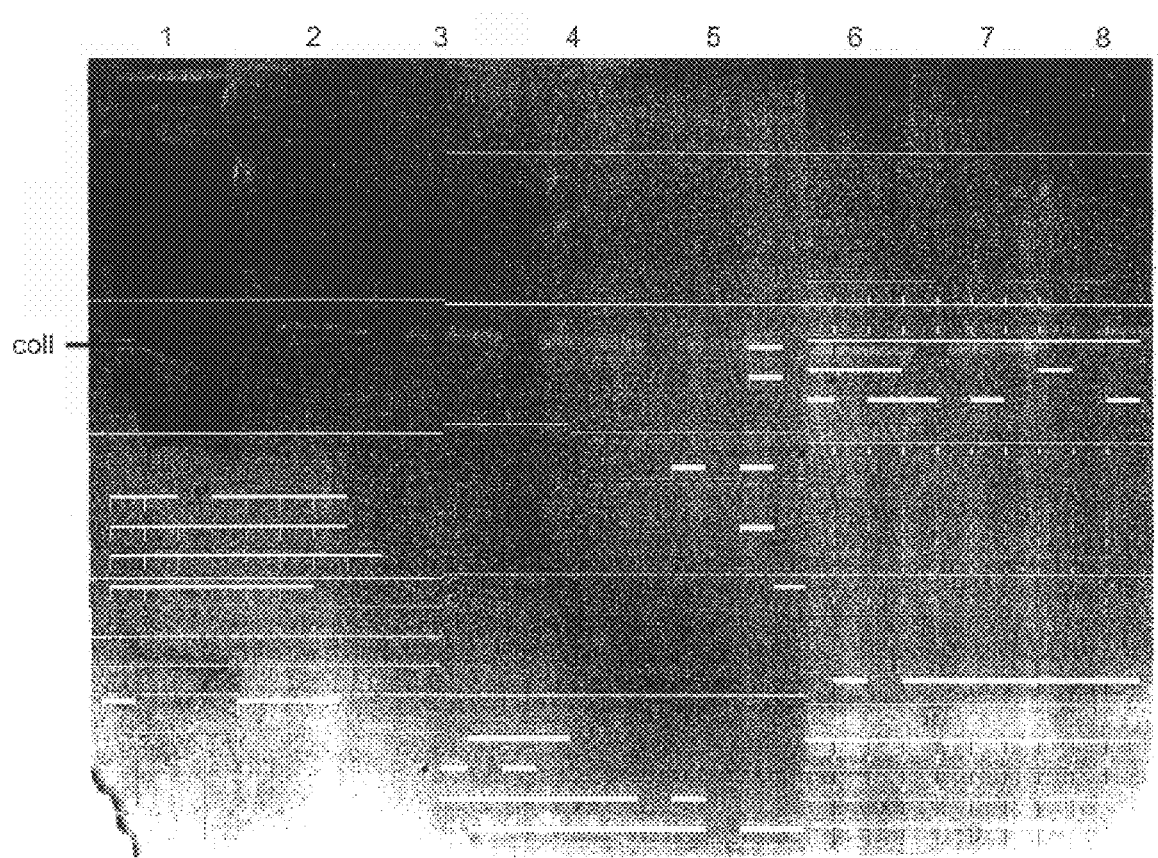

FIG. 15 shows a modified zymogram. Lane 1 (from the left hand side) contains a protein molecular weight standard (see FIG. 3). Lane 2 is a control lane containing conditioned medium with collagenases (72 kDa and interstitial collagenases, pAPMA activated). ("Coll" refers to interstitial collagenase.) Lane 3 contains TIMP-2. Lane 4 contains a TIMP-2 analog lacking the six C-terminal cysteines. Lanes 5, 6, and 7 contain *E. coli* derived TIMP-3 of FIG. 1, lane 5 being undiluted and lanes 6 and 7 being consecutive 2-fold serial dilutions. As can be seen, the lack of a clear zone at the location where the control (lane 2) showed clearing indicates that TIMP-3 inhibits collagenase activity.

Figure 16D:
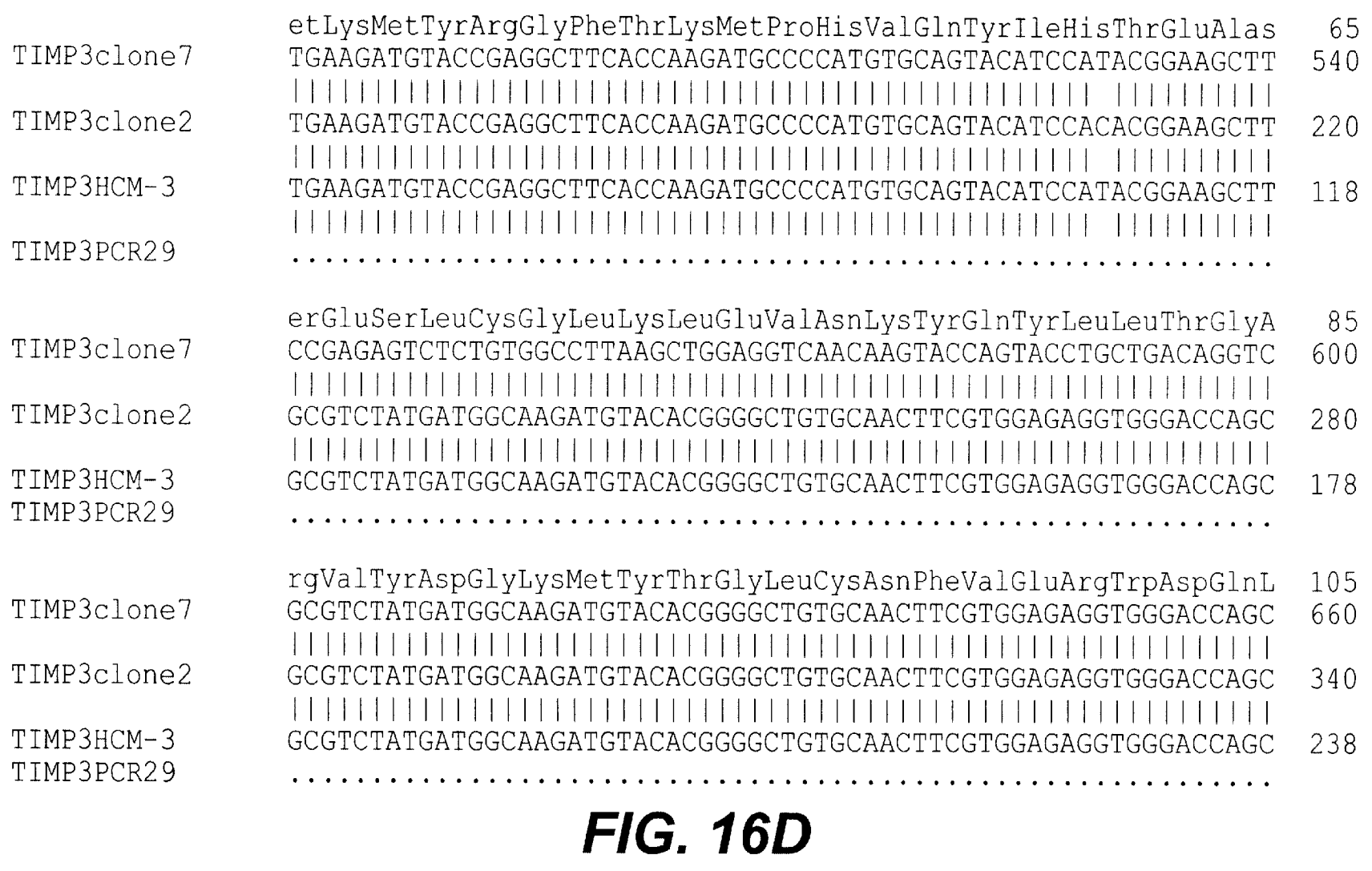
Figure 16E:
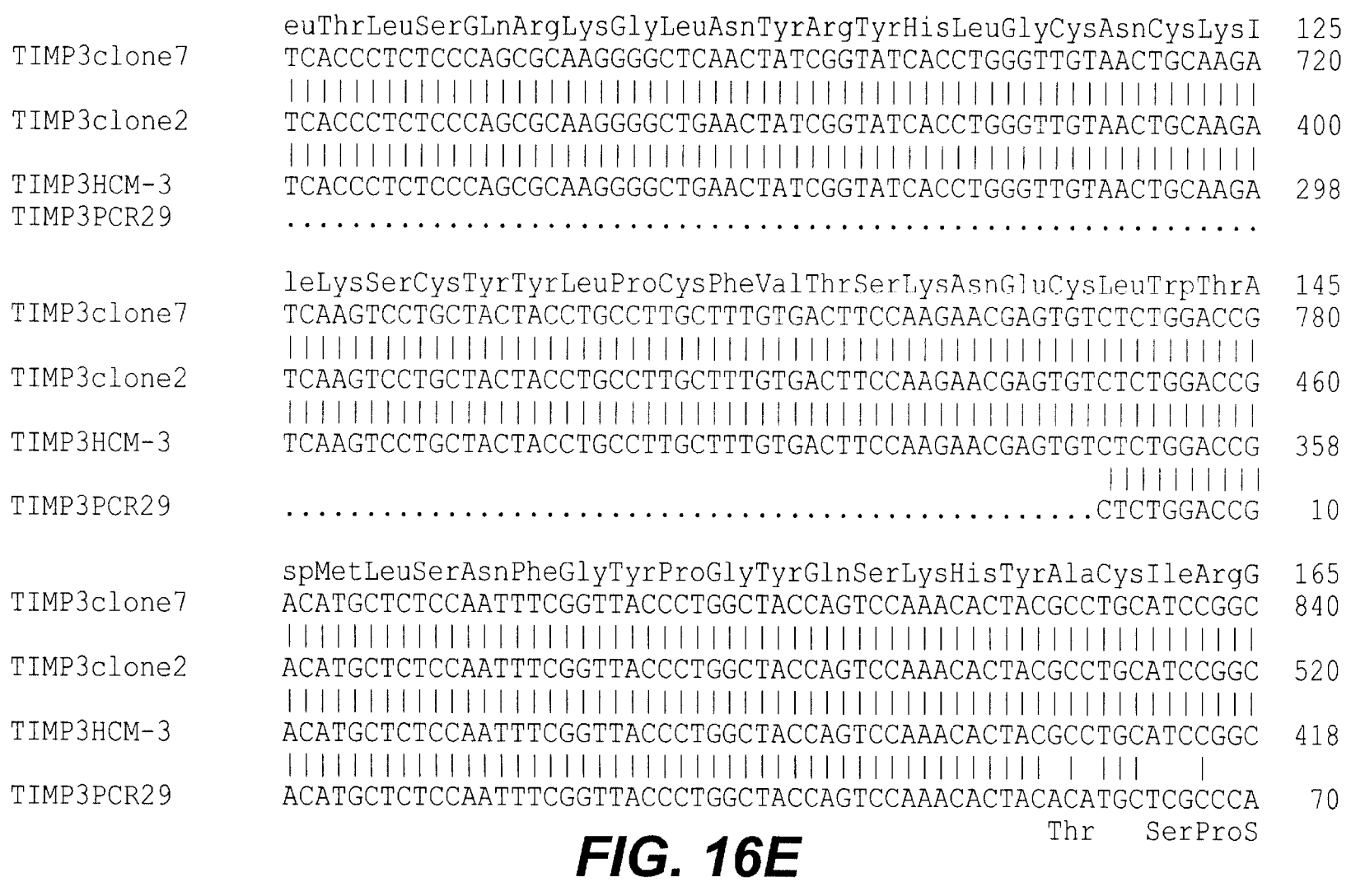

FIGS. 16A–H show the cDNA and amino acid sequence of variants obtained using the present method.

Figure 17:
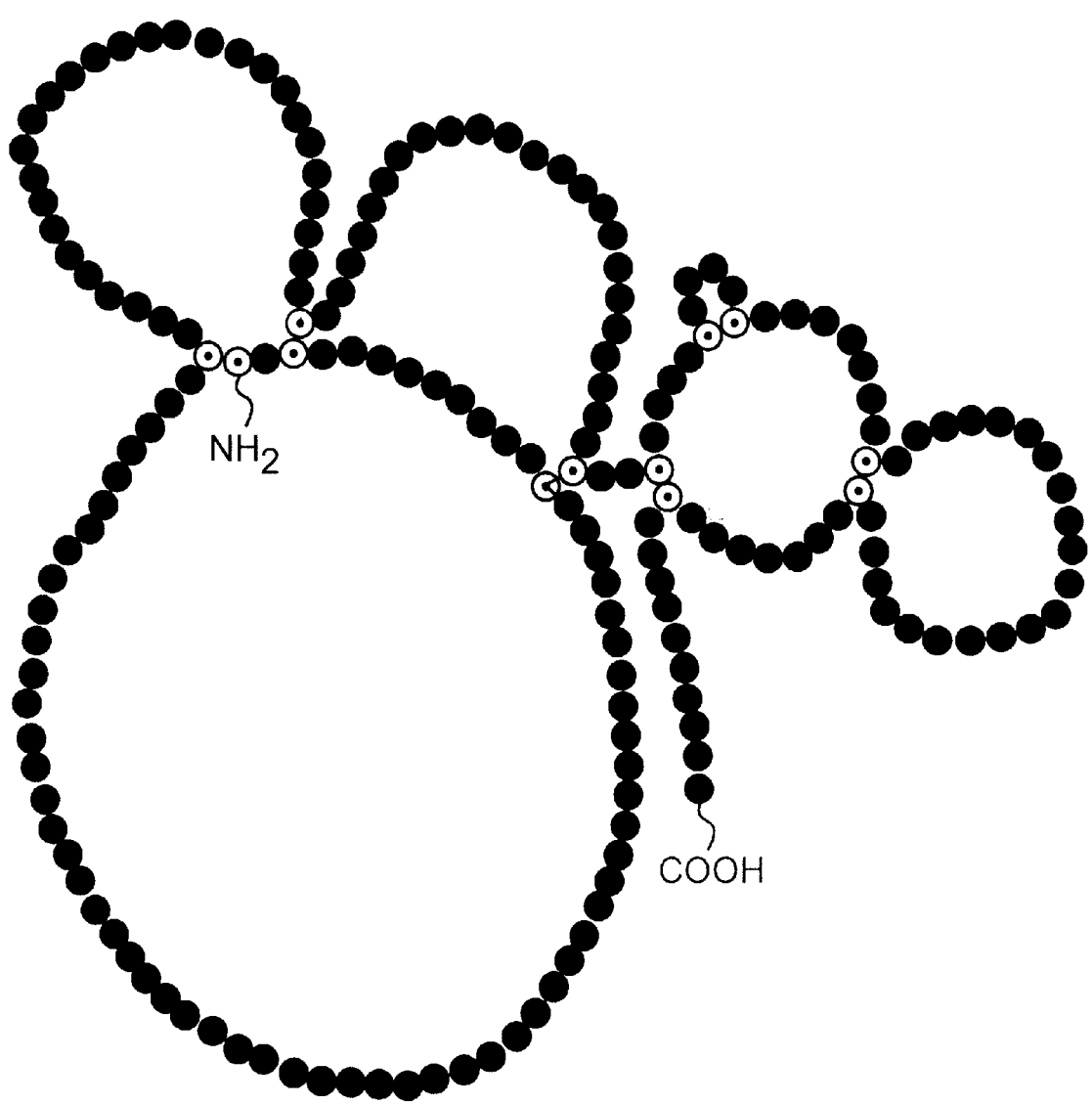

FIG. 17 shows an illustration of a proposed secondary structure of members of the TIMP family of proteins.

Numerous aspects and advantages of the invention will be apparent to those skilled in the art upon consideration of the following detailed description which provides illustrations of the practice of the invention in its presently preferred embodiments.

DETAILED DESCRIPTION OF THE INVENTION

According to the present invention, novel metalloproteinase inhibitors (herein called, collectively, TIMP-3) and DNA sequences coding for all or part of such TIMP-3 are provided. Such sequences include the incorporation of codons "preferred" for expression by selected nonmammalian hosts; the provision of sites for cleavage by restriction endonuclease enzymes; and the provision of additional initial, terminal or intermediate DNA sequences which facilitate construction of readily expressed vectors. The present invention also provides DNA sequences coding for polypeptide analogs or derivatives of TIMP-3 which differ from naturally-occurring forms in terms of the identity or location of one or more amino acid residues (i.e., deletion analogs containing less than all of the residues specified for TIMP-3; substitution analogs, wherein one or more residues specified are replaced by other residues; and addition analogs wherein one or more amino acid residues is added to a terminal or medial portion of the polypeptide) and which share some or all the biological properties of mammaliam TIMP-3.

Novel nucleic acid sequences of the invention include sequences useful in securing expression in procaryotic or eucaryotic host cells of polypeptide products having at least a part of the primary structural conformation and one or more of the biological properties of recombinant human TIMP-3. The nucleic acids may be purified and isolated, so that the desired coding region is useful to produce the present polypeptides, for example, or for diagnostic purposes, as described more fully below. DNA sequences of the invention specifically comprise: (a) the DNA sequence set forth in FIG. 1 (and complementary strands); (b) a DNA sequence which hybridizes (under hybridization conditions disclosed in the cDNA library screening section below, or equivalent conditions or more stringent conditions) to the DNA sequence in FIG. 1 or to fragments thereof; and (c) a DNA sequence which, but for the degeneracy of the genetic code, would hybridize to the DNA sequence in FIG. 1. Also contemplated are fragments of (a), (b) or (c) above which are at least long enough to selectively hybridize to human genomic DNA encoding TIMP-3, under conditions disclosed for the cDNA library screening, below. Specifically comprehended in parts (b) and (c) are genomic DNA sequences encoding allelic variant forms of human TIMP-3 and/or encoding TIMP-3 from other mammalian species, and manufactured DNA sequences encoding TIMP-3, fragments of TIMP-3, and analogs of TIMP-3 which DNA sequences may incorporate codons facilitating transcription and translation of messenger RNA in microbial hosts. Such manufactured sequences may readily be constructed according to the methods of Alton et al., PCT published application WO 83/04053.

Genomic DNA encoding the present TIMP-3's may contain additional non-coding bases, or introns, and such genomic DNAs are obtainable by hybridizing all or part of the cDNA, illustrated in FIGS. 1 and 16, to a genomic DNA source, such as a human genomic DNA library. Such genomic DNA will encode functional TIMP-3 polypeptide; however, use of the cDNAs may be more practicable in that, since only the coding region is involved, recombinant manipulation is facilitated.

According to another aspect of the present invention, the DNA sequences described herein which encode TIMP-3 polypeptides are valuable for the information which they provide concerning the amino acid sequence of the mammalian protein which have heretofore been unavailable. Put another way, DNA sequences provided by the invention are useful in generating new and useful viral and circular plasmid DNA vectors, new and useful transformed and transfected procaryotic and eucaryotic host cells (including bacterial and yeast cells and mammalian cells grown in culture), and new and useful methods for cultured growth of such host cells capable of expression of TIMP-3 and its related products.

The DNA provided herein (or corresponding RNAs) may also be used for gene therapy for, example, treatment of emphysema. For example, transgenic mice overexpressing collagenase exhibit symptoms pulmonary emphysema, D'Armiento et al., Cell 71: 955–961 (1992), indicating that inhibition of collagenase may ameliorate some of the symptoms of emphysema. Currently, vectors suitable for gene therapy (such as retroviral or adenoviral vectors modified for gene therapy purposes and of purity and pharmaceutical acceptability) may be administered for delivery into the lung. Such vectors may incorporate nucleic acid encoding the present polypeptides for expression in the lung. Additionally, one may use a mixture of such vectors, such as those containing genes for one or more TIMPs, elastase inhibitors or other proteins which ameliorate the symptoms of emphysema. Gene therapy may involve a vector containing more than one gene for a desired protein.

Alternatively, one may use no vector so as to facilitate relatively stable presence in the host. For example, homologous recombination may facilitate integration into a host genome. The nucleic acid may be placed within a pharmaceutically acceptable carrier to facilitate cellular uptake, such as a lipid solution carrier (e.g., a charged lipid), a liposome, or polypeptide carrier (e.g., polylysine). A review article on gene therapy is Verma, Scientific American, November 1990, pages 68–84 which is herein incorporated by reference.

As mentioned above, target cells may be within the lungs of the recipient, but other target cells may be bone marrow cells, blood cells, liver (or other organ) cells, muscle cells, fibroblasts, or other cells. The desired nucleic acid may be first placed within a cell, and the cell may be administered to a patient (such as a transplanted tissue) or the desired nucleic acid may be administered directly to the patient for uptake in vivo.

The cells to be transferred to the recipient may be cultured using one or more factors affecting the growth or proliferation of such cells, as for example, SCF.

Administration of DNA of the present invention to the lung may be accomplished by formation of a dispersion of particles, or an aerosol. Typically some type of bulking agent will be involved, and a carrier, such as a lipid or polypeptide. These materials must be pharmaceutically acceptable. One may use a nebulizer for such delivery, such an ultrasonic or dry powder nebulizer. Alternatively, one may use a propellant based system, such as a metered dose inhaler, which may deliver liquid or a suspension of particles.

For gene therapy dosages, one will generally use between one copy and several thousand copies of the present nucleic acid per cell, depending on the vector, the expression system, the age, weight and condition of the recipient and other factors which will be apparent to those skilled in the art.

DNA sequences of the invention are also suitable materials for use as labeled probes in isolating human genomic DNA encoding TIMP-3, as mentioned above, and related proteins as well as cDNA and genomic DNA sequences of other mammalian species. DNA sequences may also be useful in various alternative methods of protein synthesis (e.g., in insect cells) or, as described above, in genetic therapy in humans and other mammals. DNA sequences of the invention are expected to be useful in developing transgenic mammalian species which may serve as eucaryotic "hosts" for production of TIMP-3 and TIMP-3 products in quantity. See, generally, Palmiter et al., Science 222: 809–814 (1983).

Also, one may prepare antisense nucleic acids against the present DNAs. Compare, Khokho et al., Science 243: 947–950 (1989), whereby antisense RNA inhibitor of TIMP conferred oncogenicity on Swiss 3T3 cells. Antisense nucleic acids may be used to modulate or prevent expression of endogenous TIMP-3 nucleic acids.

The present invention provides purified and isolated polypeptide products having part or all of the primary structural conformation (i.e., continuous sequence of amino acid residues) and one or more of the biological properties (e.g., immunological properties and in vitro biological activity) and physical properties (e.g., molecular weight) of naturally-occurring mammalian TIMP-3 including allelic variants thereof. The term "purified and isolated" herein means substantially free of unwanted substances so that the present polypeptides are useful for an intended purpose. For example, one may have a recombinant human TIMP-3 substantially free of other human proteins or pathological agents. These polypeptides are also characterized by being the a product of mammalian cells, or the product of chemical synthetic procedures or of procaryotic or eucaryotic host expression (e.g., by bacterial, yeast, higher plant, insect and mammalian cells in culture) of exogenous DNA sequences obtained by genomic or cDNA cloning or by gene synthesis. The products of expression in typical yeast (e.g., *Saccharomyces cerevisiae*) or procaryote (e.g., *E. coli*) host cells are free of association with any mammalian proteins. The products of expression in vertebrate (e.g., non-human mammalian (e.g. COS or CHO) and avian) cells are free of association with any human proteins. Depending upon the host employed, and other factors, polypeptides of the invention may be glycosylated with mammalian or other eucaryotic carbohydrates or may be non-glycosylated. Polypeptides of the invention may also include an initial methionine amino acid residue (at position −1 with respect to the first amino acid residue of the polypeptide).

In addition to naturally-occurring allelic forms of TIMP-3, the present invention also embraces other TIMP-3 products such as polypeptide analogs of TIMP-3 and fragments of TIMP-3. Following the procedures of the above noted published application by Alton et al. (WO 83/04053), one can readily design and manufacture genes coding for microbial expression of polypeptides having primary conformations which differ from that herein specified for in terms of the identity or location of one or more residues (e.g., substitutions, terminal and intermediate additions and deletions). Alternately, modifications of cDNA and genomic genes may be readily accomplished by well-known site-directed mutagenesis techniques and employed to generate analogs and derivatives of TIMP-3. Such products would share at least one of the biological properties of mammalian TIMP-3 but may differ in others. As examples, projected products of the invention include those which are foreshortened by e.g., deletions; or those which are more stable to hydrolysis (and, therefore, may have more pronounced or longer lasting effects than naturally-occurring); or which have been altered to delete one or more potential sites for glycosylation (which may result in higher activities for yeast-produced products); or which have one or more cysteine residues deleted or replaced by, e.g., alanine or serine residues and are potentially more easily isolated in active form from microbial systems; or which have one or more tyrosine residues replaced by phenylalanine and bind more or less readily to target proteins or to receptors on target cells. Also comprehended are polypeptide fragments duplicating only a part of the continuous amino acid sequence or secondary conformations within TIMP-3, which fragments may possess one activity of mammalian TIMP-3 (e.g., immunological activity) and not others (e.g., metalloproteinase inhibiting activity).

The present TIMP-3 may bind to the extracellular matrix, a characteristic not shared by TIMP-1 and TIMP-2. Thus, polypeptides exhibiting only a part of the continuous amino acid sequence or secondary conformations within TIMP-3 possessing the ability to bind to the extracellular matrix are also specifically contemplated herein.

It is noteworthy that activity is not necessary for any one or more of the products of the invention to have therapeutic utility (see, Weiland et al., Blut 44: 173–175 (1982) or utility in other contexts, such as in assays of TIMP-3 antagonism. Competitive antagonists may be quite useful in, for example, cases of overproduction of TIMP-3.

Of applicability to TIMP-3 fragments and polypeptide analogs of the invention are reports of the immunological activity of synthetic peptides which substantially duplicate the amino acid sequence extant in naturally-occurring proteins, glycoproteins and nucleoproteins. More specifically, relatively low molecular weight polypeptides have been shown to participate in immune reactions which are similar in duration and extent to the immune reactions of physiologically significant proteins such as viral antigens, polypeptide hormones, and the like. Included among the immune reactions of such polypeptides is the provocation of the formation of specific antibodies in immunologically active animals. See, e.g., Lerner et al., Cell 23: 309–310 (1981); Ross et al., Nature 294: 654–656 (1981); Walter et al., PNAS-USA 77: 5197–5200 (1980); Lerner et al., PNAS-USA, 78: 3403–3407 (1981); Walter et al., PNAS-USA 78: 4882–4886 (1981); Wong et al., PNAS-USA 79: 5322–5326 (1982); Baron et al., Cell 28: 395–404 (1982); Dressman et al., Nature 295: 185–160 (1982); and Lerner, Scientific American 248: 66–74 (1983). See, also, Kaiser et al. Science 223: 249–255 (1984) relating to biological and immunological activities of synthetic peptides which approximately share secondary structures of peptide hormones but may not share their primary structural conformation.

One type of analog is a truncated TIMP-3 having capacity to bind to the zinc binding domain of collagenase. For example, the zinc binding domain on interstitial collagenase is located at amino acids 218, 222 and 228 at the pro enzyme. Goldberg, G. I., J. Biol. Chem. 261: 6600–6605 (1986). The zinc binding domain of the 72 kDa species of procollagenase is located at amino acids 403–407. Collier et al., Genomics 9: 429–434 (1991). The zinc binding domain of the 92 kDa species of procollagenase is at amino acids 401–405. Van Ranst et al., Cytokine 3: 231–239 (1991). Interestingly, the zinc binding domain is fairly well conserved among enzymes: H E F G H (SEQ ID NO:37, 92 kDa collagenase), H E F G H (SEQ ID NO:37, 72 kDa collagenase) and H E L G H (SEQ ID NO:38, interstitial collagenase). Thus, the motif for zinc binding is H E X G H (SEQ ID NO:42) wherein X is either F or L. A selective binding molecule, such as an antibody or small molecule would block such zinc binding and therefore inhibit enzymatic activity. (The term "selective binding molecule" as used here indicating a composition which selectively binds to its target.) One may prepare a monoclonal antibody or a recombinant antibody, for example.

TIMP-2 deletion analogs have been prepared which have retained the ability to inhibit metalloproteinase activity. Willenbrock et al., Biochemistry 32: 4330–4337 (1993). For TIMP-2, the C-terminus was shortened to delete six C-terminal cysteines (three disulfide-bonded loops). Thus, in view of the homology among the various zinc binding domains, one could prepare analogous TIMP-3 analogs with similarly shortened C-terminal sequences. The TIMP-3 analog 1-121 (using the numbering of FIG. 1 herein) includes the first six cysteines residues, but not the last six. One may optionally lengthen the C-terminus up to the full length molecule of 188 amino acids. Such analogs may also be prepared for any species, such as ChIMP-3.

This is further demonstrated below in the examples, as a TIMP-2 deletion variant is shown to inhibit interstitial collagenase. (Example 3 below). The zinc binding domain of interstitial collagenase is similarly situated as that of the 72 kDa species collagenase (which was shown by Willenbrock et al., supra, to be affected by the TIMP-2 truncated analogs).

Also, since it is apparent that the C-terminus is not necessary for enzyme inhibition activity, one may chemically modify the C-terminus. One may desire, for example, a sustained release preparation whereby one or more polymer molecules such as polyethylene glycol molecules are attached. Other chemical modifications include attachment of an additional polypeptide for the creation of a fusion molecule. Thus, another aspect of the present invention is chemically modified TIMP-3.

The present invention also includes that class of polypeptides coded for by portions of the DNA complementary to the protein-coding strand of the human cDNA or genomic DNA sequences of TIMP-3 i.e., "complementary inverted proteins" as described by Tramontano et al. Nucleic Acid Res. 12: 5049–5059 (1984). Polypeptides or analogs thereof may also contain one or more amino acid analogs, such as peptidomimetics.

Also comprehended by the invention are pharmaceutical compositions comprising effective amounts of polypeptide products of the invention together with pharmaceutically acceptable diluents, preservatives, solubilizers, emulsifiers, adjuvants and/or carriers useful in TIMP-3 therapy. Such compositions include diluents of various buffer content (e.g., Tris-HCl, acetate, phosphate), pH and ionic strength; additives such as detergents and solubilizing agents (e.g., Tween 80, Polysorbate 80), anti-oxidants (e.g., ascorbic acid, sodium metabisulfite), preservatives (e.g., Thimersol, benzyl alcohol) and bulking substances (e.g., lactose, mannitol); covalent attachment of polymers such as polyethylene glycol to the protein (as discussed supra, see, for example U.S. Pat. No. 4,179,337 hereby incorporated by reference); incorporation of the material into particulate preparations of polymeric compounds such as polylactic acid, polyglycolic acid, etc. or into liposomes. Such compositions will influence the physical state, stability, rate of in vivo release, and rate of in vivo clearance of TIMP-3. See e.g., Remington's Pharmaceutical Sciences, 18th Ed. (1990, Mack Publishing Co., Easton, Pa. 18042) pages 1435–1712 which are herein incorporated by reference.

Generally, an effective amount of the present TIMP-3 polypeptides will be determined by the age, weight and condition or severity of disease of the recipient. See, Remingtons Pharmaceutical Sciences, supra, at pages 697–773, herein incorporated by reference. Typically, a dosage of between about 0.001 g/kg body weight to about 1 g/kg body weight, may be used, but more or less, as a skilled practitioner will recognize, may be used. For local (i.e., non-systemic) applications, such as topical applications, the dosing may be between about 0.001 g/cm$^2$ to about 1 g/cm$^2$. Dosing may be one or more times daily, or less frequently, and may be in conjunction with other compositions as described herein. It should be noted that the present invention is not limited to the dosages recited herein.

A plurality of agents act in concert in order to maintain the dynamic equilibrium of the extracellular matrix and tissues. In treatment of conditions where the equilibrium is skewed, one or more of the other agents may be used in conjunction with the present TIMP-3. These other agents may be co-administered or administered in seriatim, or a combination thereof. Generally, these other agents may be selected from the list consisting of the metalloproteinases, serine proteases, inhibitors of matrix degrading enzymes, intracellular enzymes, cell adhesion modulators, and factors regulating the expression of extracellular matrix degrading proteinases and their inhibitors. While specific examples are listed below, one skilled in the art will recognize other agents performing equivalent functions, including additional agents, or other forms of the listed agents (such as those produced synthetically, via recombinant DNA techniques, and analogs and derivatives).

Metalloproteinases and serine proteases degrade the extracellular matrix, as discussed above. Thus, use of enzymes in therapy may be to counteract effects of the present TIMP-3, which inhibits such degradation. Enzymes include collagenases, PMN (polymorphonuclear leukocyte) collagenase, stromelysin I, II/transin, matrilysin, invadolysin, putative metalloproteinase (PUMP-1), urokinase type plasminogen activator (UPA), tissue plasminogen activator (TPA), and plasmin. PD-ECGF may also be used.

Other degradation inhibitors may also be used if increased or more specific prevention of extracellular matrix degradation is desired. Inhibitors may be selected from the group consisting of $\alpha_2$ macroglobulin, pregnancy zone protein, ovostatin, $\alpha_1$-proteinase inhibitor, $\alpha_2$-antiplasmin, aprotinin, protease nexin-1, plasminogen activator inhibitor (PAI)-1, PAI-2, TIMP-1, and TIMP-2. Others may be used, as one skilled in the art will recognize.

Intracellular enzymes may also be used in conjunction with the present TIMP-3. Intracellular enzymes also may affect extracellular matrix degradation, and include lysozomal enzymes, glycosidases and cathepsins.

Cell adhesion modulators may also be used in combination with the present TIMP-3. For example, one may wish to modulate cell adhesion to the extracellular matrix prior to, during, or after inhibition of degradation of the extracellular matrix using the present TIMP-3. Cells which have exhibited cell adhesion to the extracellular matrix include osteoclasts, macrophages, neutrophils, eosinophils, killer T cells and mast cells. Cell adhesion modulators include peptides containing an "RGD" motif or analog or mimetic antagonists or agonists.

Factors regulating expression of extracellular matrix degrading proteinases and their inhibitors include cytokines, such as IL-1 and TNF-$\alpha$, TGF-$\beta$, glucocorticoids, and retinoids. Other growth factors effecting cell proliferation and/or differentiation may also be used if the desired effect is to inhibit degradation of the extracellular matrix using the present TIMP-3, in conjunction with such cellular effects. For example, during inflammation, one may desire the maintenance of the extracellular matrix (via inhibition of enzymatic activity) yet desire the production of neutrophils; therefore one may administer G-CSF. Other factors include erythropoietin, interleukin family members, SCF, M-CSF, IGF-I, IGF-II, EGF, FGF family members such as KGF, PDGF, and others. One may wish additionally the activity of interferons, such as interferon alpha's, beta's, gamma's, or consensus interferon. Intracellular agents include G-proteins, protein kinase C and inositol phosphatases. While the field of inflammation research is presently under development, and the precise interactions of the described compositions in vivo is not throughly understood, the use of the present polypeptides may provide therapeutic benefit with one or more agents involved in inflammation therapy.

Cell trafficking agents may also be used. For example, inflammation involves the degradation of the extracellular matrix, and the movement, or trafficking of cells to the site of injury. Prevention of degradation of the extracellular matrix may prevent such cell trafficking. Use of the present TIMP-3 in conjunction with agonists or antagonists of cell trafficking-modulation agents may therefore be desired in treating inflammation. Cell trafficking-modulating agents may be selected from the list consisting of endothelial cell surface receptors (such as E-selectins and integrins); leukocyte cell surface receptors (L-selectins); chemokins and chemoattractants. For a review of compositions involved in inflammation, see Carlos et al., Immunol. Rev. 114: 5–28 (1990), which is herein incorporated by reference.

Moreover, compositions may include neu differentiation factor, "NDF," and methods of treatment may include the administration of NDF before, simultaneously with, or after the administration of TIMP-3. NDF has been found to stimulate the production of TIMP-2, and the combination of NDF, TIMP −1, −2 and/or −3 may provide benefits in treating tumors.

Polypeptide products of the invention may be "labeled" by association with a detectable marker substance (e.g., radiolabeled with $125_I$) to provide reagents useful in detection and quantification of TIMP-3 in solid tissue and fluid samples such as blood or urine. Nucleic acid products of the invention may also be labeled with detectable markers (such as radiolabels and non-isotopic labels such as biotin) and employed in hybridization processes to locate the human TIMP-3 gene position and/or the position of any related gene family in a chromosomal map. Nucleic acid sequences which selectively bind the human TIMP-3 gene are useful for this purpose. They may also be used for identifying human TIMP-3 gene disorders at the DNA level and used as gene markers for identifying neighboring genes and their disorders. Contemplated herein are kits containing such labelled materials.

The TIMP-3 compositions described herein modify the pathogenesis and provide a beneficial therapy for diseases of connective tissues characterized by matrix degradation. Also, the present TIMP-3 compositions may be useful in the treatment of any disorder where excessive matrix loss is caused by metalloproteinase activity. The TIMP-3 compositions may be used alone or in conjunction with one or more of the agents discussed herein.

Polypeptide products of the present invention are useful, alone or in combination with other drugs, in the treatment of various disorders such as dystrophic epidermolysis bullosa where the disease is linked to the overproduction of collagenase, Bauer et al., J. Exp. Med. 148: 1378–1387 (1978). The products of the present invention may also be useful in the treatment of rheumatoid arthritis. Evanson et al. J. Clin. Invest. 47: 2639–2651 (1968) noted that large amounts of collagenase are produced, in culture, by excised rheumatoid synovial tissue, this led to immunolocalization studies by Woolley et al., Arthritis and Rheumatism 20: 1231–1239 (1977), with monospecific antibodies directed against human rheumatoid synovial collagenase which detected high levels of immunoreactive collagenase at the sites of joint erosion (cartilagepannus junctions) but not in the cartilage of associated chondrocytes, and not in the synovium at sites remote from the resorbing front. Collagenases have also been demonstrated using many other different preparations derived from human rheumatoid joints and using tissues characterized by other types of arthritis such as osteoarthritis, Reiter's syndrome, pseudogout, juvenile rheumatoid arthritis, and scleroderma.

In periodontal disease affecting the tooth supporting apparatus, elevation of collagenolytic enzymes is evident, and destruction of collagen and connective tissue. See V.-J. Uitto, pp. 211–223 in *Proteinases in Inflammation and Tumor Invasion*, H. Tschesche, ed., Walter de Gruyter & Co., Berlin, N.Y. (1988).

Collagenases have been implicated in ulceration including corneal, epidermal, or gastric ulceration, Brown et al., American J. of Ophthalmology 72: 1139–1142 (1971), and, indeed, metalloproteinase inhibitors are used in the treatment of corneal ulceration. Slansky et al., Annals of Ophthalmology 2: 488–491 (1970).

In wound healing after surgery, TIMP-3 may have particular application for restenosis. Metalloproteinases contribute to the rearrangement of arterial cells, including blockage of the artery. Use of the present TIMP-3 may inhibit such arterial wall rearrangement. Delivery of antisense TIMP-3 nucleic acid may also provide benefit.

In the field of tumor invasion and metastasis, the metastatic potential of some particular tumors correlates with the increased ability to synthesize and secrete collagenases, Liotta et al., Nature 284: 67–68 (1980), and with the inability to synthesize and secrete significant amounts of a metalloproteinase inhibitor, Hicks et al., Int. J. Cancer 33: 835–844 (1984). These processes are related to the passage of tumor cells through connective tissue layers (basement membrane) from tissue sites to the circulation and vice versa, which could be retarded by TIMP-3. TIMP-3 similarly has therapeutic application in inhibiting tumor cell dissemination during removal of primary tumors, during chemotherapy and radiation therapy, during harvesting of contaminated bone marrow, and during shunting of carcinomatous ascites.

A limiting factor in the use of bone marrow transplantation for many advanced cancers with bone marrow involvement is the absence of adequate purging techniques. For example, metastatic interstitial pneumonitis following infusion of improperly purged bone marrow cells has been noted, Glorieux et al., Cancer 58: 2136–2139 (1986); Graeve et al., Cancer 62: 2125–2127 (1988). TIMP-3 administered during infusion of unpurged bone marrow cells will alleviate the need for developing expensive purging techniques.

Diagnostically, correlation between absence of TIMP-3 production in a tumor specimen and its metastatic potential is useful as a prognostic indicator as well as an indicator for possible prevention therapy.

Tumors may also become more or less encapsulated or fibrotic due to increased collagen deposition (or inhibition of breakdown) by both cancer cells and/or surrounding normal cells. Increased encapsulation promoted by TIMP-3 aids in clean tumor excision.

Other pathological conditions in which excessive collagen degradation may play a role and thus where TIMP-3 can be applied, include emphysema, Paget's disease of bone, osteoporosis, scleroderma, pressure atrophy of bone or tissues as in bedsores, cholesteatoma, and abnormal wound healing. TIMP-3 can additionally be applied as an adjunct to other wound healing promoters, e.g., to modulate the turnover of collagen during the healing process.

TIMP-3 also may have erythroid potentiating activity (i.e., stimulation of differentiation of early erythroid progenitors), and thus TIMP-3 may be useful in the treatment of various anemias.

In addition TIMP-3 may have application in the treatment of immunological disorders such as autoimmune diseases (e.g., rheumatoid arthritis, multiple sclerosis) based upon a potential ability to suppress B-cell differentiation as determined by the method of Pisko et al., J. Immunol. 136: 2141–2150 (1986).

Based on its ability to inhibit connective tissue degradation, TIMP-3 and/or other TIMP molecules have application in cases where inhibition of angiogenesis is useful, e.g., in preventing or retarding tumor development, and the prevention of the invasion of parasites. In addition, the present compositions and methods may be applicable for cosmetic purposes, in that localized inhibition of connective tissue breakdown may alter the appearance of tissue.

The present compositions and methods may also be useful in birth control or fertilization modulation as the TIMPs have been shown to prevent or retard follicular rupture, Branstrom et al., Endocrinology 122: 1715–1721 (1988), and interfere with embryo preimplantation development.

The present compositions and methods may be useful in the treatment of nerve cell disorders in that TIMP-3 may protect nerve cells from damage by preserving the basement membrane surrounding nerve cells. Therefore, uses may involve BDNF, NT-3, NGF, CNTF, NDF, SCF, or other nerve cell growth or proliferation modulation factors.

As described above, the present TIMP-3 has wide application in a variety of disorders. Thus, another embodiment contemplated herein is a kit including the present polypeptides and optionally one or more of the additional compositions described above for the treatment of a disorder involving the degradation of extracellular matrix. An additional embodiment is an article of manufacture comprising a packaging material and a pharmaceutical agent within said packaging material, wherein said pharmaceutical agent contains the present polypeptide(s) and wherein said packaging material comprises a label which indicates that said pharmaceutical agent may be used for an indication selected from the group consisting of: cancer, inflammation, arthritis, dystrophic epidermolysis bullosa, periodontal disease, ulceration, emphysema, bone disorders, scleroderma, wound healing, erythrocyte deficiencies, cosmetic tissue reconstruction, fertilization or embryo implant modulation, and nerve cell disorders. This article of manufacture may optionally include other compositions or label descriptions of other compositions.

The nucleic acids provided herein may also be embodied as part of a kit or article of manufacture. Contemplated is an article of manufacture comprising a packaging material and a pharmaceutical agent, wherein said pharmaceutical agent contains the presently provided nucleic acids and wherein said packaging material comprises a label which indicates that said pharmaceutical composition may be used for an indication benefiting from the modulation of said DNA expression, such as a gene therapy indication. Such gene therapy indications, as discussed above, include the treatment of emphysema. A kit containing the nucleic acid(s) may include, optionally, additional factors affecting the ex vivo growth of recipient cells, such as SCF. See, e.g., Zsebo et al., PCT WO 91/05795, herein incorporated by reference.

A further embodiment of the invention is selective binding molecules, such as monoclonal antibodies specifically binding TIMP-3. The hybridoma technique described originally by Kohler and Milstein Eur. J. Immunol. 6, 511–519 (1976) has been widely applied to produce hybrid cell lines that secrete high levels of monoclonal antibodies against many specific antigens. Recombinant antibodies, (see Huse et al., Science 246: 1275 (1989)) may also be prepared. Such antibodies may be incorporated into a kit for diagnostic purposes, for example.

The following examples are offered to more fully illustrate the invention, but are not to be construed as limiting the scope thereof.

EXAMPLE 1
Cloning and Expression of Human TIMP-3 cDNA

The overall cloning strategy involved two steps, the first, obtaining a fragment using PCR from a human fetal kidney cDNA library, and the second, using this partial clone to screen two different cDNA libraries for full length cDNA sequences.

Degenerate PCR primers derived from highly conserved regions of the TIMP gene family were used to amplify TIMP-3 cDNA from human fetal kidney cDNA. This product was then used as a probe to isolate clones from a human fetal kidney cDNA library and a normal human colonic mucosa cDNA library. Clones of 1240, 963 and 827 bp have been isolated and sequenced. The longest clone encodes the entire 211 amino acid pro-polypeptide, having a mature polypeptide of 188 amino acids. The intermediate size clone is truncated but encodes the entire mature protein. The smallest clone is missing the region encoding the first 24 amino acids of the mature polypeptide. Also demonstrated is the expression and purification of mature polypeptide.

MATERIALS AND METHODS
Primers and Initial TIMP-3 DNA Source Used

Degenerate PCR primers were used in a first round screening of first strand cDNAs to obtain a partial TIMP-3 cDNA clone. The degenerate PCR primers were derived from highly conserved regions of the TIMP family of proteins were selected, (see FIG. 4). They were also chosen because of the relatively low degeneracy of their codons.

The forward primer was derived from a sequence (VIRA, SEQ ID NO:39) which is ubiquitous throughout the TIMP family and is found at positions 18–21 of the mature proteins. This 96-fold degenerate forward primer had 11 bases that encoded the TIMP sequence plus 6 bases for an EcoRI site and 2 extra bases (underlined) 449-15: SEQ. ID No. 1: 5'-CGG AAT TCG TNA THM GNG C-3'.

A reverse primer corresponding to a region of ChIMP-3 (CIWTDM, SEQ ID NO:40) was synthesized. This primer, 480-27, included a BamHI site and two extra bases (underlined): SEQ. ID No. 2 5'-CGG GAT CCC ATR TCN GTC CAD ATR CA-3'.

An alternative reverse primer was also used:
SEQ. ID No. 3
480-28 CGG GAT CCR TCN GTC CAD ATR CA The corresponding region is somewhat variant. Amino acids 163–168 of ChIMP-3 are encoded by the version used here, and these were chosen because the M and I distinguished the ChIMP-3 from other TIMPs. It was not initially known if these differences would also be present in human TIMP-3 (if such TIMP did indeed exist), however, a bias away from TIMP-1 and TIMP-2 was used to limit unwanted amplifications. The M at position 168 was especially useful. As a result of its location at the 5' end of the reverse primer, it would not interfere with the PCR process if there were mismatches and it would favor TIMP-3 amplification over other DNAs if this choice were correct.

Amplification of First Strand cDNAs Using Primers

First, the degenerate primers were used to amplify PCR products from the two first strand cDNAs. After a second round of amplification the PCR products of these were subcloned, and one was selected which was used as a probe for cDNA libraries, as described below.

Oligonucleotide synthesis. Oligonucleotides were synthesized on Applied Biosystems 394 automated synthesizers using standard phosphoramidite chemistry. Degenerate oligonucleotides, which were synthesized in greater than 200 nmole quantities, were purified by butanol extraction. Nondegenerate oligonucleotide were synthesized in smaller amounts and were purified Trityl-on using Poly-pak (Glen Research Corp., Sterling, Va.) cartridges following the manufacturer's instructions. Trityl-off purification was done using 1×25 cm Sephadex G-50 chromatography columns and TEAB as the elution buffer.

Polymerase Chain Reaction. All PCR was performed on Perkin Elmer model 9600 instruments using Perkin Elmer Cetus (Norwalk, Conn.) GeneAmp kits according to the manufacturer's instructions which are herein incorporated by reference.

The first round of PCR consisted of 5 cycles at 94° C. for 20 seconds, 50° C. for 20 seconds and 72° C. for 30 seconds. This was followed by 30 cycles at 94° C. for 20 seconds, 50° C. for 20 seconds and 72° C. for 30 seconds. The PCR products were run on a 2% agarose (SeaKem GTG, FMC, Rockland, Me.) gel, prestained with ethidium bromide (Sigma, St. Louis, Mo.), and the bands in the predicted size range were punched out of the gel using a Pasteur pipette. The PCR products were then re-amplified directly from the gel fragments using the same PCR primers and the following program: 1 cycle of 5 minutes at 95° C. followed by 25 cycles of 94° C. for 20 seconds, 50° C. for 20 seconds, and 72° C. for 30 seconds. This process was performed a second time in an effort to obtain large quantities of relatively pure material for subcloning and restriction analysis.

First Strand cDNA Sources Oligo dT-primed first strand cDNA from human colonic mucosa (Dr. Gene Finley, Pittsburgh Va. Medical Center) as well oligo dT-primed first strand cDNA from 22 week old human fetal kidney (Clontech, Palo Alto, Calif.) were used as first-round sources of TIMP-3 cDNA. When the colonic mucosa cDNA source was used, the same banding pattern was observed as that observed with the fetal kidney cDNAs, which confirmed those results. These fetal kidney PCR products were then used for subcloning.

Purification and Subcloning of PCR Products.

The PCR products were run through Centricon-100 columns (Amicon, Beverly, Mass.) to facilitate the DNA to be cleaved with restriction endonucleases. The DNA was then cut with EcoRI and BamHI to ensure that they would not be internally cleaved during the subcloning process. PCR products were cloned into pUC19 after treatment with proteinase K (Crowe et al., 1991) to enhance the cloning efficiency. Colonies were rapidly screened by PCR amplification with vector primers 382-3 SEQ. ID No. 4 (5'-GTT TTC CCA GTC ACG ACG-3') and 382-4 SEQ. ID No.5 (5'-GAA TTG TGA GCG GAT AAC-3'). These products were purified using Centricon-100 concentrators and were sequenced.

Figure 2:
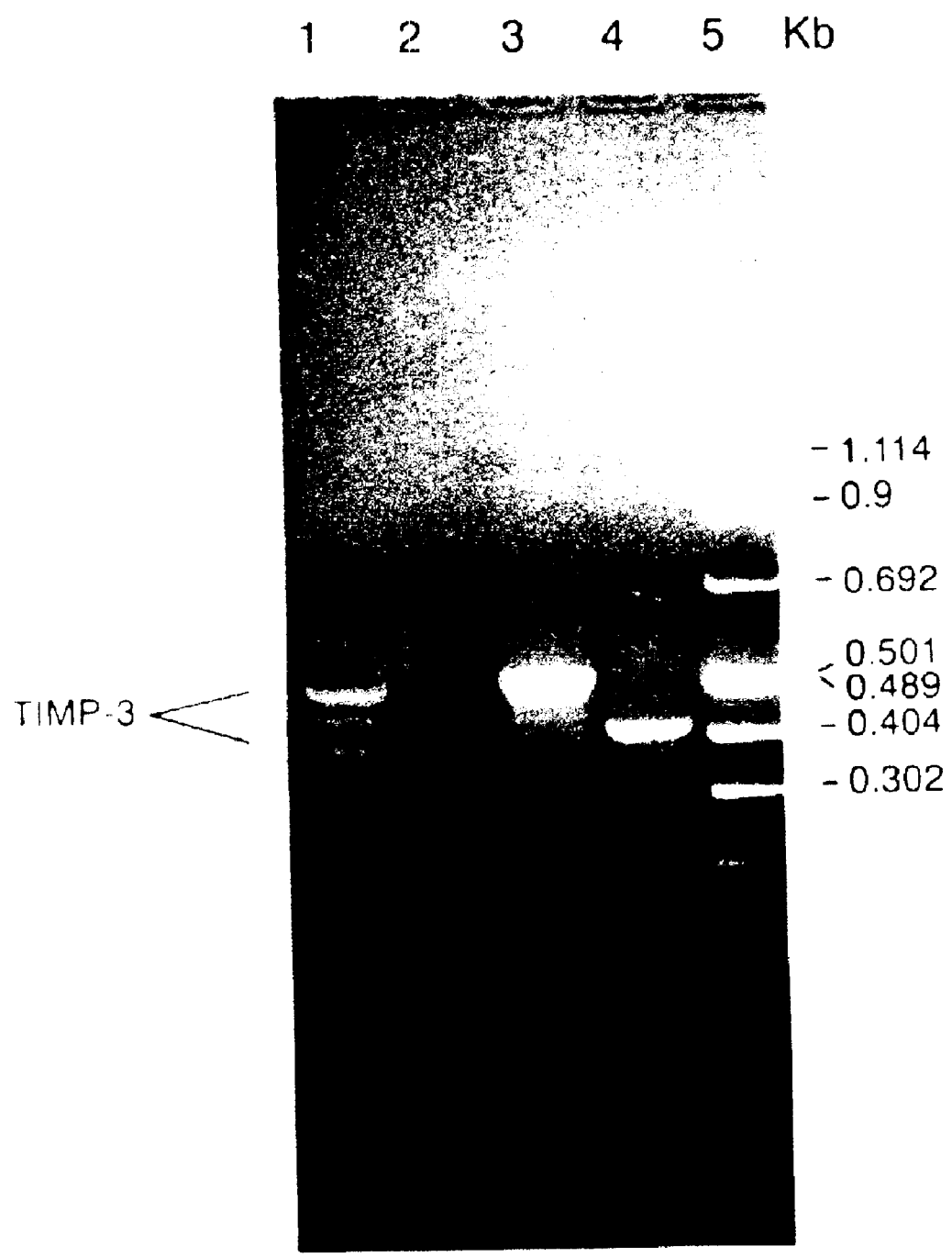
FIG. 2 is a photograph of an agarose gel of first-strand cDNA PCR products, which demonstrate amplification of human nucleic acid. Lane 1 presents PCR products from human fetal kidney first strand cDNA primed with primers 449-15 (Seq. ID No. 1) and 480-27 (Seq. ID No. 2). Lane 2 presents the results of PCR amplification of fetal kidney first strand cDNA primed with primers 449-15 (Seq. ID No. 1 [2]) and 480-28 (Seq. ID No. 3). Lane 3 is the PCR kit (Perkin-Elmer-Cetus) control. Lane 4 is TIMP-2 DNA primed with primers 449-15 (Seq. ID No. 1) and 480-27 (Seq. ID No. 2). Lane 5 is molecular weight markers.

Results. As shown in FIG. 2 three bands resulted from amplification with the degenerate primers. Cloned DNA from two of the bands was sequenced; the third band could not be purified sufficiently to allow subcloning and sequencing.

The smaller of the two sequenced bands was the desired 402 bp fragment and the larger band presumably resulted from false priming to the region encoding CSWYRG (amino acids 169–174 of the mature polypeptide of FIG. 1) and was 489 bp. The 402 bp fragment corresponds to the nucleic acid encoding the region encompassing ValIleArgAla(Lys) to CysLeuTrpThrAspMet of FIG. 1, with an EcoRI on the 5' side, and an BamHI on the 3' side. Also, the codon for isoleucine on the 3' end is replaced with the codon for leucine.

cDNA Library Screening
Screening of a First cDNA Library.

Library. The first library screened was an the oligo(dT)-primed λgt11 Clontech human 20 and 24 week fetal kidney cDNA library (Clontech).

Probes. The first round of cDNA screening was done with the insert of one of the cloned degenerate PCR products previously described, the 402 bp insert. A low level of background was observed as a result of contamination with pUC19 vector DNA. Consequently, the phage supernatant from a partially purified λgt11 clone obtained from the first round of cDNA screening was used as a PCR template. Friedman et al., Nucl. Acids Res. 17: 8718 (1988). This provided a probe of high quality and purity. The Primer 495-21, SEQ. ID No. 6 5'-CGG AAT TCT GGT CTA CAC CAT CAA GC-3' corresponded approximately to the YTIK domain and including an EcoRI site and two additional bases. Primer 496-16, SEQ. ID No. 7 5'-CAT GTC GGT CCA GAG ACA CTC G-3', corresponded to the CLWTDM region and did not include any restriction sites. This resulted in a 333 bp fragment. The sequence of the 333 bp fragment was a portion of the 402 bp fragment sequence. The 333 bp fragment was used as a probe for all of the northern blot analyses and for all further cDNA library screening. The 333 bp fragment corresponds to the region of FIG. 1 encoding TyrThrIleLys through CysLeuTrpThrAspMet and the EcoRI site mentioned above.

Plaque Hybridization About 200,000 phage were plated on ten 150 mm plates, lifted in duplicate onto Schleicher & Schuell supported nitrocellulose membranes and probed with a randomly primed, $^{32}$P-labeled (Stratagene) 402 bp fragment described above. Prehybridizations and hybridizations were performed overnight at 42° C. using the following reagents (for 50 ml of solution):

| | |
|---|---|
| 12.5 ml | 20X SSPE |
| 5 ml | 0.5 N NaHPO$_4$ pH 6.8 |
| 0.1 ml | 0.50 M EDTA pH 8.0 |
| 25 ml | formamide |
| 2.5 ml | 50X Denhardt's |
| 0.25 ml | 20% SDS |
| 0.5 ml | 10 mg/ml tRNA (calf's liver) |
| 1 ml | 10 mg/ml salmon sperm DNA (not used in the pre-hybridization solution) |
| 4.15 ml | H$_2$O (3.15 ml used in the hybridization solution) |

The filters were washed in 0.25×SSC at 42° C. Two positively hybridizing plaques were purified, resulting in 2 independent clones here named Timp3clone7 and Timp3clone2. DNA from bacteriophage lambda was purified using a Qiagen Lambda DNA purification kit (Chatsworth, Calif.). Plate lystates from 10 confluent 135 mm petri dishes were pooled for each specimen. 300 µl of a solution containing 20 mg/ml RNase, 6 mg/ml DNase I, 0.2 mg/ml BSA, 10 mM EDTA, 100 mM Tris-HCl, 300 mM NaCl, pH 7.5 were added and incubated at 37° C. for 30 minutes. 10 ml of ice cold 30% polyethylene glycol (PEG 6000), 3 M NaCl were mixed in and incubated on ice for 60 minutes.

After centrifugation at 10,000×g for 10 minutes, the supernatant was discarded. The pellet was resuspended in 10 ml of a solution containing 100 mM Tris-HCl, 100 mM NaCl and 25 mM EDTA, pH 7.5. 10 ml of a solution containing 4% SDS was gently added and the mixture was heated at 70° C. for 10 minutes and then cooled on ice. 10 ml of 2.55 M potassium acetate, pH 4.8 was mixed in quickly and the solution was centrifuged at 4° C. at 15,000×g for 30 minutes. The supernatant was run on a Qiagen tip-500 column which had been equilibrated with 10 ml of 750 mM NaCl, 50 mM MOPS, 15% ethanol, pH 7.0. The column was then washed with 30 ml 1.0 M NaCl, 50 mM MOPS, 15% ethanol, pH 7.0. Finally, the column was eluted with 15 ml of 1.25 M NaCl, 50 mM MOPS, 15% ethanol, pH 8.2. The eluate was precipitated in 0.7 volumes of isopropanol and centrifuged at 4° C. for 30 minutes. The pellet was air dried for 5 minutes and cut with Boehringer Mannheim (Mannheim, Germany) high concentration EcoRI.

The inserts which had hybridized to the 333 bp probe were purified from agarose gel slices using a Qiaex DNA extraction kit (Qiagen, Chatsworth, Calif.). A solution of 3 M NaI, 4 M NaClO$_4$, 5 mM Tris-H, pH 7.5 at three times the volume of the gel slice was added, along with 0.1 times the gel slice volume of 1 M mannitol and 10 ml of Qiaex resin in a 1.5 ml microcentrifuge tube. This mixture was heated at 50° C. for 10 minutes or until the agarose is completely dissolved. The DNA was allowed to adsorb at room temperature for 5 minutes and then the tubes were briefly centrifuged (6 seconds). After the supernatants were discarded, the Qiaex resin in the tubes were washed in a solution containing 8 M NaClO$_4$, and centrifuged (6 seconds). This wash and centrifugation was repeated and was followed by 2 washes (each followed by 6-second centrifugations) in a solution containing 70% ethanol, 100 mM NaCl, 10 mM Tris-HCl, 1 mM EDTA, pH 7.5. The resin was air dried and eluted in 20 µl of water.

The purified inserts were cloned into pUC19 (New England Biolabs) using Boeringer Mannheim's T4 DNA polymerase. There was an insert to vector (molar) ratio of approximately 5:1. Ligations were performed overnight at 14° C. The ligated material was ethanol precipitated in the presence of glycogen to increase the recovery. This material was then electroporated into BRL's (Gibco-BRL, Gathersburg, Md.) electroporation competent DH10B cells.

Preparations of plasmid DNA were made using using Qiagen plasmid DNA purification kit. A 10 ml overnight culture of a single bacterial colony was grown in terrific broth [Tartoff and Hobbs, Bethesda Res. Lab. Focus 9:12 (1987). Per liter: 12 g bacto-tryptone, 24 g bacto-yeast extract, 4 ml glycerol] with 50 µg/ml ampicillin. The overnight growth was used to inoculate a 250 ml culture in a sterile 1-liter baffled flask containing terrific broth with 50 µg/ml ampicillin. After this grew to saturation, the medium was centrifuged at 5000 rpm for 10 minutes. The bacterial pellet was resuspended in 10 ml of 100 µg/ml RNaseA, 50 mM Tris-HCl. 10 ml of 200 mM NaOH, 1% SDS was added to the resuspended pellet and the mixture was incubated at room temperature for 5 minutes. 10 ml of 2.55 M KAc, pH 4.8 was added and mixed gently. The material was immediately centrifuged at 10000 rpm for 10 minutes. The supernatant was filtered through a cotton gauze pad and the lysate that was particle-free was added to a Qiagen tip-500 column following the same procedure as per the lambda DNA preparation procedure.

Screening of a second cDNA library. A cDNA library from human colonic mucosa, kindly provided by Jim Pipas of the University of Pittsburgh, was the second library screened for TIMP-3 cDNA. This library used Uni-Zap (Stratagene, La Jolla, Calif.) as the vector and had a titer of 2.4×10$^{10}$ pfu/ml. Hybridization was performed as with the kidney library, using the 333 bp probe. The Uni-Zap vector has a pBluescript phagemid which was excised from the phage to which the probes hybridized, and sequenced directly.

Phage particles were isolated and amplified as follows. Phage particles were released into the SM buffer by incubating for 2 hours at room temperature. In a 50 ml test tube, 200 µl of O.D.$_{600}$=1.0 XL1-Blue cells and 200 µl of the lambda Zap phage were combined with 1 ml of R408 helper phage which had a titer of $10^{10}$ pfu/ml. This mixture was incubated at 37° C. for 15 minutes. 3 ml of 2×YT medium (per liter: 16 g bacto-tryptone, 10 g bacto-yeast extract, 5 g NaCl) were added and the mixture was then incubated for 2.5 hours at 37° C. with shaking. The tube was heated at 70° C. for 20 minutes and then centrifuged at 4000×g for 5 minutes.

To rescue the phagemid, 50 µl of the heat-disrupted phage stock were incubated with 200 µl of O.D.$_{600}$=1.0 XL1-Blue cells in a 1.5 ml tube. Additionally, 10 µl of a $10^{-2}$ dilution of heat-disrupted phage were incubated with 200 µl of O.D.$_{600}$=1.0 XL1-Blue cells in a separate 1.5 ml tube. The tubes were incubated at 37° C. for 15 minutes and the cells were then plated on LB ampicillin plates and incubated overnight at 37° C. Colonies appearing on the plate contained the pBluescript SK-double stranded phagemid with the cloned DNA insert.

This screening resulted in one clone, here named "TIMP3HCM3," (see FIG. 16), lacking a portion encoding the N-terminus of the mature polypeptide.

DNA Sequencing

All sequencing was performed on Applied Biosystems, Inc. (ABI) 373A Automated Sequencers. PCR products were sequenced using nested pUC vector dye-primers and ABI's catalyst to perform the reactions.

Double stranded cDNAs cloned into pUC19 were sequenced using ABI's Prism Ready Reaction Dye-Deoxy Terminator Cycle Sequencing Kit using the protocol that came with the kit. For areas of high GC content leading to hairpin loops, reactions were done with the following changes from the standard kit protocol: denaturation at 98° C. for 30 seconds, 12 U Amplitaq, substitution of New England Biolabs (NEB) Vent Polymerase buffer for the ABI TACS buffer and, 30 cycles instead of 25 cycles.

Sequence Analysis

DNA and deduced amino acid analyses used the Genetics Computer Group (GCG) sequence analysis software package from the University of Wisconsin Department of Genetics, Genetic Computer Group, Inc., University Research Park, 575 Science Drive, Suite B, Madison, Wis. 53711.

Expression of Recombinant Human TIMP-3 in *E. coli*

The coding sequence of Timp3clone7 (ATCC Accession No. 69454) was amplified by PCR using standard kit protocol. All deposits were made with the American Type Culture Collection, P.O. Box 1549, Manassas, Va. 20108, USA. Primer 544-29 SEQ. ID No. 8 (5'-AAC AAA CAT ATG TGC ACA TGC TCG CCC AGC C-3') consists of nucleotides 351 to 369, which encodes TIMP-3 amino acids 24–29 (1–6 of the mature protein of FIG. 1). An NdeI site and 6 extra bases (underlined) were included to facilitate subcloning into a bacterial expression vector. The methionine initiator codon, (italics), was added to facilitate expression. The downstream primer, 532-13, SEQ. ID No. 9 (5'-CGG GAT CCT ATT AGG GGT CTG TGG CAT TGA TG-3') corresponds to nucleotides 896 to 914 (of FIG. 1) with an added BamHI site and 2 additional bases (underlined) as well as two stop codons (italicized). The naturally occurring stop codon, TGA (TCA on the reverse complement) was changed to TAA (TTA on the reverse complement), since it is a more efficient stop in *E. coli*. The second stop codon, TAG, (CTA on the reverse complement) was added as a backup.

The vector pCFM3102, as described below, was digested with NdeI and BamHI overnight as was the 589 bp PCR fragment encoding TIMP-3. The reaction was stopped by extraction with phenol/chloroform followed by extraction with chloroform alone. The aqueous layer was then passed through a 1 ml Sephadex G-50 spin column (in a 1 ml syringe) that was equilibrated with 200 µl 10 mM Tris-HCl, 1 mM EDTA pH 8.0. The flow-through from the column was collected and precipitated with 0.1 volumes of 3 M NaAc, pH 5.4 and 2.5 volumes of 100% ethanol. After centrifugation, the pellet was washed in 70% ethanol and dried in a Speed-Vac (Savant). The pellets were resuspended in 20 µl Super-Q water.

A mock ligation containing cut pCFM3102 with no insert was done in addition the TIMP-3::pCFM3102 ligation. Ligations were performed overnight at 14° C., using Boehringer Mannheim T4 DNA ligase. They were then precipitated, washed and dried as above. The pellets were then resuspended in 5 µl of Super-Q water. 2.5 µl of each ligation was used to electroporate 40 µl of electroporation competent cells.

Electroporation of plasmid into *E. coli* occurred in 0.1 cm cuvettes (Bio-Rad) at 1.9 kV, 200 ohms, 25 µF using a Bio-Rad Gen Pulser and with immediate recovery in 5 ml of SOC medium. The cells recovered at 28° C. for 11.3 hours and were plated out onto LB plates containing kanamycin. The plates were incubated at 28° C. overnight. Colonies were screened for inserts by PCR using vector-specific primers 315-21 SEQ. ID No. 10 (5'-ACC ACT GGC GGT GAT ACT GAG-3') and 315-22 SEQ. ID No.11 (5'-GGT CAT TAC TGG ACC GGA TC-3'). Colonies having inserts gave PCR products that are 589 bp larger than the PCR product derived from the original vector without an insert.

Construction of Expression Plasmid pCFM3102

Expression of the mature protein was accomplished in *E. coli* using a plasmid vector. A culture of this *E. coli*, containing plasmid encoding a mature polypeptide as presented in FIG. 1, is deposited at the ATCC, accession no. 69455.

The plasmid used was derived from pCFM836, which is fully described in U.S. Pat. No. 4,710,473, herein incorporated by reference. The construction for the present plasmid (denominated pCFM3102) from the described pCFM836 plasmid (U.S. Pat. No. 4,710,473) was by destroying the two endogenous NdeI restriction sites, by end filling with T4 polymerase enzyme followed by blunt end ligation, by replacing the DNA sequence between the unique AatII and ClaI restriction sites containing the synthetic $P_L$ promoter with a similar fragment obtained from pCFM636 (U.S. Pat. No. 4,710,473) containing the $P_L$ promoter, by substituting the small DNA sequence between the unique ClaI and KpnI restriction sites with an oligonucleotide containing a number of restriction sites, and by making a series of site directed base changes by PCR overlapping oligonucleotide mutagenesis through the intermediate pCFM1656 vector (4799 base pair).

Fermentation

The inoculum for the fermentation was started by transferring 0.1 ml of a glycerol stock at 1 O.D./ml in LB+17% glycerol of ATCC Accession No. 69455 (*E. coli* host cells containing the pCFM3102 with inserted TIMP-3 coding sequences) into a 2-L nippled flask containing 500 ml of Luria Broth (10 g/L Trypticase-Peptone, 10 g/L yeast extract, and 5 g/L sodium chloride). The culture was placed in a shaking platform incubator at 30° C. for 16 hours at 250 rpm. The culture was then transferred to 8 liters of sterile medium in a BioLafitte 15-L fermentor.

The 8 liters of medium that were sterilized in place in the fermentor consisted of the following:

| | |
|---|---|
| 10 g/L | yeast extract |
| 5.25 g/L | ammonium sulfate |
| 3.5 g/L | dibasic potassium phosphate |
| 4.0 g/L | monobasic potassium phosphate |
| 1.25 g/L | sodium chloride |

After the sterilized medium cooled to 30° C. the following was added:

| | |
|---|---|
| 40 g | glucose |
| 8 g | magnesium sulfate-heptahydrate |
| 16 ml | trace metals solution[1] |

The pH of the medium was then adjusted to 7.0 using concentrated phosphoric acid. The other parameters of the fermentation during this batch phase were set as follows:

air flow rate=31.0 L/min agitation=350 rpm dissolved oxygen readout set at 60% oxygen flow rate=0 back pressure=0.5 bar

Once the culture in the fermentation vessel reached at O.D.600 of 6.0, a concentrated solution of glucose and organic nitrogen was started using a schedule that ramps the feed flow according to the O.D. of the culture. This concentrated feed (Feed 1) consisted of the following:

| | |
|---|---|
| 50 g/L | Trypticase-peptone |
| 50 g/L | yeast extract |
| 450 g/L | glucose |
| 8.5 g/L | Magnesium-heptahydrate |
| 10 ml | trace metals solution[1] |
| 10 ml | vitamin solution[2] |

At the time that the concentrated feed was first introduced into the fermentor, the following changes were made:

agitation raised to 850 rpm back pressure raised to 0.8 bar

Using the concentrated feed, the O.D. was increased to 30. At that point the culture was induced by raising the temperature to 42° C. Other changes were made as follows:

air flow rate decreased to 24 L/ min oxygen flow rate increased to 3 L/min feed 1 decreased to 0 feed 2 started at 300 ml/hr

Feed 2 consisted of the following:

200 g/L Trypticase-peptone 100 g/L yeast extract 110 g/L glucose

After 4 hours at 42° C. the fermentation was halted and the cells were harvested by centrifugation into plastic bags contained within a one liter centrifuge bottle. Centrifugation was at 400 rpm for 60 minutes. At the end of this period, the supernatant was removed and the remaining cell paste was frozen at −90° C.

[1]Trace metals solution:

| | |
|---|---|
| 27 g/L | $FeCl_3.6H_2O$ |
| 2 g/L | $ZnCl_2.4H_2O$ |
| 2 g/L | $CaCl_2.6H_2O$ |
| 2 g/L | $Na_2.MoO_4.2H_2O$ |
| 1.9 g/L | $CuSO_4.5H_2O$ |
| 0.5 g/L | $H_3BO_3$ |
| 100 ml/L | concentrated HCl |

[2]Vitamin solution:

| | |
|---|---|
| 0.42 g/L | riboflavin |
| 5.4 g/L | pantothenic acid |
| 6 g/L | niacin |
| 1.4 g/L | pyridoxine hydrochloride |
| 0.06 g/L | biotin |
| 0.04 g/L | folic acid |

$NH_2$-terminal Amino Acid Sequencing $NH_2$-terminal amino acid sequence of *E. coli*-derived recombinant TIMP-3 protein was determined to be identical to the sequence deduced from the cDNA clones. The methionine initiator from the construct was cleaved off. There was no other detected proteolytic processing at the TIMP-3 $NH_2$-terminus. No assignment was made for cys-1 and cys-2 since the protein sample was reduced and reduced cysteines cannot readily be detected by this method. Therefore, the sequence read as follows: X-T-X-S-P-S-H-P-Q-D-A-F- (SEQ ID NO:41).

Methods

Partially purified recombinant TIMP-3 present in *E. coli* inclusion bodies was electrophoresed on an SDS polyacrylamide gel and electroblotted onto a PVDF membrane for sequence analysis. $NH_2$-terminal amino acid analysis was performed on a gas-phase sequenator (model 477, Applied Biosystems, Foster City, Calif.) according to published protocols. Hewick et al., J. Biol. Chem., 256: 2814–2818 (1981). The sequenator was equipped with an on-line phenylthiohydantoin (PTH) amino acid analyzer and a model 900 data analysis system (Hunkapiller et al., Methods of Protein Microcharacterization, Clifton, N.J.: pp. 223–247 (1986)). The PTH-amino acid analysis was performed with a micro liquid chromatography system (model 120) using dual syringe pumps and reversed phase (C-18) narrow bore columns (Applied Biosystems, Inc.), with the dimensions of 2.1 mm×240 mm.

Protein Purification

Approximately 435 g wet weight of *E. coli* cell paste, harvested from the fermentation run was resuspended to a volume of 1760 ml in water and broken by two passes through a microfluidizer. The cell lysate was centrifuged at 17,700×g for 30 min, and the pellet fraction was washed once with water (by resuspension and by recentrifugation). A portion of the washed pellet material (3.1% of the total) was resuspended in 10 ml of 50 mM Tris-HCl/50 mM dithiothreitol/2% (w/v) sodium N-lauroylsarcosine, pH 8.5. After incubation at 50° C. for 5 min, and at room temperature for 3hr, the mixture was centrifuged at 20,000 ×g for 60 min. The supernatant was applied to a Sephacryl S-200 gel filtration column (Pharmacia; 2×23 cm) equilibrated in 20 mM Tris-HCl/1% sodium N-lauroylsarcosine, pH 8.0, at room temperature. Fractions of 1 ml were collected at a flow rate of 5 ml/hr and analyzed by $A_{280}$ and by SDS/polyacrylamide gel electrophoresis (PAGE). Fractions 43–53 were pooled, and the pool was dialyzed over a 3-day period against 20 mM Tris-HCl (pH 8.0), 0.02% (w/v) sodium azide, at 4° C.

Figure 3:
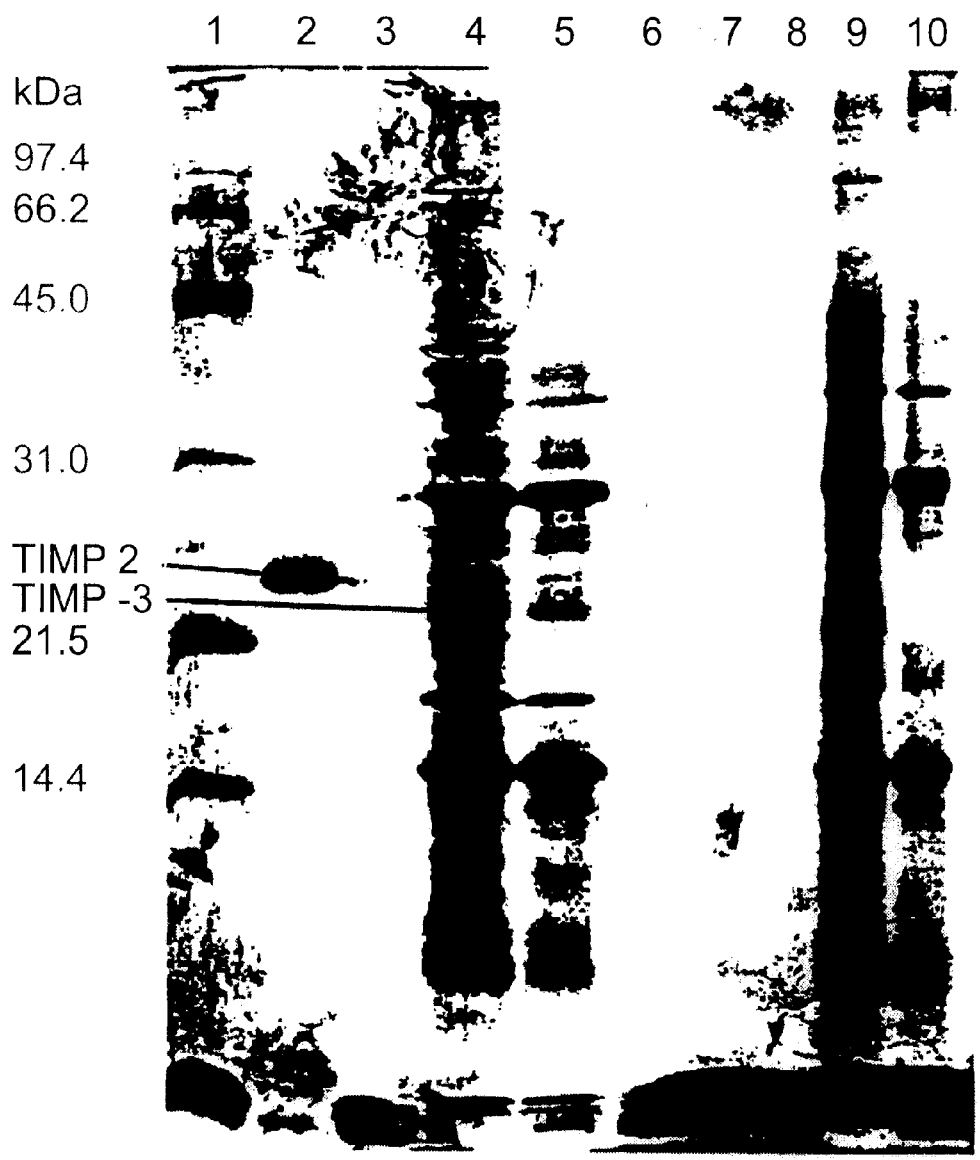
FIG. 3 is a photograph of a silver stained SDS-PAGE gel containing material as follows: Lane 1, molecular weight markers; lane 2, TIMP-2, reduced; lane 3, blank; lane 4, E. coli derived TIMP-3 of FIG. 1, reduced, post-dialysis; lane 5, E. coli derived TIMP-3 of FIG. 1, reduced, post-dialysis, lanes 6, 7, 8, blank; lane 9, E. coli derived TIMP-3 of FIG. 1, unreduced, pre-dialysis; lane 10, E. coli derived TIMP-3 of FIG. 1, unreduced, post-dialysis.

FIG. 3 presents a silver stained SDS-PAGE gel of the partially purified expression product from this fermentation. Lanes 3 and 4 contain reduced E. coli derived TIMP-3, pre- and post-dialysis. Lanes 9 and 10 contain unreduced E. coli derived TIMP-3, pre- and post-dialysis. As can be seen, the apparent molecular weight for reduced material is approximately 22 kDa.

As can be seen from FIG. 3, the post-dialysis yield was reduced; the polypeptide appeared to be somewhat unamenable to solubilization. In the present process, the presence of inclusion bodies containing relatively insoluble material resulted in a reduced yield of purified and isolated TIMP-3. Although this resulted in a partially purified product, one skilled in the act will recognize methods to obtain a purified and isolated polypeptide. For example, one may use different detergents as solubilizing agents, or use a different expression system, for example, one which permits secretion of the polypeptide (and thus elimination of inclusion bodies).

Expression and purification was also attempted using eucaryotic cells (COS-7 cells), however no active recombinant TIMP-3 polypeptide was observed. This may have been due to adherence of the recombinant TIMP-3 polypeptide to extracellular matrix material produced by COS-7 cells. One possible way to obtain active protein from a mammalian host cell may be to use cells which are non-adherent, and therefore produce no significant amount of extracellular matrix material. The recombinant polypeptide would then be found in the conditioned culture medium. For example Jurkat cells or U937 cells may be used for recombinant polypeptide expression, and other non-adherent host cells and expression systems will be apparent to those skilled in the art.

Results of Screening Two cDNA Libraries and Expression of Recombinant Human TIMP-3

The work herein presents the cloning and expression of a third class of mammalian TIMP family members, herein collectively referred to as "TIMP-3". The nucleotide sequence obtained from a human fetal kidney cDNA library is presented in FIG. 1. Seq. ID No. 12 As can be seen, the nucleic acid sequence obtained contains 1240 base pairs. The predicted amino acid sequence is also presented. Seq. ID No. 13 (The amino acid sequence is predicted, as the polypeptide itself was not fully sequenced. One skilled in the art may sequence the expression product of the E. coli deposited at the ATCC, accession no. 69455). The predicted initial cysteine of the mature protein is number +1. This prediction is based upon comparison to other members of the TIMP family.

FIG. 4 presents this comparison among the known members of the TIMP family. Bullet points (·) indicate those amino acid residue which are unique to the TIMP-3 of FIG. 1 obtained from expression of human cDNA, and bold-face type indicates conserved residues.

As can be see, the present human recombinant TIMP-3 of FIG. 1 is distinct from all other members of the TIMP family. While possessing the conserved cysteine residues and other conserved amino acids within the family (39, total), at least 23 amino acid residues are unique to the illustrated human recombinant TIMP-3.

FIGS. 5–13 illustrate the differences between the present human recombinant TIMP-3 of FIG. 1 and chicken TIMP-3 ("ChIMP-3," FIGS. 5–7), human TIMP-2 (FIGS. 8–10), and human TIMP-1 (FIGS. 11–13), at both the amino acid and nucleic acid levels. The Figures contain a solid line between amino acid residues which are identical, and dots indicating the degree of evolutionary distance. (For FIGS. 5, 8, and 11, illustrating amino acid alignment, the numbering at position "1" is for the mature polypeptide.)

At the amino acid level, TIMP-3 and ChIMP-3 are approximately 80% identical, with identical amino acids being more or less dispersed discontinuously, (FIG. 5). FIG. 6 shows that, at the nucleic acid level, FIG. 1 TIMP-3 DNA is approximately 74% homologous with ChIMP-3 DNA, between nucleic acids 151–1087 (TIMP-3) and 1–886 (ChIMP-3). FIG. 7 shows that even analyzing the region of maximal homology, base pairs 282–1040 from FIG. 1 TIMP-3, and 113–884 for ChIMP-3), there is approximately 78% identity.

FIGS. 8–10 illustrate a comparison between human recombinant TIMP-3 of FIG. 1 and human TIMP-2. At both the amino acid level and the nucleic acid level, there are greater distinctions than with ChIMP-3. FIG. 8 shows that there is approximately 46% identity at the amino acid level. FIG. 9 shows that, at the nucleic acid level, the overall homology is approximately 52% overall, and approximately 60% in the region of maximal homology (FIG. 10).

FIGS. 11–13 illustrate a comparison between human recombinant TIMP-3 of FIG. 1 and human TIMP-1. At the amino acid level, there is approximately 39% identity (FIG. 11), and approximately 47% overall homology at the nucleic acid level. There is approximately 65% identity in the region of maximal homology.

Biochemically, the calculated isoelectric points (pI) of the mature TIMP-3 polypeptide and its pre-cursor are 9.16 and 8.80, respectively. There is a potential glycosylation site at the carboxy-terminal sequence (184:NAT). While naturally occurring ChIMP-3 is reported to be non-glycosylated (Pavloff et al., supra, J. Biol. Chem. 267: at 17323), it is not currently known whether naturally occurring human TIMP-3 is glycosylated. Regardless, the present invention includes polypeptides with additional chemical moieties, such as carbohydrates. The hydrophobic leader of the FIG. 1 material is 23 amino acids long. Sequencing of the N-terminus confirmed the identity of the first 12 amino acids of the mature recombinant polypeptide.

The cloning and expression described herein demonstrates that the present TIMP-3 polypeptides represent new members in the TIMP family.

EXAMPLE 2

Expression of TIMP-3 In Various Cell Types

A variety of cells were tested for the expression of TIMP-3 RNA (which would indicate polypeptide expression). The results show that among normal (i.e., non-cancerous) cells, expression is observed in cells associated with extracellular matrix activity (i.e., growth or degradation). The normal cells (or tissues) where TIMP-3 RNA expression was seen (FIGS. 14A and B) are placenta, stromal cells, embryonic lung, newborn foreskin (one of two samples being slightly positive), and (slightly positive) adult lung. Among the cancer cells tested, some were positive, some were negative. For example, various breast adenocarinoma cell lines yielded disparate results; with one was positive, one was negative, one was slightly positive. This may indicate temporal expression, in that TIMP-3 expression may vary over the course of disease progression, although the significance is unclear. Table 2, below, presents a description of the cells tested and the results. Below are the methods.

In many of the positive cell lines three mRNA bands of approximate 2.2, 2.5 and 4.4 kb size were detected. The significance of the different mRNA bands is unknown but may represent alternative splicing or extended 3' or 5' untranslated regions. These may be RNAs encoding different naturally occurring variants.

Poly A+ RNA Preparation. Poly A+ RNA was prepared using Clontech (Palo Alto, CA) oligo dT-cellulose spun columns. 2×1 ml of a high salt buffer (10 mM Tris-HCl [pH

TABLE 2

ATCC Numbers Plus Description

| ATCC cell line | ATCC Number | Description | Poly A northern | Total RNA northern |
|---|---|---|---|---|
| Hs 294T | HTB 140 | metastatic melanoma | strongly positive | strongly positive |
| HepG2 | HB 8065 | hepatocellular carcinoma | slightly positive | |
| A-704 plus or minus | HTB 45 | adenocarcinoma, kidney | negative | |
| HuT 78 | TIB 161 | T cell lymphoma | negative | |
| MCF-7 plus | HTB 22 | breast adenocarcinoma | slightly positive | |
| MCF-7 minus | HTB 22 | breast adenocarcinoma | negative | |
| MDA-MB-231 | HTB 26 | breast adenocarcinoma | positive | |
| MDA-MB-453 | HTB 131 | breast carcinoma | negative | |
| Hs 68 | CRL 1635 | newborn human foreskin | | slightly positive |
| Hs 27 | CRL 1634 | newborn human foreskin | | negative |
| A 172 | CRL 1620 | glioblastoma | | negative |
| Hs 578 T | HTB 126 | ductal carcinoma, breast | | strongly positive |
| A-498 | HTB 44 | carcinoma, kidney | | borderline positive |
| 293 | CRL 1573 | transformed embryonal kidney | | borderline positive |
| SK-NEP-1 | HTB 48 | Wilms' tumor (kidney) | | borderline positive |
| WI-38 | CCL 75 | normal embryonic lung | | positive |
| WI-26 VA4 | CCL 95.1 | SV40 virus transformed lung | | borderline positive |
| CCD-11Lu | CCL 202 | normal lung | | borderline positive |
| DU 4475 | HTB 123 | breast carcinoma, metastatic nodule | | negative |
| BT-474 | HTB 20 | ductal carcinoma, breast | | negative |
| Caov-3 | HTB 75 | adenocarcinoma, ovary | | slightly positive |
| SK-OV-3 | HTB 77 | adencarcinoma, ovary | | negative |
| SK-Hep-1 | HTB 52 | adenocarcinoma, liver | | slightly positive |

Methods

Two types of Northern blots were performed, one on total RNA transcripts, and one using poly A+ tailed transcripts.

Total RNA Preparation. Total RNA for the total RNA northern was extracted from cells using a modification of a published protocol (Chomczynski and Sacchi, Anal. Biochem. 162: 156–159 (1987).

Cells grown in 2×10 cm petri dishes (approximately 2×10$^6$ cells), were washed two times with cold 1×PBS. After all of the PBS was aspirated off, 500 μl of an aqueous solution containing the following was added to each dish: 4 M guanidinium thiocyanate (Fluka), 25 mM sodium citrate pH 7.0 (Mallinckrodt), 0.5% sarcosyl (Sigma, St. Louis, Mo.) 0.1M β-mercaptoethanol (Sigma, St. Louis, Mo.). The cell lysate was pipetted into a 1.5 ml Eppendorf microfuge tube and was sheared with a 25 gauge needle.

Sodium acetate (pH 4) was added to the 500 μl lysate to make a final concentration of 0.2 M. The mixture was shaken vigorously by hand. ⅕ volume of chloroform was added and mixed thoroughly. The tubes were spun at 15,000 rpm for 5 minutes at 20° C. in a Tomy MTX-100 centrifuge. The tubes were inverted to allow the white precipitate layer to separate from the aqueous layer instead of respinning. The RNA was re-extracted with phenol and chloroform two additional times and was extracted one final time with chloroform. 1 ml of isopropanol was added to the microfuge tube and the mixture was precipitated at −20° C. overnight. The next day it was spun at 15,000 rpm for 15 minutes. The pellet was washed with 1 volume of 80% ethanol, re-spun, and dried in a Speed Vac (Savant, Farmingdale, N.Y.).

The pellet was resuspended in 400 μl of the guanidinium solution which contained β-mercaptoethanol (Sigma, St. Louis, Mo.). 800 μl of ethanol was added to this mixture, which was then spun at 15,000 rpm for 15 minutes and washed with 80% ethanol. This pellet was resuspended in 20 μl of water and the O.D. was determined.

7.4], 1 mM EDTA, 0.5 M NaCl) was washed through the columns and drained by gravity. Total RNA, isolated as described above, was resuspended in 1 ml of elution buffer (10 mM Tris-HCl [pH 7.4], 1 mM EDTA) and was heated at 68° C. for 3 minutes. 0.2 ml of sample buffer (10 mM Tris-HCl [pH 7.4], 1 mM EDTA, 3M NaCl) was added to the RNA solution, which was then placed on ice.

The samples were loaded onto the freshly equilibrated columns and allowed to soak under gravity. The columns were placed inside 50 ml tubes and were centrifuged at 350×g for 2 minutes. The eluates were discarded. 0.25 ml of the high salt buffer (see above) was added to each column and the columns were centrifuged at 350×g for 2 minutes. This wash was repeated once. In each case, the eluates were discarded. The columns were then washed 3 times with low salt buffer (10 mM Tris-HCl [pH 7.4], 1 mM EDTA, 0.1 M NaCl) and centrifuged each time at 350×g for 2 minutes. The eluates were discarded in each instance. Sterile 1.5 ml microcentrifuge tubes were placed inside of the 50 ml tubes to collect subsequent elutions. 0.25 ml of elution buffer (10 mM Tris-HCl [pH 7.4], 1 mM EDTA,) warmed to 65° C. were applied to the columns, which were then spun at 350×g for 2 minutes. This procedure was repeated 3 times for a total of 4 elutions per column. For each column, all of the elutions were collected in a microcentrifuge tube. The eluents were ethanol precipitated as above.

Northern Blotting. 10 μg of total RNA was loaded in each lane. The sample buffer included 10 μl of formamide, 3.5 μl of formaldahyde, 2 μl of 10×MOPS, 2 μl of loading dye, 0.2 μl of ethidium bromide, and 6.5 μl of RNA sample in water. The poly A+RNA blot had 3 μg of mRNA loaded in each lane.

The gels for the northern blots consisted of 1.5 g of agarose melted in 95 ml of water and then cooled to 60° C. 30 ml of 5×MOPS and 25 ml of formaldehyde (pH 4.7) were added to the cooling agarose solution. Prior to transfer, the gels were trimmed to remove excess gel. They were then soaked in distilled water for 5 minutes, followed by a 10 minute soak in 50 mM NaOH, 10 mM NaCl at room temperature. The gels were neutralized in 0.1 M Tris-HCl, pH 7.5 for 45 minutes and then soaked in 20×SSC for 1 hour. Transfer occurred overnight in 10×SSC. The gels were blotted onto Schleicher & Scheull (Keene, N.H.) nitrocellulose membranes. The total RNA gel was blotted onto pure nitrocellulose and fixed by UV crosslinking using a Stratalinker (Stratagene, La Jolla, Calif.). The poly A+ gel was blotted onto supported nitrocellulose and was baked in a vacuum oven for 2 hours at 80° C.

The blots were hybridized in a manner similar to the screening of the cDNA library. The sole difference is that for the northern blot analysis, RNase-free reagents were used wherever possible.

EXAMPLE 3

In Vitro Activity of Human Recombinant TIMP-3

Modified Zymogram

DeClerck et al. J. Biol. Chem. 266: 17445–17453 (1991) showed that TIMP-2 will bind to pAPMA-activated rabbit fibroblast interstitial collagenase in complexes that are stable in SDS. The 52 kDa inactive presursor was cleaved to an active 42 kDa protein by the organomercurial. Although the active protein primarily degrades type I, II and III collagen, it will also degrade gelatin to a lesser degree.

Conditioned medium (CM) from rabbit synovial fibroblasts contains interstitial collagenase as well as 72 kDa type IV gelatinase. The CM was incubated in 5 μl of 50 mM Tris-HCl, 200 mM NaCl, 10 mM CaCl$_2$, pH 7.5 for 15 minutes in either the presence or absence of TIMP-2 (according to EP 0 398 753), TIMP-2Δ or the FIG. 1 TIMP-3. Note that TIMP-2Δ refers to a trucated biologically active form of TIMP-2 with amino acids 128–194 of the mature protein deleted. Tolley et al., J. Mol. Biol. 229: 1163–1164(1993); Willenbrock et al., Biochemistry 32: 4430–4437 (1993). It has previously been shown that TIMP-2 interacts preferentially with 72 kDa procollagenase but that these complexes were not stable in 0.1% (w/v) SDS. Stetler-Stevenson, J. Biol. Chem., 264: 17374–17378 (1989). The TIMP-3 tested was the dialyzed TIMP-3 of FIG. 3.

In the absence of TIMPs, 2 zones of clearing are visible when CM from rabbit synovial fibroblasts is run on a 10% acrylamide, 0.1% gelatin gel. FIG. 15. One of the bands corresponds to 42 kDa pAPMA-activated interstitial collagenase. This clearing was absent in the presence of CM incubated with TIMP-2, TIMP2Δ, or the FIG. 1 TIMP-3. The other zone of clearing was not affected, meaning that it did not form as SDS-stable complex with the TIMP. In a separate experiment using the present methods (data not shown) a zone of clearing generated by the collagenase in medium conditioned by COS-7 cells was not inhibited by the presence of TIMP-2, TIMP-2Δ or TIMP-3.

EXAMPLE 4

Preparation of TIMP-3 Polypeptide Analogs and Nucleic Acid Variants

The amino acid sequence of full length TIMP-3 is presented in FIG. 1. Using the numbering of FIG. 1, the full length sequence is 188 amino acids long. The amino acid sequence at −23 through −1 is a leader sequence, and thus the pro version of the polypeptide is 211 amino acids in length.

The coding region of the TIMP-3 DNA of FIG. 1 is −69 through position 564 of the nucleic acid sequence illustrated.

Alternatively, for either variant, one may construct a signal peptide sequence for eucaryotic cell expression. As can be seen from FIG. 16, two additional cDNA clones have been isolated, TIMP3clone2. Seq. ID Nos. 14, 15 (ATCC Accession No. 69456) and TIMP3HCM-3 Seq. ID Nos. 16, 17 (ATCC Accession No. 69453). These clones represent natural variants. Timp3clone2 lacks part of the region encoding the N-terminus of the leader sequence of TIMP3clone7. As such, this would be preferably expressed in a procaryote, such as E. coli. TIMP3HCM-3 lacks a portion of the region encoding the NH$_2$-terminus of the mature protein. Since this clone lacks the hydrophobic leader sequence, it would be preferably expressed in a procaryote, such as E. coli.

FIG. 16 shows that there are some differences among the three cDNA clones. At nucleotide 320, there is an A in TIMP3clone 2 and a T in TIMP3clone7. This would result in a change in the amino acid sequence from a trp to an arg at position 14 in the hydrophobic leader sequence. This difference may be a cloning artifact due to its location at the 5' end of that clone. ChIMP-3 also has a trp at this position. Another divergence can be found at base 529, in which clone 2 has a C and clones 7 and HCM-3 have a T. This polymorphism does not result in an amino acid change because both CAT and CAC encode his. Other polymorphisms are found in or near the poly A tail. The poly A tail of HCM-3 is preceded by a single G, whereas in the other 2 clones it is preceded by GG. The poly A tail of clone 7 is 15 bases long and the poly A tail of HCM-3 is 18 bases long. The poly A tail of clone 2 is 17 bases long, is interrupted by 3 other bases, and is followed by 32 nucleotides of additional 5' untranslated sequence.

PCR product 29 (TIMP3PCR29 Seq. ID Nos. 18, 19, see FIG. 16) was also obtained from the human fetal kidney cDNA screening, using one insert specific primer and one vector specific primer as follows:

Seq. ID No. 21 (496-16)(CLWTDM forward): 5'-CGG AAT TCT GTC TCT GGA CCG ACA TGC TCT CC 3'.

Seq. ID No.20 (489-23)(lambda gt11 reverse): 5' GAC ACC AGA CCA ACT GGT AAT G 3'.

As can be seen from FIG. 16, this may represent a naturally occurring C-terminal variant. At FIGS. 16B, bottom, to 16C, top, differences in amino acid sequence between TIMP3clone7 and TIMP3PCR29 are indicated. TIMP3PCR29, cloned into pUC19 and placed into E. coli has been deposited at the ATCC with accession no. 69532. A full cDNA clone encompassing this PCR product has not been found in the fetal kidney cDNA library, however. It is unknown if TIMP3PCR29 represents a full or partial variant or a PCR artifact.

Other TIMP-3 analogs may be prepared. One type of analog is a truncated form which exhibits binding to the portion of a metalloproteinase which binds zinc. As indicated supra, the conserved region for this zinc binding domain may be represented by H E X G H, wherein X is either F or L. By analogy to TIMP-2 deletion analogs which have been prepared, TIMP-3 analogs maintaining enzyme inhibition activity may also be prepared.

FIG. 17 is an illustration of the proposed secondary structure for the TIMP family of proteins. See Alexander et al., Extracellular Matrix Degradation, in, Cell Biology of Extracellular Matrix (2d ed., Hay, ed.), Plenum Press, New York, pp. 255–302. As can be seen, the six C-terminal cysteines form a secondary structure which is somewhat separate from the structure formed by the region encompassing the first six cysteines. Previously, TIMP-2 analogs lacking the C-terminus up to and including the 6th cysteine in from the C-terminus have been shown to have activity. Willenbrock et al., Biochemistry 32: 4330–4337 (1993). TIMP-3 analogs lacking one or more of the C-terminal cysteines are those having the sequence (referring to the numbering of FIG. 1) of 1–121, and any of 1–122 through 1–188. Additions, deletions, and substitutions may also be made to amino acids 122–188, as well as attachment of chemical moieties, such as polymers.

While the present invention has been described in terms of preferred embodiments, it is understood that variations and modifications will occur to those skilled in the art. Therefore, it is intended that the appended claims cover all such equivalent variations which come within the scope of the invention as claimed.

What is claimed is:

1. A DNA sequence encoding a human recombinant TIMP-3 polypeptide selected from among (according to the numbering of the amino acid sequence as set forth in FIG. 1, Seq.ID No. 13):
    (a) a polypeptide having the amino acid sequence −23–188;
    (b) a polypeptide having the amino acid sequence 1–188;
    (c) a polypeptide having the amino acid sequence 1–121 and optionally, at the C-terminus, all or part of the amino acid sequence 122–188; and
    (d) a polypeptide of (b) or (c) having a methionyl residue at position −1.

2. A procaryotic or eucaryotic host cell transformed or transfected with a DNA sequence according to claim 1 in a manner allowing the host cell to express said polypeptide product.

3. A cDNA sequence according to claim 1.

4. A genomic DNA sequence according to claim 1, wherein said encoded polypeptide is selected from the polypeptide of subpart (a) or (b).

5. A DNA sequence according to claim 1 which encodes human TIMP-3.

6. A DNA sequence according to claim 1, the expression of which is optimized by the inclusion of one or more codons preferred for expression in bacterial cells.

7. A DNA sequence according to claim 1 the expression of which is optimized by the inclusion of one or more codons preferred for expression in mammalian cells.

8. A DNA sequence according to claim 1 the expression of which is optimized by the inclusion of one or more codons preferred for expression in yeast cells.

9. A DNA sequence according to claim 1 covalently associated with a detectable label substance.

10. A vector containing the DNA sequence according to claim 1.

11. A vector according to claim 10 wherein said vector is a plasmid vector.

12. A vector according to claim 10 wherein said vector is a viral vector.

13. A vector according to claim 12 wherein said viral vector is selected from the group consisting of a bacteriophage vector, a retroviral vector, and an adenoviral vector.

14. A process for the production of TIMP-3 comprising:
    growing, under suitable conditions, procaryotic or eucaryotic host cells transformed or transfected with a DNA according to claim 1, or a vector according to any of claims 10, 11, or 12 and isolating desired polypeptide products of the expression of said DNA sequences.

15. The host cell selected from the group consisting of those with ATCC designations (Timp3clone7/pCFM, Timp3clone7/puC19, Timp3clone2/puC19, Timp3HCM3, TimP3PCR29) 69455, 69454, 69456, 69453, and 69532.

* * * * *